US011247982B2

(12) United States Patent
Alami et al.

(10) Patent No.: US 11,247,982 B2
(45) Date of Patent: Feb. 15, 2022

(54) NMDA RECEPTOR MODULATORS, COMPOSITIONS COMPRISING SAME AND USE OF THESE COMPOUNDS IN THE TREATMENT OF DISEASES INVOLVING THE CENTRAL NERVOUS SYSTEM

(71) Applicant: ADPUERIVITAM, Antony (FR)

(72) Inventors: Mouad Alami, Bussy Saint Georges (FR); Jean Daniel Brion, Saint Leu la Foret (FR); Samir Messaoudi, Chilly Mazarin (FR); Sabrina Touchet, Vandoeuvre-les-Nancy (FR); Gilles Galvani, Bourg-la-Reine (FR); Olivier Dulac, Paris (FR); Svetlana Gataullina, Antony (FR); Caroline Nous, Itteville (FR)

(73) Assignee: ADPUERIVITAM, Antony (FR)

( * ) Notice: Subject to any disclaimer, the term of this patent is extended or adjusted under 35 U.S.C. 154(b) by 68 days.

(21) Appl. No.: 16/619,263

(22) PCT Filed: May 29, 2018

(86) PCT No.: PCT/EP2018/064093
§ 371 (c)(1),
(2) Date: Dec. 4, 2019

(87) PCT Pub. No.: WO2018/224359
PCT Pub. Date: Dec. 13, 2018

(65) Prior Publication Data
US 2020/0385363 A1 Dec. 10, 2020

(30) Foreign Application Priority Data
Jun. 6, 2017 (FR) ...................................... 1754993

(51) Int. Cl.
*C07D 401/14* (2006.01)
*C07D 403/06* (2006.01)
*C07D 405/14* (2006.01)
*C07D 409/14* (2006.01)

(52) U.S. Cl.
CPC ......... *C07D 403/06* (2013.01); *C07D 401/14* (2013.01); *C07D 409/14* (2013.01)

(58) Field of Classification Search
CPC .. C07D 401/14; C07D 403/06; C07D 407/14; C07D 409/14; C07D 405/14
See application file for complete search history.

(56) References Cited

FOREIGN PATENT DOCUMENTS

| WO | 2013063120 A2 | 5/2013 |
| WO | 2013114332 A1 | 8/2013 |
| WO | 2013123272 A1 | 8/2013 |
| WO | 2014055142 A1 | 4/2014 |

OTHER PUBLICATIONS

Newport et al. Am J Psychiatry 172:950-966. (Year: 2015).*
Su et al. Brain Science Advances 4(2): 73-98. (Year: 2018).*
Hoffmann et al. Neurotherapeutics, vol. 15, p. 361-370 . (Year: 2018).*
Banerjee et al.; "Synthesis of Iboga-like Isoquinuclidines: Dual opioid receptors agonists having antinociceptive properties"; Biorganic & Medicinal Chemistry, vol. 22; 2014; pp. 6062-6070.
Berge et al.; "Pharmaceutical Salts"; Journal of Pharmaceutical Sciences, vol. 66, Issue No. 1; 1977; pp. 1-19.
Campaigne et al.; "Benzo[b]thiophene derivatives. XXV. Condensation and reductive alkylation of 3-aminoalkylbenzo[b] thiophenes with formaldehyde"; Journal of Heterocyclic Chemistry, vol. 16, Issue No. 7; 1979; pp. 1321-1324.
Campos et al.; "A General Synthesis of Substituted Indoles from Cyclic Enol Ethers and Enol Lactones"; Organic Letters, vol. 6, Issue No. 1; 2004; pp. 79-82.
Chen, H.-S et al.; "The chemical biology of clinically tolerated NMDA receptor antagonists"; Journal of Neurochemistry, vol. 97, Issue No. 6; 2006; pp. 1611-1626.
Contour-Gakcera, et al.; "3-Thio-1, 2, 4-triazoles, novel somatostatin sst2/sst5 agonists"; Bioorganic & Medicinal Chemistry Letters, vol. 15, Issue No. 15; 2005; pp. 3555-3559.
Goff et al.; "Once-weekly D-Cycloserine Effects on Negative Symptoms and Cognition in Schizophrenia: An Exploratory Study"; Schizophrenia Research, vol. 106, Issue No. 2-3; 2008; pp. 320-327.
Hallett, et al.; "Rationale for and use of NMDA receptor antagonists in Parkinson's disease"; Pharmacology & Therapeutics vol. 102, Issue No. 2; 2004; pp. 155-174.
International Search Report and Written Opinion: International Application No. PCT/EP2018/064093; International Filing Date May 29, 2018; dated Aug. 20, 2018; 11 pagesd.
Kruegel et al.; "Constructing Iboga Alkaloids via C—H Bond Functionalization: Examination of the Direct and Catalytic Union of Heteroarenes and Isoquinuclidine Alkenes"; The Journal of Organic Chemistry, vol. 80, Issue No. 4; 2015; pp. 2062-2071.

(Continued)

*Primary Examiner* — Emily A Bernhardt
(74) *Attorney, Agent, or Firm* — Cantor Colburn LLP

(57) ABSTRACT

The present invention relates to the field of prevention and treatment of diseases involving NMDA receptors of the central nervous system. It relates more specifically to compounds of 1-(indol-3-yl)-3-hydroxy-3-(2-oxo-2-ethyl)-indol-2-ones type, as a drug, and the use of such compounds in the preparation of pharmaceutical compositions. These pharmaceutical compositions may in particular be intended to prevent or treat diseases involving NMDA receptors of the central nervous system, in particular severe/resistant epilepsy and cognitive disorders resulting therefrom, especially autism, but also strokes, schizophrenia, degenerative diseases involving the activation of NMDA receptors, such as Parkinson's disease and Alzheimer's disease, Rett syndrome, or amyotrophic lateral sclerosis, migraine, dementia and major depressive disorder.

14 Claims, No Drawings

(56) References Cited

OTHER PUBLICATIONS

Nagle et al.; "3-(2-Oxoethylidene)indolin-2-one Derivatives Activate Nrt2 and Inhibit NF-kB: Potential Candidates for Chemoprevention"; ChemMedChem, vol. 9, Issue No. 8; 2014; pp. 1763-1774.

Oisaki et al.; "Manganese-catalyzed aerobic dehydrogenative cyclization toward ring-fused indole skeletons"; Organic & Biomolecular Chemistry, vol. 11, Issue No. 28; 2013; pp. 4669-4562.

Srinavasa et al.; "A direct and simple approach for the synthesis of indole-3-propanol and its acetates from dihydropyran"; Monatshefte für Chemie-Chemical Monthly, vol. 139, Issue No. 12; 2008; pp. 1475-1478.

Thanh et al.; "Reaction of N-alkylisatins with 4-(2, 3, 4, 6-tetra-O-acetyl-?-D-glucopyranosyl) thiosemicarbazide"; Journal of Chemistry, vol. 2013; 2012; pp. 1-5.

Vance et al.; "Ligand specific deactivation time course of GluN1/GluN2D NMDA receptors"; Nature Communications vol. 2, Issue No. 1; 2011; pp. 1-11.

Yang et al.; "Gold(I)-catalyzed highly stereoselective synthesis of polycyclic indolines: the construction of four contiguous stereocenters"; Chemical Communications, vol. 52, Issue No. 2; 2016; pp. 346-349.

Zhang et al.; "Facile Solid-Phase Construction of Indole Derivatives Based on a Traceless, Activating Sulfonyl Linker"; Organic Letters, vol. 2, Issue No. 1; 2000; pp. 89-92.

Zhou et al.; "One-pot synthesis of 2-substituted benzo[b]furans via Pdtetraphosphinecatalyzed couping of 2-halophenols with alkynes"; Chemical Communications, vol. 50, Issue No. 45; 2014; pp. 6023-6026.

Amidfar, M. et al.; "The role of NMDA receptor in neurobiology and treatment of major depressive disorder: Evidence from translational research"; Progress in Neuropsychopharmacology & Biology Psychiatry, vol. 94, Issue No. 109668; 2019; 23 pages; doi: 10.1016/j.pnpbp.2019.109668.

Auvin, S. et al.; "Radiprodil, a NR2B negative allosteric modulator, from bench to bedside in infantile spasm syndrome"; Annals of Clinical and Translational Neurology, vol. 7, Issue No. 3; 2020; pp. 343-352.

Czarnecka, K. et al.; "Memantine in neurological disorders—schizophrenia and depression"; Journal of Molecular Medicine, vol. 99, Issue No. 3; 2021; pp. 327-334.

Folch, J. et al.; "Memantine for the Treatment of Dementia: A Review on its Current and Future Applications"; Journal of Alzheimer's Disease, vol. 62, Issue No. 3; 2018; pp. 1223-1240.

Iqbal, S. et al.; "Ketamine for depression clinical issues"; Advances in Pharmacology, vol. 89; 2020; pp. 131-162.

Katz, D. et al.; "N-Methyl-D-Aspartate Receptors, Ketamine, and Rett Syndrome: Something Special on the Road to Treatments?"; Biological Psychiatry, vol. 79, Issue No. 9; 2016; pp. 710-712.

Kikuchi, T.; "Is Memantine Effective as an NMDA Receptor Antagonist in Adjunctive Therapy for Schizophrenia?"; Biomolecules, vol. 10, Issue No. 8; 2020; 23 pages; doi: 10.3390/biom10081134.

Koola, M.; "Galantamine-Memantine combination in the treatment of Alzheimer's disease and beyond"; Psychiatry Research, vol. 293, Issue No. 113409; 2020; 8 pages; doi: 10.1016/j.psychres.2020.113409.

Lozovaya, N. et al.; "Selective suppression of excessive GluN2C expression rescues early epilepsy in a tuberous sclerosis murine model"; Nature Communications, vol. 5, Issue No. 4563; 15 pages; doi: 10.1038/ncomms5563.

Niquet, J. et al.; "Rational polytherapy in the treatment of cholinergic seizures"; Neurobiology of Disease, vol. 133, Issue No. 104537; 2020; 11 pages; doi: 10.1016/j.nbd.2019.104537.

Ogden, O. et al.; "New advances in NMDA receptor pharmacology"; Trends in Pharmacological Sciences, vol. 32, Issue No. 12; 2011; pp. 726-733.

Tang, S. et al.; "Altered NMDAR signaling underlies autistic-like features in mouse models of CDKL5 deficiency disorder"; Nature Communications, vol. 10, Issue No. 2655; 2019; 14 pages; https://doi.org/10.1038/s41467-019-10689-w.

Ueda, K. et al.; "Clinical Benefit of NMDA Receptor Antagonists in a Patient With ATP1A2 Gene Mutation"; Pediatrics, vol. 141, Supplement 5; 2018; pp. S390-S394.

Vanle, B. et al.; "NMDA antagonists for treating the non-motor symptoms in Parkinson's disease"; Translational Psychiatry, vol. 8, Issue No. 117; 2018; 15 pages; doi: 10.1038/S41398-018-0162-2.

\* cited by examiner

NMDA RECEPTOR MODULATORS, COMPOSITIONS COMPRISING SAME AND USE OF THESE COMPOUNDS IN THE TREATMENT OF DISEASES INVOLVING THE CENTRAL NERVOUS SYSTEM

CROSS REFERENCE TO RELATED APPLICATIONS

This application is a National Stage application of PCT/EP2018/064093, filed on May 29, 2018, which claims the benefit of French Application No. 1754993, filed on Jun. 6, 2017, both of which are incorporated by reference in their entirety herein.

TECHNICAL FIELD

The present invention relates to the field of preventing and treating diseases involving the NMDA receptors of the central nervous system.

The invention relates more precisely to compounds of the 1-(indol-3-yl)-3-hydroxy-3-(2-oxo-2-ethyl)indol-2-one type, notably as active principle, and to the use of such compounds in the preparation of pharmaceutical compositions. These pharmaceutical compositions may notably be intended for preventing or treating pathologies involving the NMDA receptors of the central nervous system, in particular severe/resistant epilepsy and cognitive disorders resulting therefrom, notably autism, but also strokes, schizophrenia, degenerative diseases involving activation of the NMDA receptors such as Parkinson's disease and Alzheimer's disease, Rett's syndrome or amyotrophic lateral sclerosis, migraine, dementia and major depression.

PRIOR ART

The N-methyl-D-aspartate (NMDA) receptors are specific ionotropic receptors activated under physiological conditions by glutamate and glycine. The NMDA receptors play a fundamental role in excitatory synaptic transmission and excitotoxicity in the central nervous system. They are largely present throughout the central nervous system and involved in numerous physiological processes such as memory, synaptic plasticity or axonal guiding. Thus, these receptors appear as very good therapeutic targets for various neurological diseases such as strokes, schizophrenia, major depression, Parkinson's disease, Alzheimer's disease and dementia (cf. a) Chen, H.-S. V.; Lipton, A. S. The chemical biology of clinically tolerated NMDA receptor antagonists. *J. Neurochem.* 2006, 97, 1611-1626. b) Hallett, P. J.; Standaert, D. G. Rationale for and use of NMDA receptor antagonists in Parkinson's disease. *Pharmacol. Ther.* 2004, 102, 155-174. c) Vance, K. M.; N., S.; Traynelis, S. F.; Furukawa, H. Ligand specific deactivation time course of GluN1/GluN2D NMDA receptors. *Nat. Commun.* 2011, 2, 294. d) Goff, D. C.; Cather, C.; Gottlieb, J. D.; Evins, A. E.; Walsh, J.; Raeke, L.; Otto, M. W.; Schoenfeld, D.; Green, M. F. Once-weekly Dcycloserine effects on negative symptoms and cognition in schizophrenia: an exploratory study. *Schizophr. Res.* 2008, 106, 320-327).

Seven NMDA receptor subunits have been identified to date: one subunit GluN1, four subunits GluN2 (GluN2A/B/C/D) and two subunits GluN3 (GluN3A/B). The GluN3 subunit does not allow the formation of a functional receptor; however, it can assemble with the GluN1/GluN2 subunits. To be functional, an NMDA receptor must be tetrameric and composed of several GluN1 subunits in combination with at least one GluN2 subunit (A, B, C or D), which makes it possible to generate a multitude of different NMDA receptors with intrinsic pharmacological and biological properties.

The various GluN2A/B/C/D subunits of the NMDA receptors are distributed differently according to the regions of the brain with expression levels which vary remarkably during development. The GluN1 subunits are expressed only in the central nervous system, whereas the GluN2 subunits vary in composition and expression during development and according to the regions of the body. The GluN2B and GluN2C subunits are predominant in the neonatal brain. However, during development, they are gradually complemented or replaced with GluN2A subunits and, in certain regions, with GluN2C subunits. As the four GluN2 subunits (GluN2A/B/C/D) are responsible for the pharmacological and biological properties of the NMDA receptors, an action targeted on only one of these subunits would allow precise efficiency, in terms of therapeutic effect and localization in the brain, making it possible to limit the adverse effects due to a global action on the NMDA receptors.

The pharmacology of the NMDA receptors is highly diversified, mainly due to the complex assembly of these subunits which form singular units thereof. However, the resolution of GluN1/GluN2/ligand complex crystalline structures has enabled the development of antagonists that are selective for the various GluN2 subunits. To date, the majority of the NMDA receptor antagonists which have entered clinical phases have failed on account of unacceptable adverse effects, such as sedative and hallucinogenic effects, at the minimum effective doses. Such was the case for dizocilpine (MK-801), a noncompetitive NMDA receptor antagonist. Despite years of effort in developing molecules that are capable of interacting specifically with the NMDA receptors, only a few reached the clinical phase. Memantine, a noncompetitive antagonist, is used in the treatment of Alzheimer's disease and Lewy body dementia. Ketamine is administered mainly for initiating and maintaining general anesthesia. However, during recent clinical tests, ketamine made it possible to treat depression resistant to the conventional treatment. Amantadine is, itself, indicated as an antiviral agent and also in the treatment of Parkinson's disease.

There is thus a need for novel NMDA receptor antagonist compounds and more largely for modulators of these receptors.

Definitions

In order to facilitate understanding of the invention, a certain number of terms and expressions are defined below:

Generally speaking, the term "substituted", whether or not preceded by the term "optionally", and the substituents described in the formulae of the present document, denote the replacement of a hydrogen radical in a given structure with the radical of a specified substituent. The term "substituted" denotes for example the replacement of a hydrogen radical in a given structure with a radical R. When more than one position may be substituted, the substituents may be the same or different at each position.

For the purposes of the present invention, the term "alkyl" means a saturated, linear, branched or cyclic, optionally substituted carbon-based radical, comprising 1 to 25 carbon atoms, for example 1 to 10 carbon atoms, for example 1 to 8 carbon atoms, for example 1 to 6 carbon atoms. For example, alkyl groups include, without being limited thereto, methyl, ethyl, n-propyl, isopropyl, n-butyl, secbutyl, isobutyl, tert-butyl, n-pentyl, sec-pentyl, isopentyl, tert-pentyl, n-hexyl, sec-hexyl, etc.

For the purposes of the present invention, the term "haloalkyl" means an alkyl radical as defined above, substituted with at least one halogen atom. For example, haloalkyl groups include, without being limited thereto, chloromethyl, bromomethyl, trifluoromethyl, etc.

For the purposes of the present invention, the term "aryl" means an aromatic system comprising at least one ring which complies with Hückel's aromaticity rule. Said aryl is optionally substituted and may comprise from 6 to 50 carbon atoms, for example 6 to 20 carbon atoms, for example 6 to 10 carbon atoms. Mention may be made, for example, of phenyl, indanyl, indenyl, naphthyl, phenanthryl and anthracyl.

For the purposes of the present invention, the term "heteroaryl" means a system comprising at least one 5- to 50-membered aromatic ring, among which at least one member of the aromatic ring is a heteroatom notably chosen from the group comprising sulfur, oxygen, nitrogen and boron. Said heteroaryl is optionally substituted and may comprise from 1 to 50 carbon atoms, preferably 1 to 20 carbon atoms, preferably 3 to 10 carbon atoms. Mention may be made, for example, of pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furyl, quinolyl, isoquinolyl, and the like. Mention may be made, for example, of pyridyl, quinolyl, dihydroquinolyl, isoquinolyl, quinazolinyl, dihydroquinazolyl and tetrahydroquinazolyl.

For the purposes of the present invention, the term "arylalkyl" means an aryl substituent bonded to the rest of the molecule via an alkyl radical. An analogous convention is used for the term "heteroarylalkyl".

For the purposes of the present invention, the term "alkoxyl" means an alkyl substituent as defined above, bonded to the rest of the molecule via an oxygen atom. Mention may be made, for example, of methoxyl, ethoxyl, etc.

For the purposes of the present invention, the term "halogen" denotes an atom chosen from fluorine, chlorine, bromine and iodine.

For the purposes of the present invention, the term "independently" means that the substituents, atoms or groups to which this term refers are chosen from the list of variables independently of each other (in other words, they may be identical or different).

DESCRIPTION OF CERTAIN ADVANTAGEOUS EMBODIMENTS OF THE INVENTION

Thus, according to a first aspect, the purpose of the invention is the isolated compounds corresponding to formula (I) below or a pharmaceutically acceptable salt thereof:

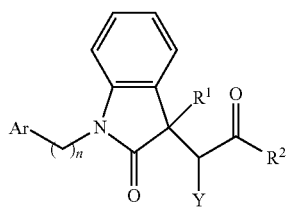

(I)

wherein:
$R^1$ represents H or OH; preferably OH;
$R^2$ represents CN, $NH_2$, OH or a linear, branched or cyclic $C_{1-6}$ alkyl radical; a $C_{6-10}$ aryl radical optionally substituted with one or more substituents chosen from a halogen atom, a linear, branched or cyclic $C_{1-6}$ alkyl radical, a linear, branched or cyclic $C_{1-6}$ alkoxy radical, a linear, branched or cyclic $C_{1-6}$ haloalkyl radical, a linear, branched or cyclic $C_{1-6}$ haloalkoxy radical; a $C_{6-10}$ heteroaryl radical optionally substituted with one or more substituents chosen from a halogen atom, a linear, branched or cyclic $C_{1-6}$ alkyl radical, a linear, branched or cyclic $C_{1-6}$ alkoxy radical, a linear, branched or cyclic $C_{1-6}$ haloalkyl radical, a linear, branched or cyclic $C_{1-6}$ haloalkoxy radical; or a saturated or unsaturated $C_{2-5}$ heterocyclic radical comprising from 1 to 3 heteroatoms selected from the group comprising O, N and S;
Y represents H or a linear, branched or cyclic $C_{1-6}$ alkyl radical; or alternatively Y taken together with $R^2$ forms a 5- or 6-membered ring;
n represents 0, 1, 2, 3 or 4; preferably, n represents 2 or 3;
Ar represents a bicyclic heterocycle having the structure:

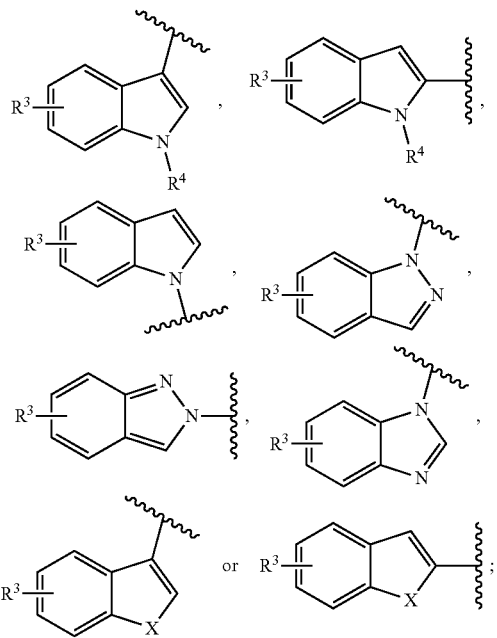

wherein:
$R^3$ represents H, a halogen atom, a radical $-OR^5$ or $-NR^{6A}R^{6B}$; in which $R^5$ represents a H or linear, branched or cyclic $C_{1-6}$ alkyl radical; and $R^{6A}$ and $R^{6B}$ independently represent H, linear, branched or cyclic $C_{1-6}$ alkyl or $C_{6-10}$ aryl;
$R^4$ represents H; a linear, branched or cyclic $C_{1-6}$ alkyl radical; or a radical $-C(=O)R^7$ in which $R^7$ represents a linear, branched or cyclic $C_{1-6}$ alkyl radical; and
X represents O or S.

For example, n may be advantageously equal to 2 or 3.
For example, $R^1$ may advantageously represent OH.
For example, Y may represent H or methyl, or else Y, taken together with $R^2$, may form a 5-membered ring. Advantageously, Y may represent H.
When Y forms with $R^2$ a 5- or 6-membered ring, the carbon alpha to the ketone function which bears Y may be a chiral center, for example of R or S configuration, or else may be racemic.

For example, Ar may represent a bicyclic heterocycle having the following structure:

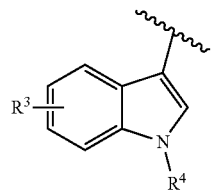

in which

R³ represents H; a halogen atom chosen from F, Cl or Br, preferably Cl; a radical —OR⁵ in which R⁵ represents H, methyl or ethyl; or a radical —NR⁶ᴬR⁶ᴮ in which R⁶ᴬ and R⁶ᴮ independently represent H, methyl or ethyl; and R⁴ represents H or methyl.

For example, Ar may also represent a bicyclic heterocycle having the following structure:

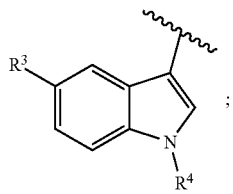

wherein

R³ represents H; a halogen atom chosen from F, Cl or Br, preferably Cl; a radical —OR⁵ in which R⁵ represents H, methyl or ethyl; or a radical —NR⁶ᴬR⁶ᴮ in which R⁶ᴬ and R⁶ᴮ independently represent H, methyl or ethyl; and R⁴ represents H or methyl.

By way of example, R² represents:

methyl, ethyl, propyl, n-butyl, isopropyl, isobutyl, cyclopropyl, cyclobutyl, cyclopentyl or cyclohexyl;

a phenyl radical optionally substituted with one or more substituents chosen from F, C, Br, methyl, ethyl, CN, CF₃, OH, methoxy, NH₂ or OCF₃; preferably a phenyl radical which is unsubstituted or monosubstituted in the ortho, meta or para position with a substituent chosen from F, C, Br, methyl, ethyl, CN, CF₃, OH, methoxy, NH₂ or OCF₃, or a pyridyl radical optionally substituted with one or more substituents chosen from F, C, Br, methyl, ethyl, CF₃, OH, methoxy, NH₂ or OCF₃; preferably a pyridyl radical

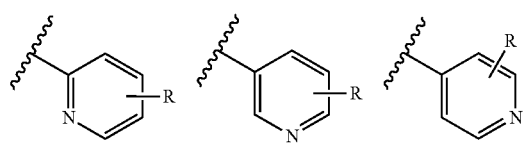

optionally substituted with a substituent R chosen from H, F, C, Br, methyl, ethyl, CF₃, OH, methoxy, NH₂ or OCF₃; preferably H or a benzofuryl radical having the structure

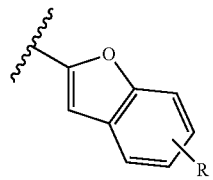

optionally substituted with one or more substituents R chosen from F, Cl, Br, methyl, ethyl, CN, CF₃, OH, methoxy, NH₂ or OCF₃; or a saturated or unsaturated C₄₋₅ heterocyclic radical comprising from 1 to 3 heteroatoms chosen from the group comprising O and S;

a furyl radical having the structure

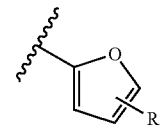

optionally substituted with one or more substituents R chosen from F, C, Br, methyl, ethyl, CN, CF₃, OH, methoxy, NH₂ or OCF₃, preferably a furyl radical having the structure

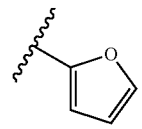

a thiophene radical having the structure

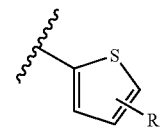

optionally substituted with one or more substituents R chosen from F, C, Br, methyl, ethyl, CN, CF₃, OH, methoxy, NH₂ or OCF₃; or a benzothiophene radical having the structure

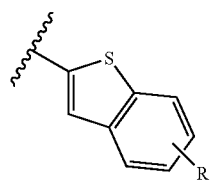

optionally substituted with one or more substituents R chosen from F, C, Br, methyl, ethyl, CN, CF₃, OH, methoxy, NH₂ or OCF₃, preferably a benzofuryl radical having the structure

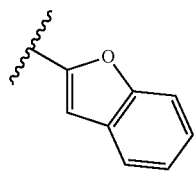 [SMILES: *c1cc2ccccc2o1]

Advantageously, the compounds according to the invention may correspond to formula (I) below or a pharmaceutically acceptable salt thereof:

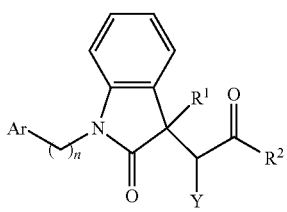
(I)

wherein
$R^1$ represents OH;
Ar may also represent a bicyclic heterocycle having the following structure:

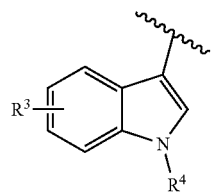

wherein $R^3$ represents H or Cl; $R^4$ represents H or methyl;
$R^2$ represents a phenyl radical which is unsubstituted or monosubstituted in the ortho, meta or para position with a substituent chosen from F, C, Br, methyl, ethyl, CN, $CF_3$, OH, methoxy, $NH_2$ or $OCF_3$;
Y represents H or methyl; and
n is equal to 2.

Advantageously, the compounds according to the invention may correspond to formula (I) below or a pharmaceutically acceptable salt thereof:

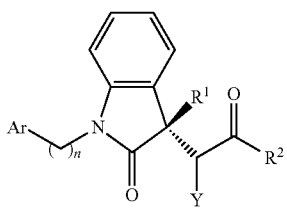
(I)

wherein
$R^1$ represents OH;
Ar represents a bicyclic heterocycle having the following structure:

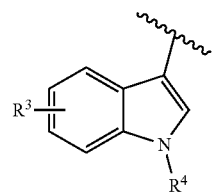

in which $R^3$ represents H or Cl; $R^4$ represents H or methyl;
$R^2$ represents ethyl, n-butyl, isopropyl, isobutyl, an unsubstituted pyridyl radical, a cyclic $C_{3-6}$ alkyl radical, a furyl radical having the structure

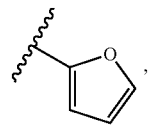 [SMILES: *c1ccco1], a thiophene radical having the structure

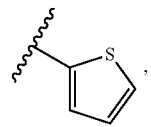, or a benzofuryl radical having the structure

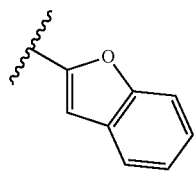 [SMILES: *c1cc2ccccc2o1]

Y represents H; and
n is equal to 2.

Advantageously, the compounds according to the invention may correspond to formula (I) below or a pharmaceutically acceptable salt thereof:

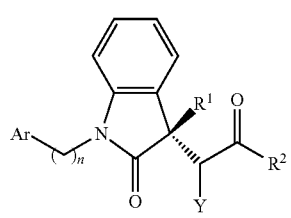
(I)

wherein
$R^1$ represents OH;
Ar represents a bicyclic heterocycle having the following structure:

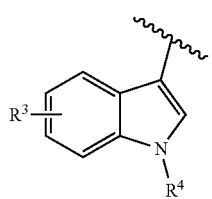

in which $R^3$ represents H; $R^4$ represents H;
$R^2$ represents a phenyl radical which is monosubstituted in the ortho or meta-position with a substituent chosen from F and Cl;
Y represents H; and
n is equal to 2.

Advantageously, the compounds according to the invention may correspond to formula (I) below or a pharmaceutically acceptable salt thereof:

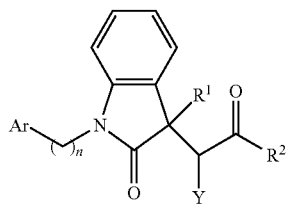

(I)

in which
$R^1$ represents OH;
Ar may also represent a bicyclic heterocycle having the following structure:

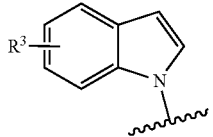

in which $R^3$ represents H or Cl;
$R^2$ may represent a phenyl radical which is unsubstituted or monosubstituted in the ortho, meta or para position with a substituent chosen from F, C, Br, methyl, ethyl, CN, $CF_3$, OH, methoxy, $NH_2$ or $OCF_3$;
Y represents H or methyl; and
n is equal to 2.

Advantageously, the compounds according to the invention may correspond to formula (I) below or a pharmaceutically acceptable salt thereof:

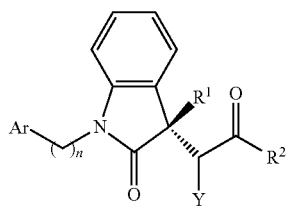

(I)

wherein
$R^1$ represents OH;

Ar may also represent a bicyclic heterocycle having the following structure:

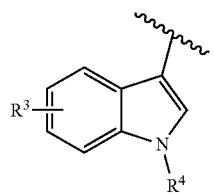

in which $R^3$ represents H or Cl; $R^4$ represents H;
$R^2$ may represent a phenyl radical which is unsubstituted or monosubstituted in the ortho, meta or para position with a substituent chosen from F, C, Br, methyl, ethyl, CN, $CF_3$, OH, methoxy, $NH_2$ or $OCF_3$;
Y represents H or methyl; and
n is equal to 3.

Advantageously, the compounds according to the invention may correspond to one of the following structures:

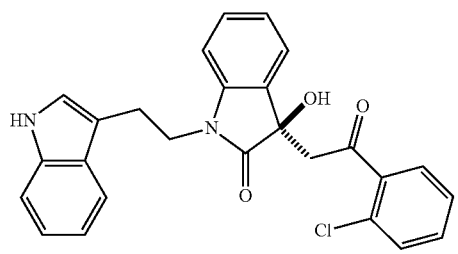

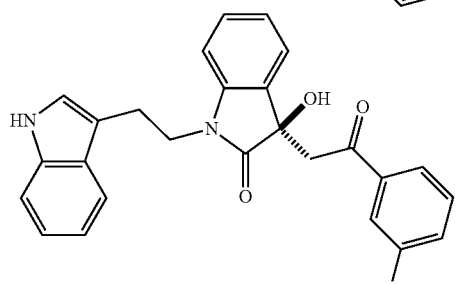

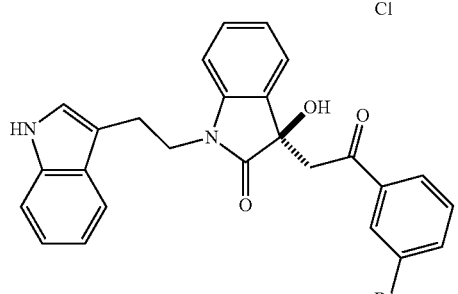

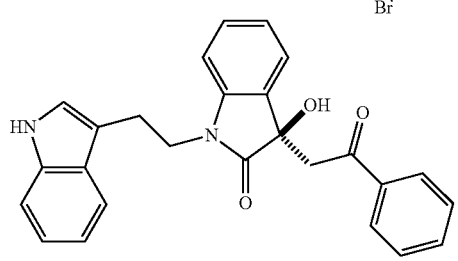

-continued
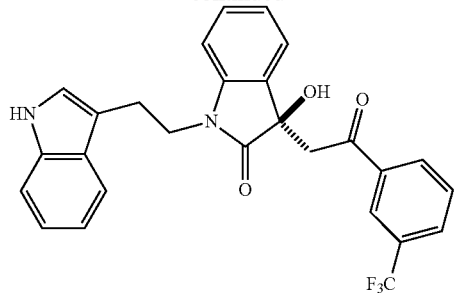
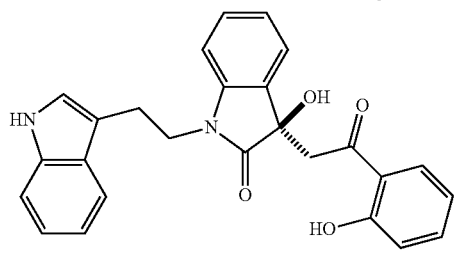
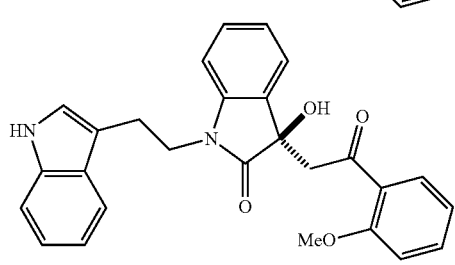
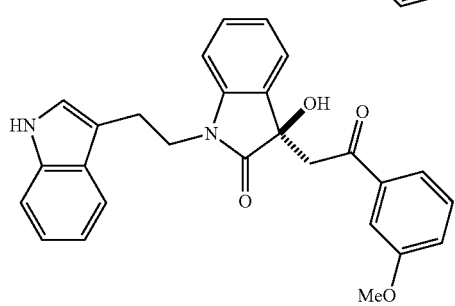
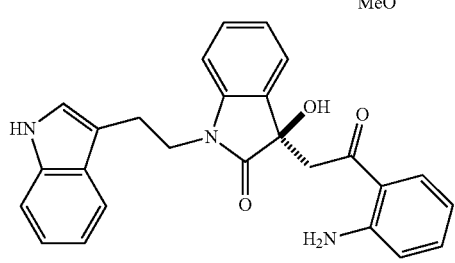
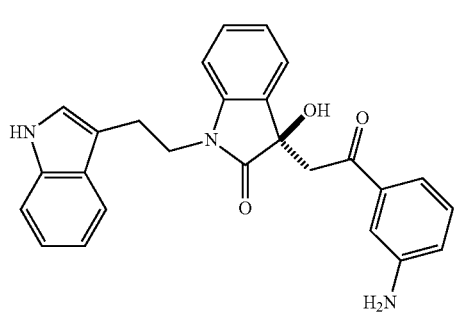
-continued
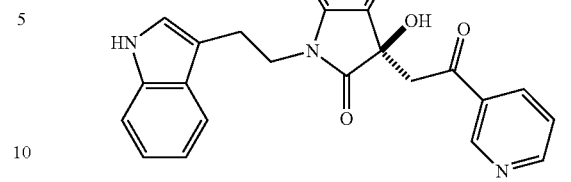
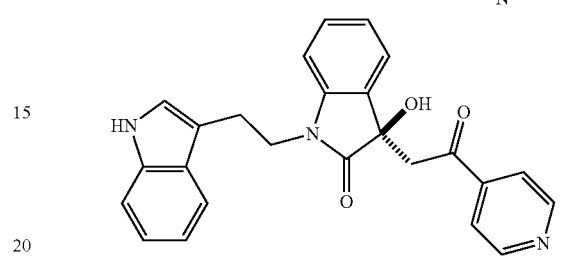
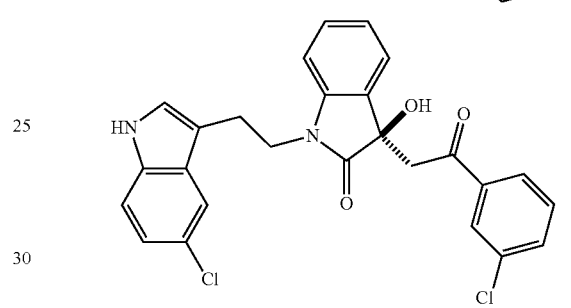
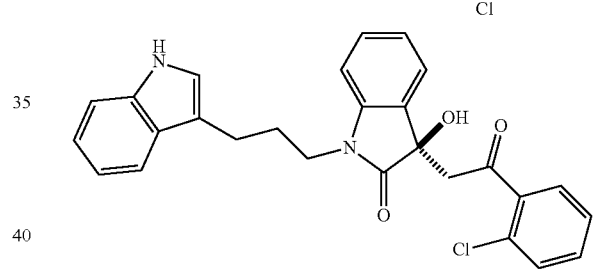
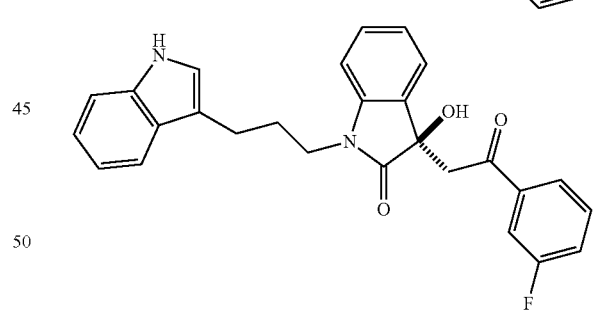
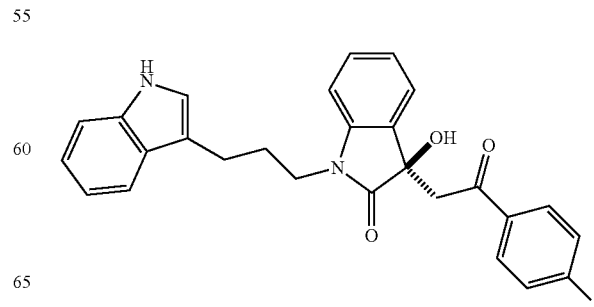

-continued
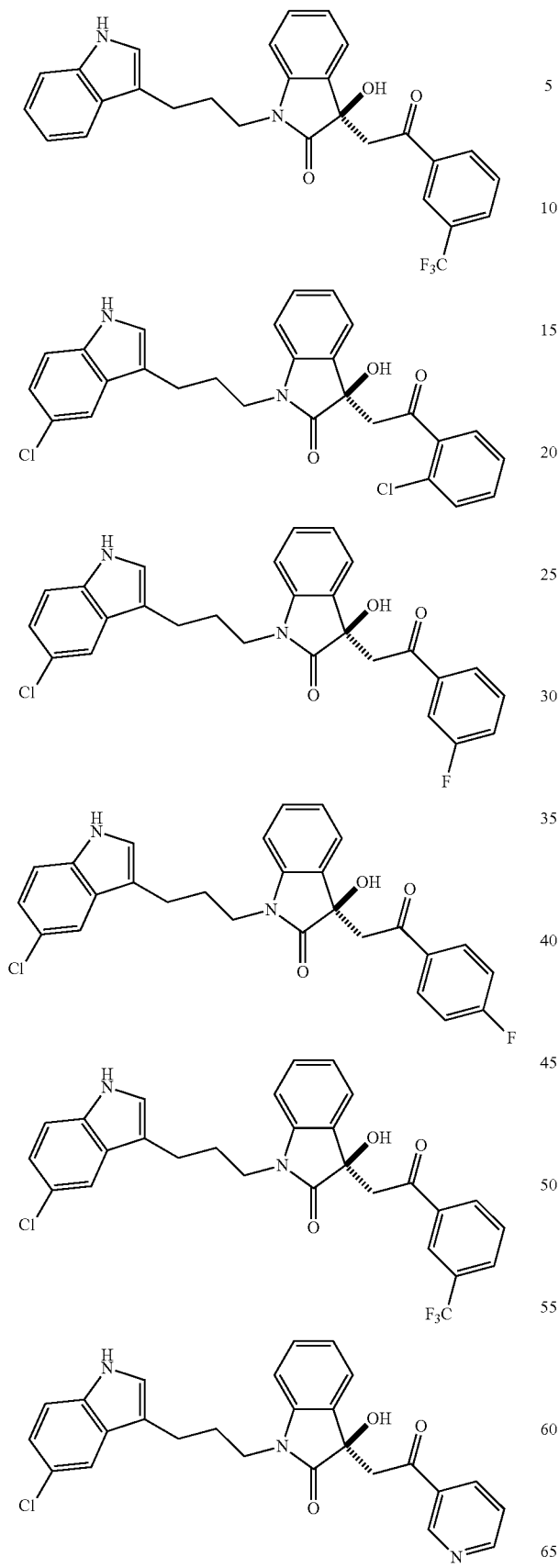
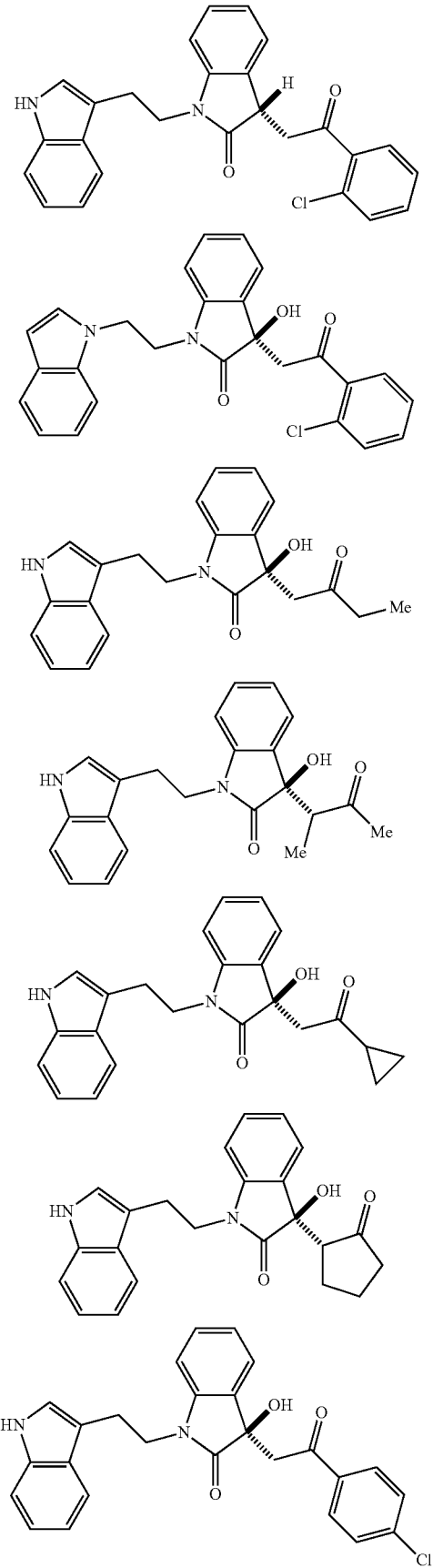

15
-continued
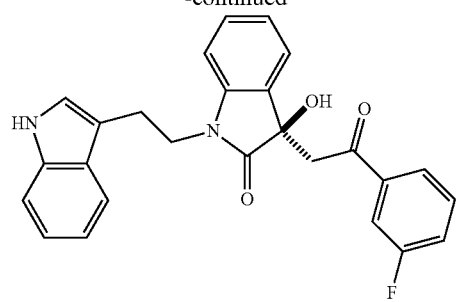
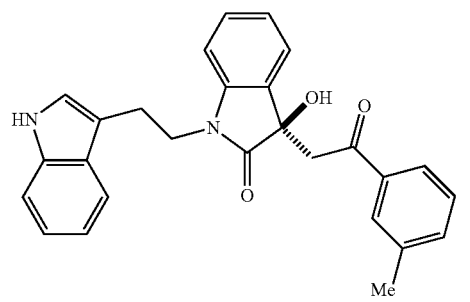
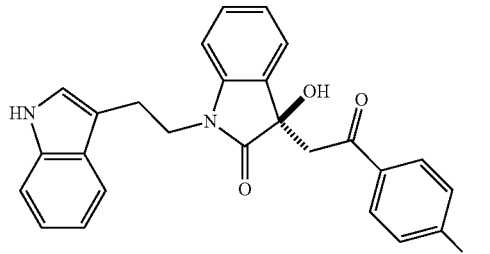
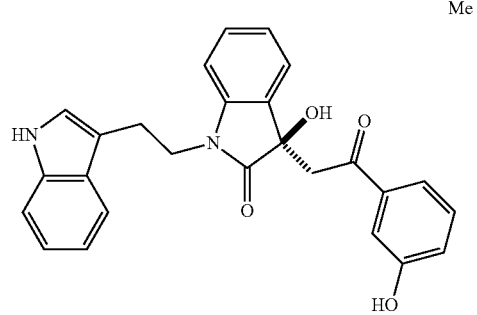
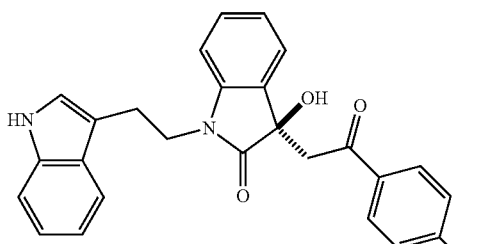
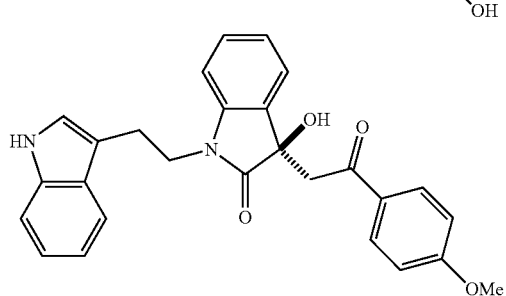
16
-continued
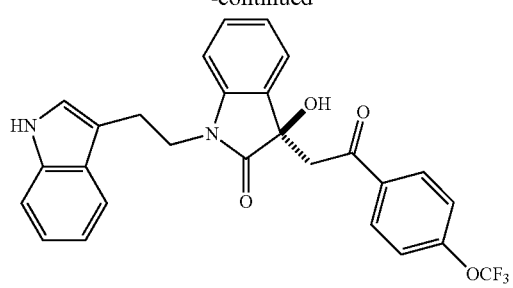
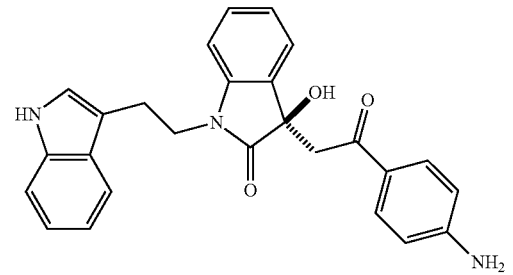
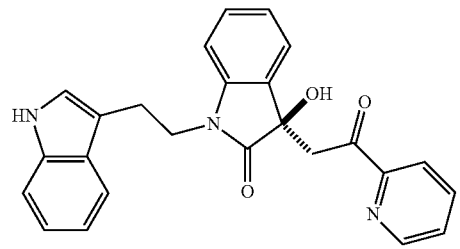
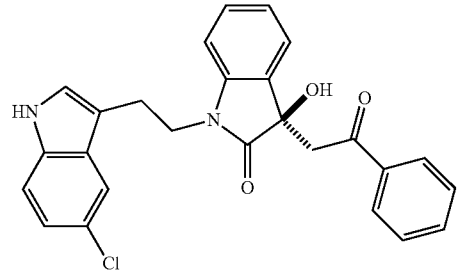
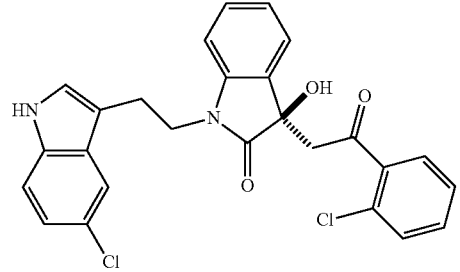
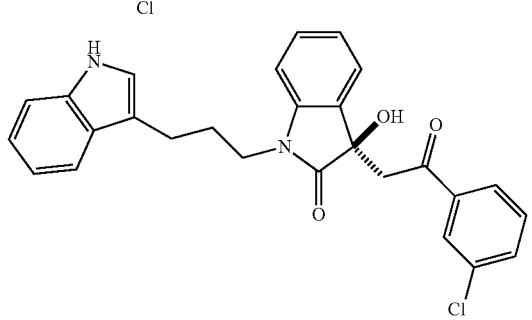

-continued
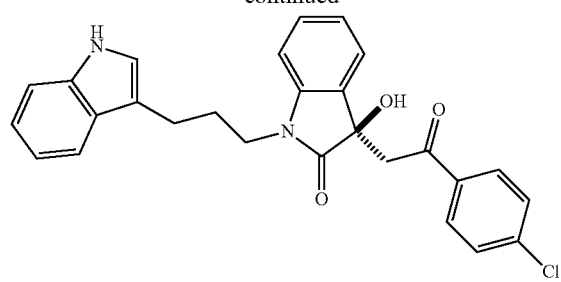
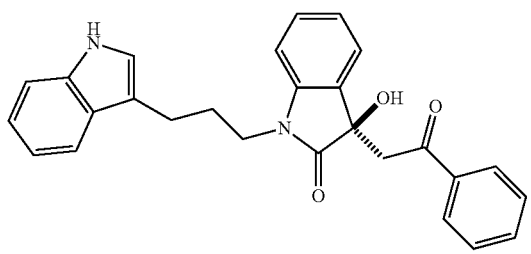
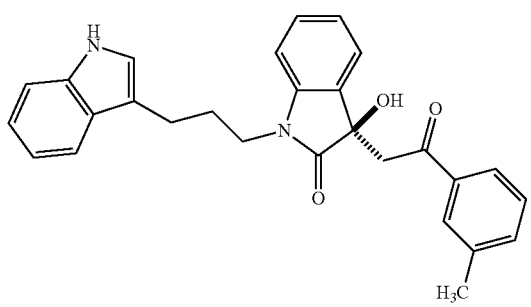
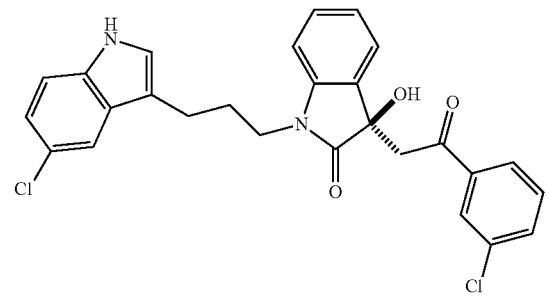
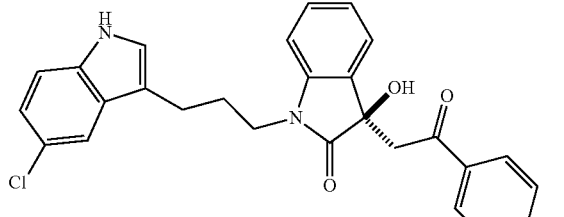
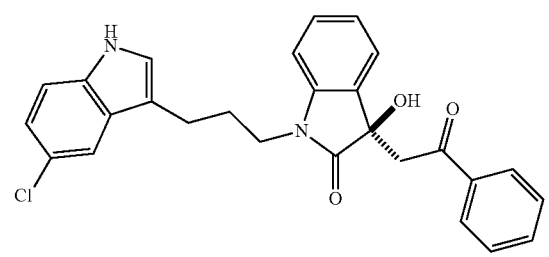
-continued
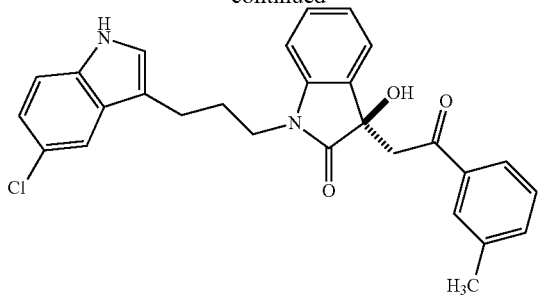
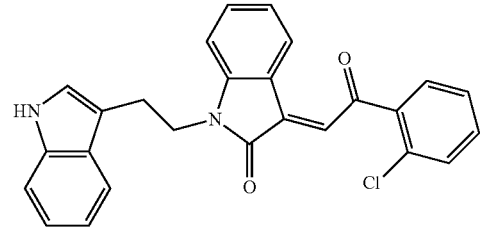
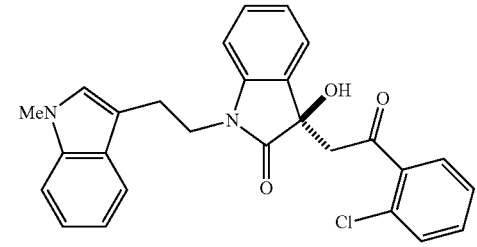
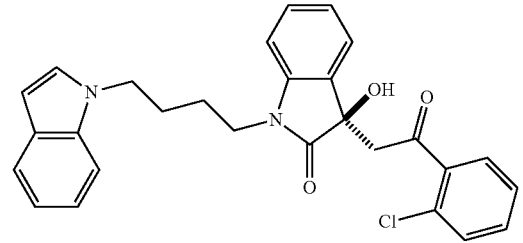
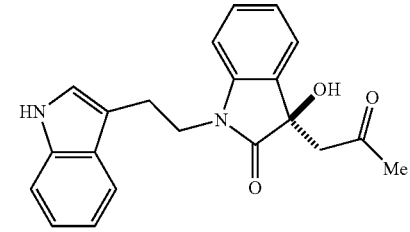
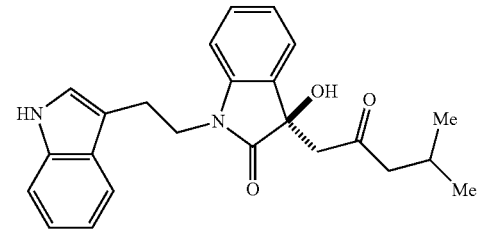
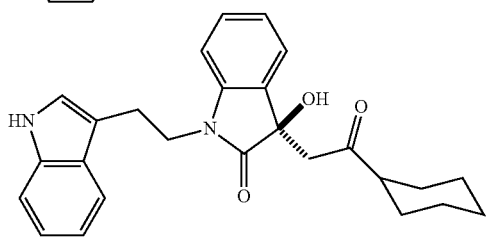

-continued

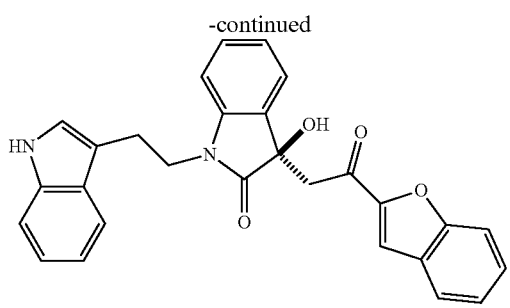

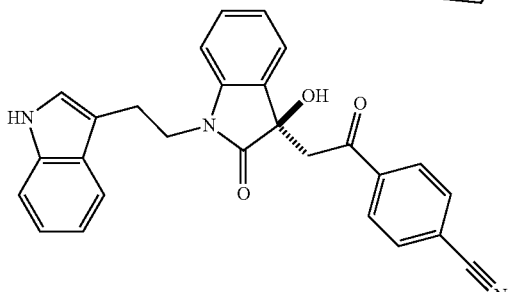

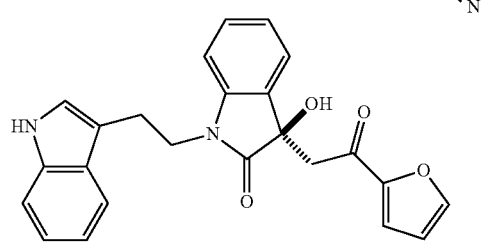

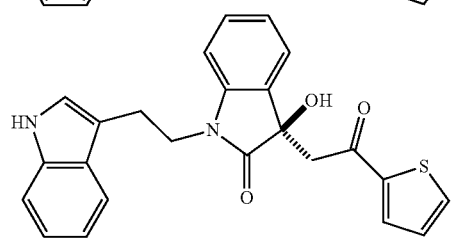

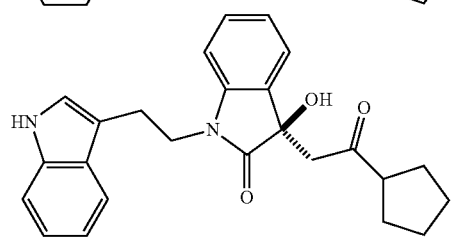

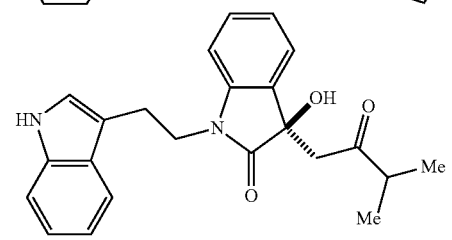

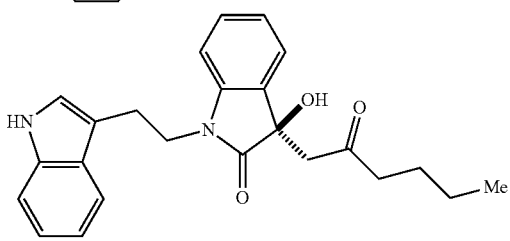

-continued

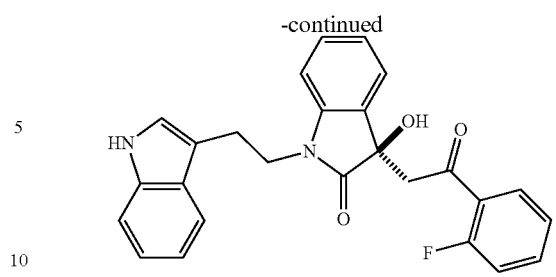

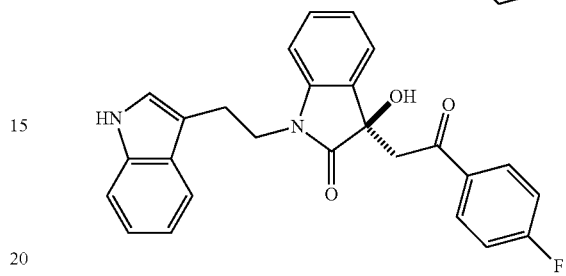

When it is used to characterize the compounds according to the invention, the term "isolated" denotes compounds which are (i) separated from at least one compound with which they are associated in nature, and/or (ii) produced, prepared or manufactured by human means.

Compounds according to the invention may comprise one or more asymmetric centers and may thus exist in various isomeric forms, for example enantiomers and/or diastereoisomers. Thus, the compounds according to the invention and pharmaceutical compositions thereof may be in the form of an individual enantiomer, diastereoisomer or geometrical isomer, or may be in the form of a mixture of stereoisomers. Advantageously, the compounds according to the invention may be enantiomerically pure compounds. Alternatively, the compounds according to the invention may be in the form of stereoisomeric or diastereoisomeric mixtures.

In addition, unless otherwise mentioned, compounds as described in the present document may have one or more double bonds which may exist in the form of Z or E isomers. The invention also covers the compounds as described in the present document, in the form of individual isomers essentially free of other isomers and, alternatively, in the form of mixtures of various isomers, for example racemic mixtures of stereoisomers. In addition to the compounds mentioned above per se, the present invention also covers pharmaceutically acceptable derivatives of these compounds and compositions comprising one or more compounds according to the invention and one or more pharmaceutically acceptable excipients or additives. The compounds according to the invention may be prepared by crystallization of a compound of formula (I) or any of the subformulae described in the present invention. These compounds may exist in the form of a single polymorph or a combination of polymorphs of the compound of general formula (I) forming part of the present invention. For example, different polymorphs may be identified and/or prepared by using different solvents or different mixtures of solvents for the recrystallization; by performing the crystallization at different temperatures; or by using different cooling methods, ranging from very rapid to very slow cooling during the crystallization. The polymorphs may also be obtained by heating or melting of the compound, followed by gradual or rapid cooling. The presence of polymorphs may be determined by solid NMR spectroscopy, IR spectroscopy, differential scanning calorimetry, X-ray diffractometry and/or other suitable techniques. Thus, the present invention covers the compounds according to the invention, derivatives thereof, tautomeric forms thereof, stereoisomers thereof, polymorphs thereof, pharmaceutically acceptable salts thereof, pharmaceutically acceptable solvated forms thereof and pharmaceutically acceptable compositions containing same.

2) General Synthetic Strategies

A person skilled in the art has available abundant indole chemistry literature which he can make use of, in combination with the information contained in the present document, for guidance regarding the synthetic strategies, the protecting groups and other materials and methods that are useful for synthesizing the compounds of this invention, including the compounds containing the various substituents $R_1$, $R_2$, $R_3$, $R_4$, $R_5$ and $R_6$.

The various patent documents and other references cited in the present document give useful general information regarding the preparation of compounds similar to the compounds according to the invention described in the present document, or relevant intermediates.

Furthermore, a person skilled in the art can refer to the teaching and to the specific examples provided in the present document, relating to various examples of compounds and intermediates thereof, for working the present invention in its entire scope.

As described above, the present invention relates to novel compounds, specifically compounds having the following general structure:

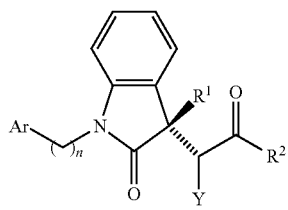

(I)

in which $R_1$, $R_2$, Ar, n and Y are as defined above.

According to another aspect of the invention, processes for preparing the compounds of formula (I) are provided, embodiments of these processes being generally represented in schemes 1 or 2 below, scheme 2 corresponding to scheme 1 complemented with a dehydration and reduction reaction of the olefin:

Scheme 1

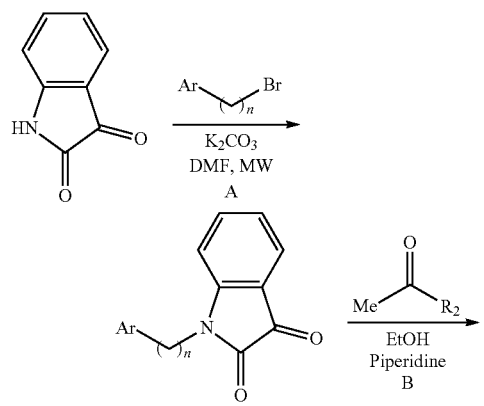

-continued

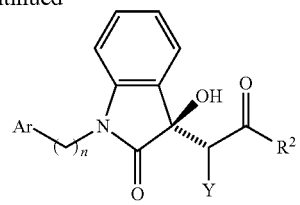

For example, steps A and B may be performed according to the process described, respectively, in Nguyen Dinh Thanh; Nguyen Thi Kim Giang "Reaction of N-alkylisatins with 4-(2,3,4,6-tetra-O-acetyl-β-D-glucopyranosyl)thiosemicarbazide" Hindawi Publishing Corporation Journal of Chemistry 2013, and López-Alvarado, P.; Avendaño, C. "New Diastereoselective Synthesis of 3-Alkylidene-1-methyloxindoles" Synthesis, 2002, 1, 104-110.

Scheme 2

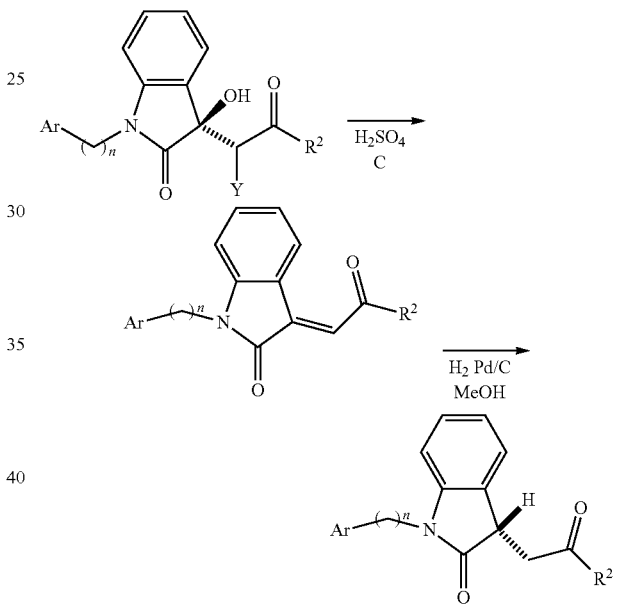

For example, step C may be performed according to the process described in the document Nagle, A. A.; Reddy, S. A.; Bertrand, H.; Tajima, H.; Dang, T.-M.; Wong, S.-C.; Hayes, J. D.; Wells, G.; Chew, E.-H. "3-(2-Oxoethylidene)indolin-2-one Derivatives Activate Nrf2 and Inhibit NF-kB: Potential Candidates for Chemoprevention" ChemMedChem 2014, 9, 1763-1774.

For example, when the group Ar is an indole, the compounds according to the invention may be prepared according to scheme 3A, 3B or 3C below:

Scheme 3A

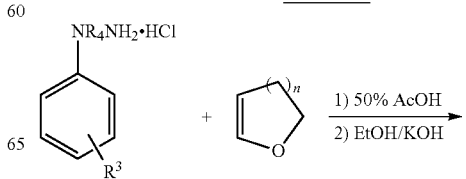

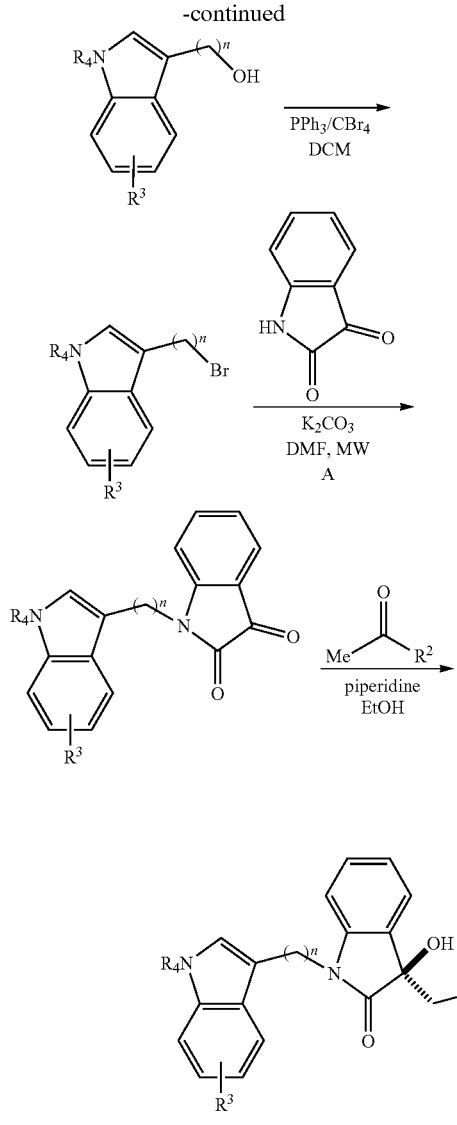
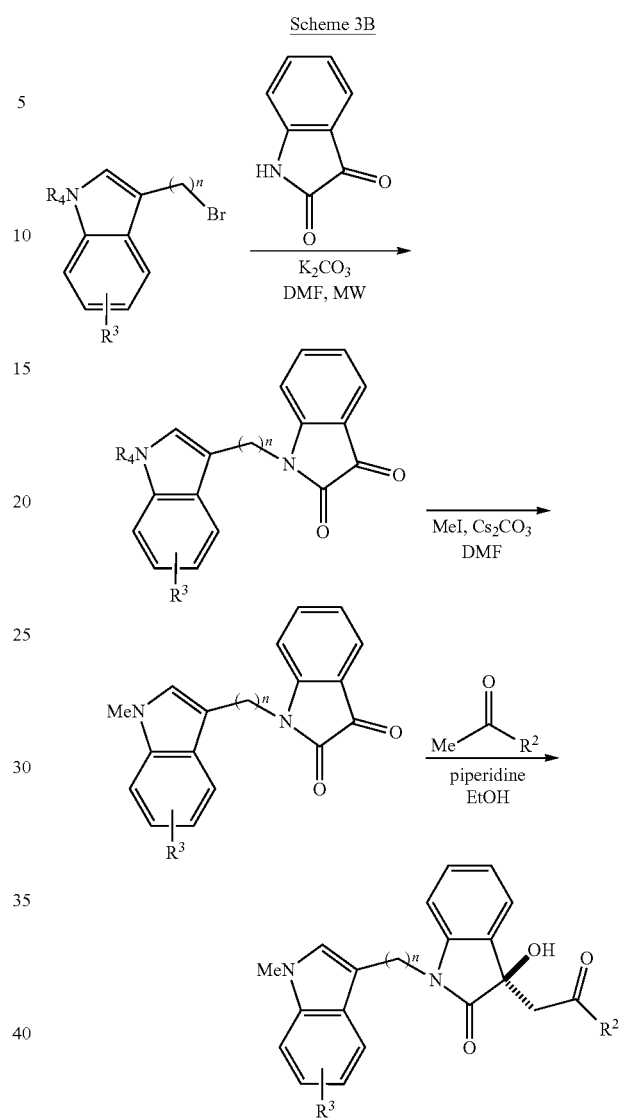
Scheme 3C
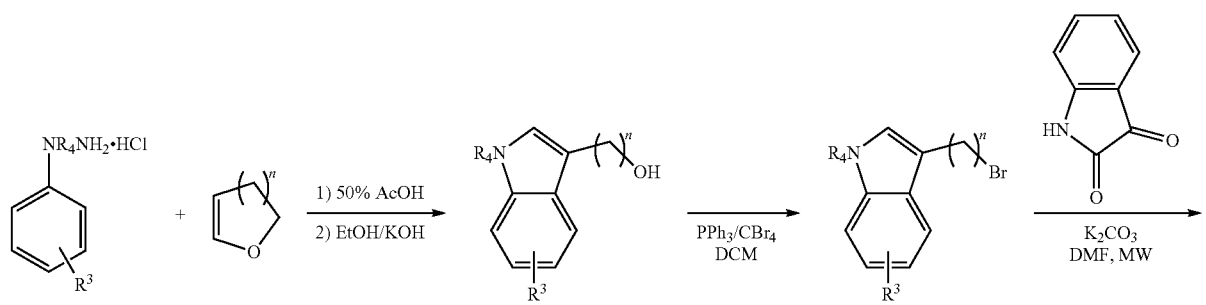

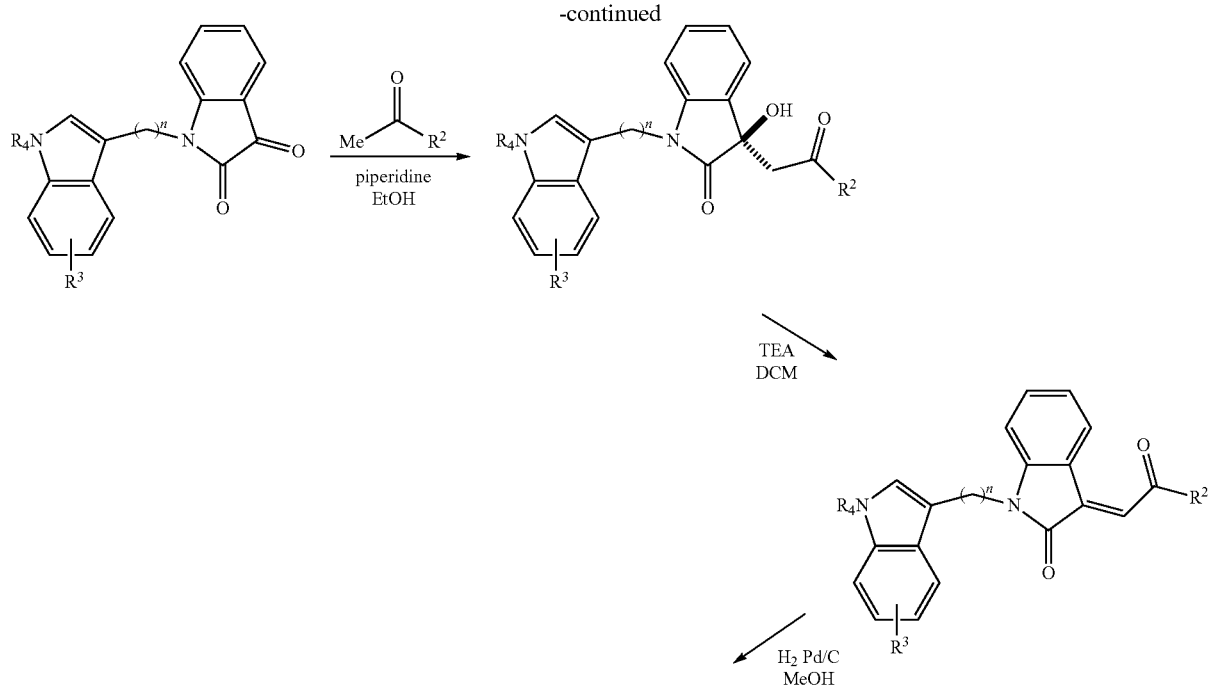
For example, when the group Ar is a group of formula
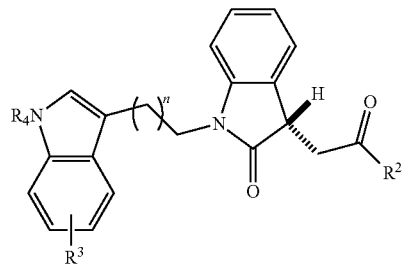
the compounds according to the invention may be prepared according to scheme 4 below:
Scheme 4
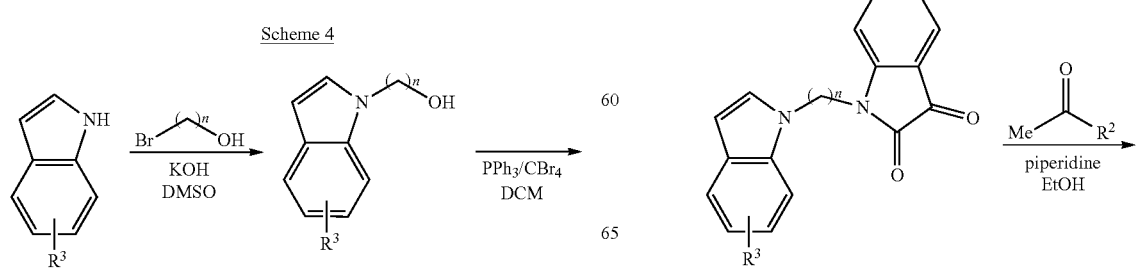
-continued
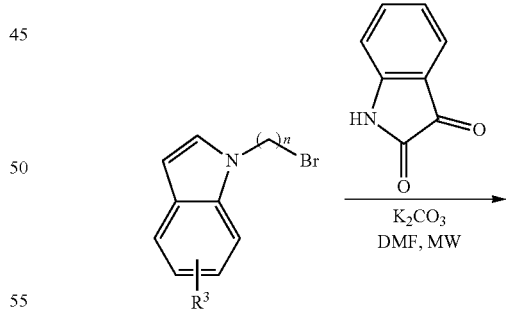

-continued
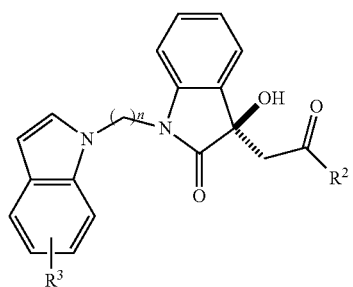
For example, when the group Ar is a group of formula
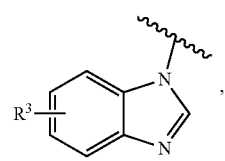
the compounds according to the invention may be prepared according to scheme 6 below:
Scheme 6
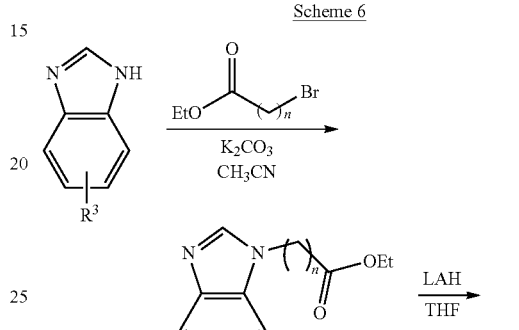
For example, when the group Ar is a group of formula
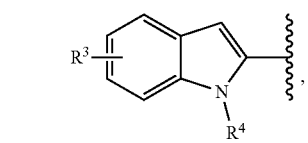
the compounds according to the invention may be prepared according to scheme 5 below:
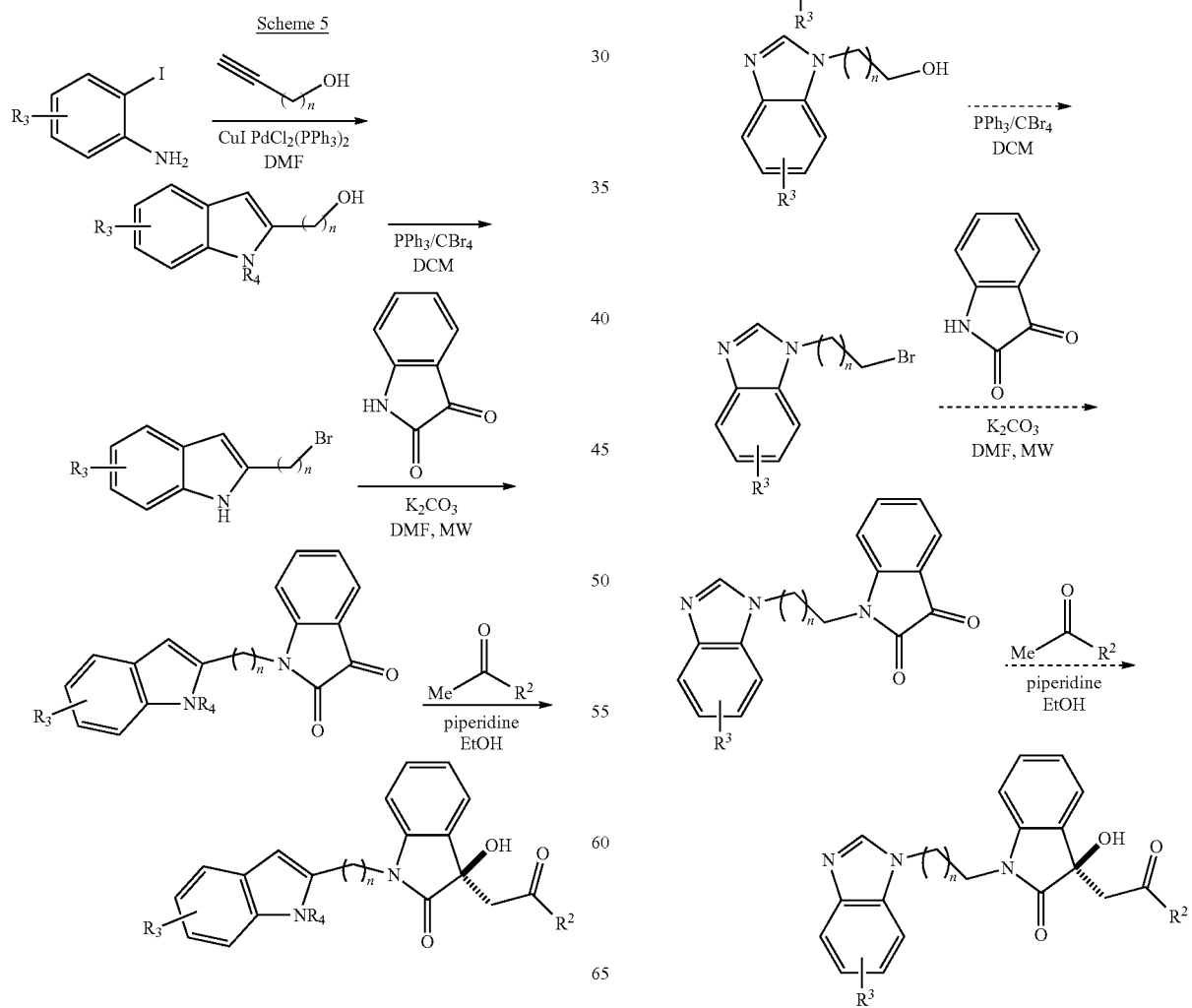

For example, when the group Ar is a group of formula
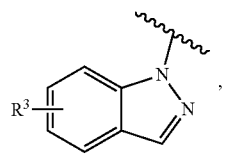
the compounds according to the invention may be prepared according to scheme 7 below:
Scheme 7
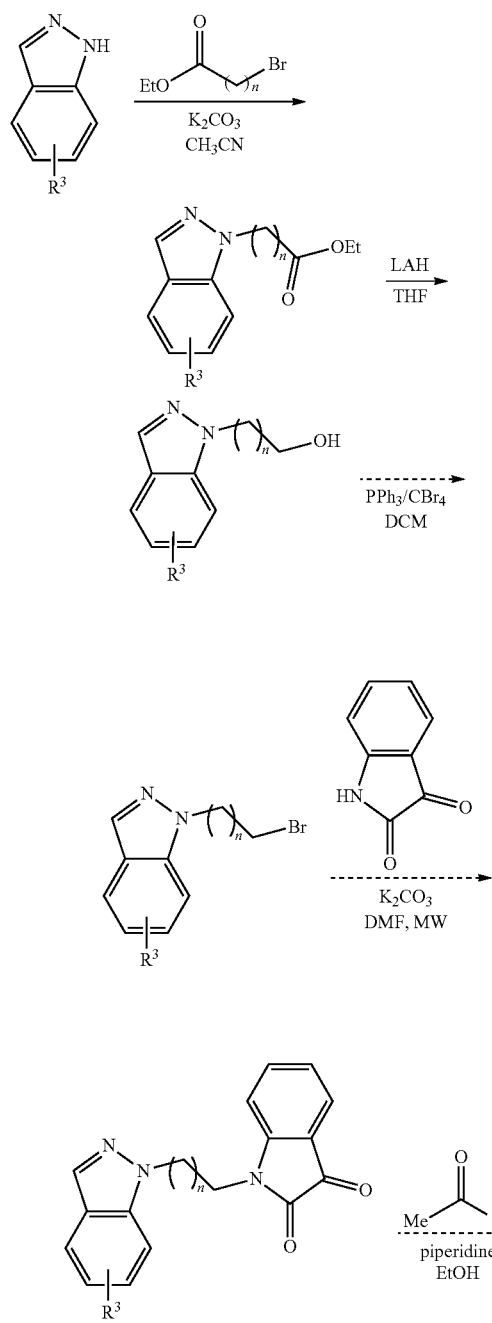
-continued
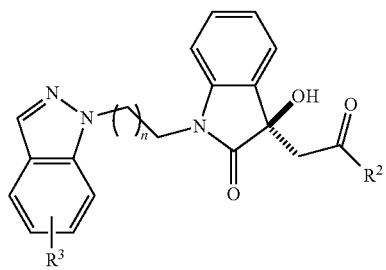
For example, when the group Ar is a group of formula
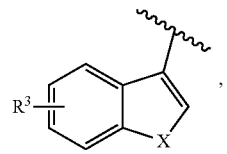
the compounds according to the invention may be prepared, when X represents O, according to scheme 8 below:
Scheme 8
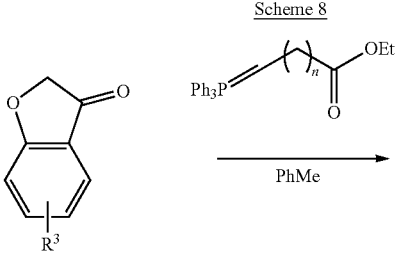
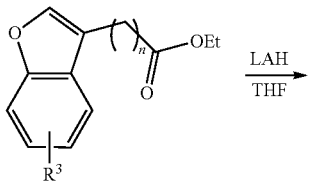
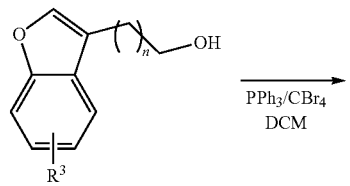
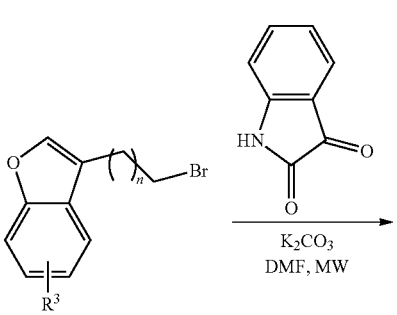

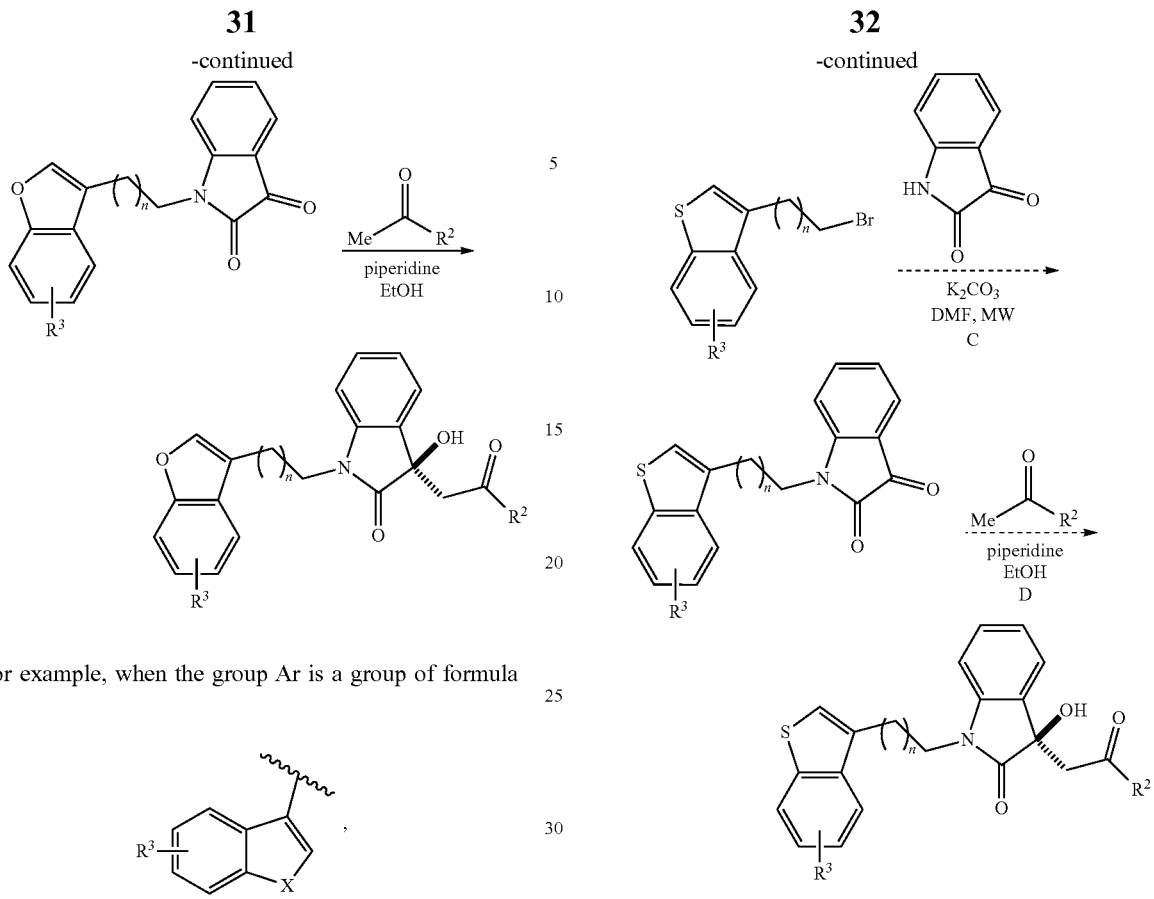
For example, when the group Ar is a group of formula
the compounds according to the invention may be prepared, when X represents S, according to scheme 9 below:
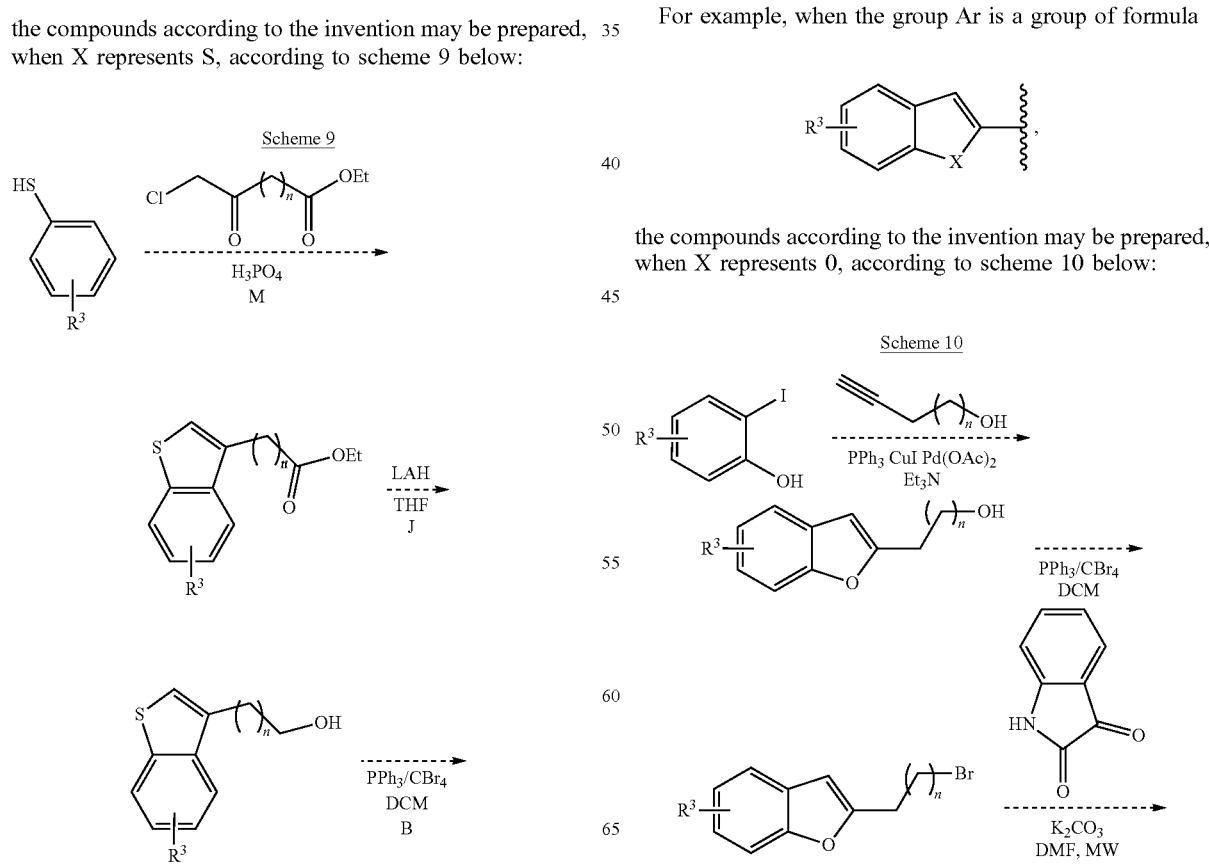
For example, when the group Ar is a group of formula
the compounds according to the invention may be prepared, when X represents O, according to scheme 10 below:

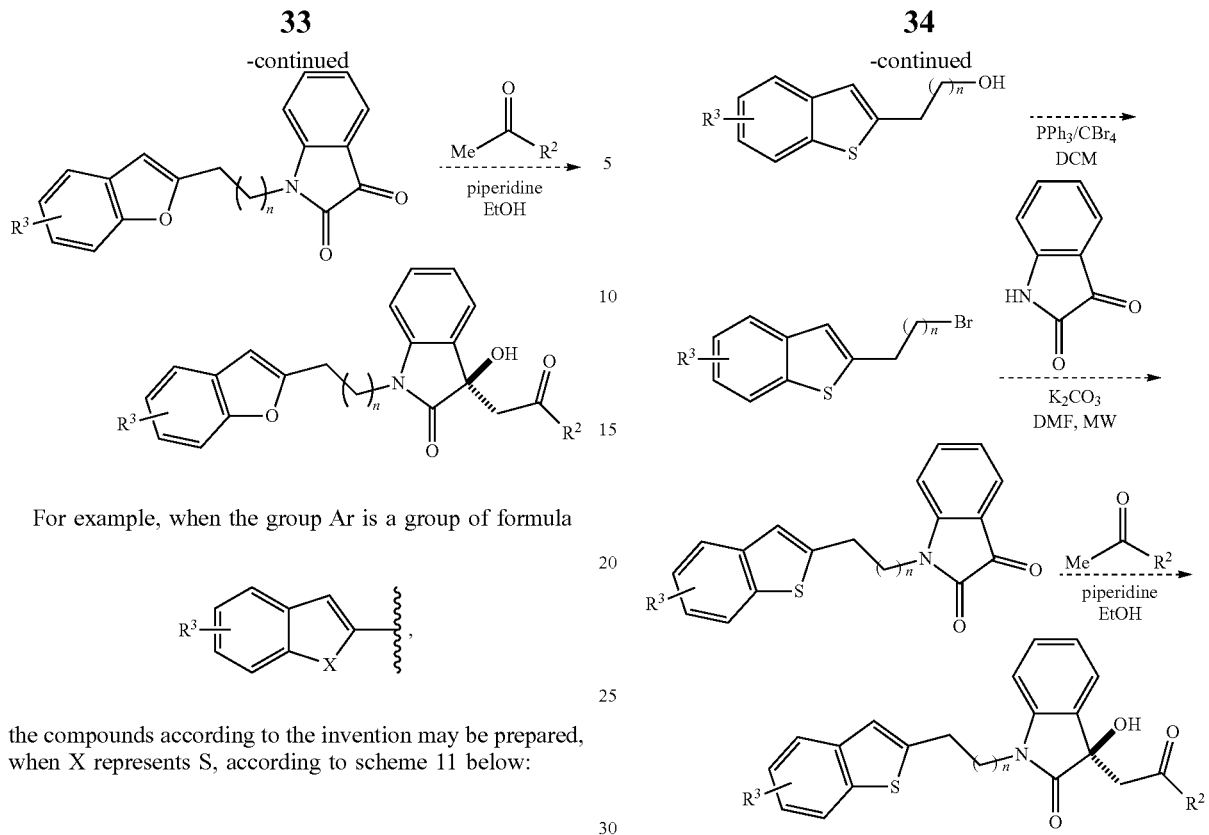

For example, when the group Ar is a group of formula the compounds according to the invention may be prepared, when X represents S, according to scheme 11 below:

The preceding synthons, and the homologs thereof, may be prepared via methods known in the art. For example, the reader may refer to the publications listed in the following table:

| Synthons | References |
|---|---|
|  | "Approach for the synthesis of indole-3-propanol and its acetates from dihydropyran" Monatsh. Chem. 2008, 139, 1475-1478. |
|  | Campos, K. R.; Woo, J. C. S.; Lee.; Tillyer, R. D. "A General Synthesis of Substituted Indoles from Cyclic Enol Ethers and Enol Lactones" Org. Lett. 2004, 6, 79-82. |
|  | Yang, J. -M.; Li, P. -H.; Wei, Y.; Tang, X. -Y.; Shi, M. "Gold(I)-catalyzed highly stereoselective synthesis of polycyclic indolines: The construction of four contiguous stereocenters" Chem. Commun. 2016, 52, 346-349. Kounosuke, O.; Abe, J.; Kanai, M. "Manganese-catalyzed aerobic dehydrogenative cyclization toward ring-fused indole skeletons" Org. Biomol. Chem. 2013, 11, 4569-4572. |

-continued

| Synthons | References |
|---|---|
| 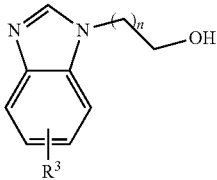 | Campaigne, E.; Homfeld, E. "Benzo[b]thiophene derivatives. XXV.Condensation and reductive alkylation of 3-aminoalkylbenzo[b]thiophenes with formaldehyde" J. Heterocycl. Chem. 1979, 16, 1321-1324. |
| 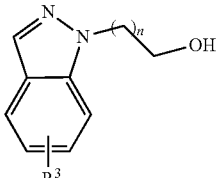 | Zhang, H. C.; Ye, H.; Moretto, A. F.; Brumfield, K. K.; Maryanoff, B. E. "Facile Solid-Phase Construction of Indole Derivatives Based on a Traceless, Activating Sulfonyl Linker" Org. Lett. 2000, 2, 89-92. |
| 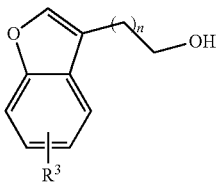 | Lee, S. S.; Shen, W.; Zheng, X.; Jacobsen, I. C. "Preparation of tetrahydropyridinylthiophenecarboxylic acid derivatives for use as hepatitis C virus polymerase inhibitors" WO2014055142 A1.<br>Caroff, E.; Keller, M.; Kimmerlin, T.; Meyer, E.; "Preparation of 4-(benzoimidazol-2-yl)thiazole compounds and related aza derivatives as modulators of the CXCR3 receptor" WO2013114332 A1.<br><br>Kruegel, A. C.; Rakshit, S.; Li, X.; Sames, D.; "Constructing Iboga Alkaloids via C—H Bond Functionalization: Examination of the Direct and Catalytic Union of Heteroarenes and Isoquinuclidine Alkenes" J. Org. Chem. 2015, 80, 2062-2071. |
| 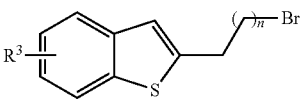 | Van Epps, D. E.; Jiang, G. -L.; Collette, A. G.; Horan, R. L.; Chen, J. S.; Altman, G. H.; Im, W. -B. "Compositions and improved soft tissue replacement method" WO2013123272 A1.<br><br>Contour-Galcéra, M. -O.; Sidhu, A.; Plas, P.; Roubert, P. "3-Thio-1,2,4-triazoles, novel somatostatin sst2/sst5 agonists" Bioorg. Med. Chem. Lett. 2005, 15, 3555-3559. |
| 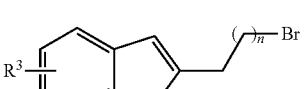 | Rong, Z.; Wang, W.; Jiang, Z. J.; Wang, K.; Zheng, X. -L.; Fu, H. -Y.; Chen, H.; Li, R. -X. "One-pot synthesis of 2-substituted benzo[b]furans via Pd-tetraphosphine-catalyzed coupling of 2-halophenols with alkynes" Chem. Commun. 2014, 50, 6023-6026.<br><br>Banerjee, T. S.; Paul, S.; Sinha, S.; Das, S. "Synthesis of iboga-like isoquinuclidines: Dual opioid receptor agonists having antinociceptive properties" Bioorg. Med. Chem. 2014, 22, 6062-6070. |
| 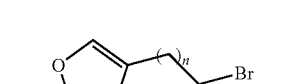 | Kruegel, A. C.; Rakshit, S.; Li, X.; Sames, D.; "Constructing Iboga Alkaloids via C—H Bond Functionalization: Examination of the Direct and Catalytic Union of Heteroarenes and Isoquinuclidine Alkenes" J. Org. Chem. 2015, 80, 2062-2071.<br>Contour-Galcéra, M. -O.; Sidhu, A.; Plas, P.; Roubert, P. "3-Thio-1,2,4-triazoles, novel somatostatin sst2/sst5 agonists" Bioorg. Med. Chem. Lett. 2005, 15, 3555-3559.<br><br>Campaigne, E.; Homfeld, E. "Benzo[b]thiophene derivatives. XXV.Condensation and reductive alkylation of 3-aminoalkylbenzo[b]thiophenes with formaldehyde" J. Heterocycl. Chem. 1979, 16, 1321-1324. |

| Synthons | References |
|---|---|
| 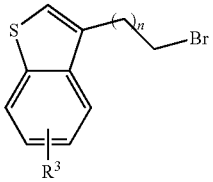 | Zhang, H. C.; Ye, H.; Moretto, A. F.; Brumfield, K. K.; Maryanoff, B. E. "Facile Solid-Phase Construction of Indole Derivatives Based on a Traceless, Activating Sulfonyl Linker" Org. Lett. 2000, 2, 89-92. Contour-Galcéra, M. -O.; Sidhu, A.; Plas, P.; Roubert, P. "3-Thio-1,2,4-triazoles, novel somatostain sst2/sst5 agonists" Bioorg. Med. Chem. Lett. 2005, 15, 3555-3559. |

3) Compositions and Uses

As indicated previously, the present invention provides NMDA receptor-modulating compounds and, consequently, the present compounds are useful for the treatment of diseases, disorders and pathologies involving these central nervous system receptors, including, but without being limited to, severe/resistant epilepsy and cognitive disorders resulting therefrom, notably autism, but also strokes, schizophrenia, degenerative diseases involving activation of the NMDA receptors such as Parkinson's disease and Alzheimer's disease, Rett's syndrome or amyotrophic lateral sclerosis, migraine, dementia and major depression. Consequently, according to another aspect of the present invention, pharmaceutically acceptable compositions are provided, which comprise any of the compounds as described previously, and optionally comprise a pharmaceutically acceptable support, an adjuvant or a vehicle. Advantageously, these compositions may also optionally comprise one or more additional therapeutic agents, notably those known and used in particular for treating severe/resistant epilepsy and cognitive disorders resulting therefrom, notably autism, but also strokes, schizophrenia, degenerative diseases involving activation of the NMDA receptors such as Parkinson's disease and Alzheimer's disease, Rett's syndrome or amyotrophic lateral sclerosis, migraine, dementia and major depression.

In the present invention, the term "pharmaceutically acceptable salt" denotes salts that are suitable for human or veterinary pharmaceutical use without toxicity, irritation, allergic response or other deleterious effect unsuitable for medicinal use and have a reasonable benefit/risk ratio. A "pharmaceutically acceptable salt" denotes any nontoxic salt or a salt of an ester of a compound of the present invention, which, after administration to an individual, is capable of providing, directly or indirectly, a compound of the present invention or a metabolite or a residue thereof, which modulates the NMDA receptors. As used herein, the term "metabolite or a residue thereof, which modulates the NMDA receptors" means that a metabolite or residue thereof is also an NMDA receptor modulator, like the compounds of the present invention.

Pharmaceutically acceptable salts are well known in the medical field. For example, S. M. Berge et al. describe pharmaceutically acceptable salts in detail in J. Pharmaceutical Sciences, 1977, 66, 1-19, which is incorporated into the present document by reference. The pharmaceutically acceptable salts of the compounds of the present invention comprise those derived from suitable inorganic and organic acids and bases. Examples of nontoxic pharmaceutically acceptable addition salts comprise salts of an amino group formed with inorganic acids such as hydrochloric acid, hydrobromic acid, phosphoric acid or sulfuric acid, or with organic acids such as acetic acid, oxalic acid, maleic acid, tartaric acid, citric acid, succinic acid or maleic acid, or using other processes used in the art such as ion exchange.

Other pharmaceutically acceptable salts comprise adipate, alginate, ascorbate, aspartate, benzenesulfonate, benzoate, bisulfate, borate, butyrate, camphorate, camphorsulfonate, citrate, cyclopentylpropionate, gluconate, dodecylsulfate, ethanesulfonate, formate, fumarate, glucoheptonate, glycerophosphate, gluconate, hemisulfate, heptanoate, hexanoate, hydriodide, 2-hydroxyethanesulfonate, lactobionate, lactate, laurate, laurylsulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, p-toluenesulfonate, undecanoate, valerate and the like. The suitable salts derived from bases comprise salts of alkali metals, of alkaline-earth metals, of ammonium and quaternary ammonium salts $N^+(C_{1-4}\ alkyl)_4$. The present invention also envisages the quaternization of all the groups containing a basic nitrogen of the compounds disclosed in the present specification. Products that are soluble or dispersible in water or an oily medium may be obtained via such a quaternization. Salts of representative alkali metals or alkaline-earth metals comprise those of sodium, lithium, potassium, calcium, magnesium, and the like. Other nontoxic pharmaceutically acceptable salts comprise, where appropriate, ammonium salts, quaternary ammonium salts and salts of amine cations formed using counterions such as a halide, a hydroxide, a carboxylate, a sulfate, a phosphate, a nitrate, a lower alkyl sulfonate and arylsulfonate.

As described above, the pharmaceutically acceptable compositions of the present invention also comprise a pharmaceutically acceptable support, an adjuvant or a vehicle, which, as defined in the present document, includes any solvent, diluent or other liquid vehicle, dispersion or suspension aid, surfactant, isotonic agent, thickener or emulsifier, preserving agent, solid binder, lubricant and the like, which are suitable for the particular desired dosage form. Remington Pharmaceutical Sciences, sixteenth edition, E. W. Martin (Mack Publishing Co., Easton, Pa., 1980) describes various supports used in the formulation of pharmaceutically acceptable compositions and known techniques for preparing same. Except in the case where a conventional support medium proves to be incompatible with the compounds according to the invention, for example by producing any undesirable biological effect or else by deleteriously interacting with any other component(s) of the pharmaceutically acceptable composition, its use is envisaged as falling within the context of the present invention. A few examples of materials that can serve as pharmaceutically acceptable support comprise, but are not limited to, ion exchangers, alumina, aluminum stearate, lecithin, serum proteins such as human serum albumin, buffer substances such as phosphates, glycine, sorbic acid, or potassium sorbate, mixtures of partial glycerides of saturated plant fatty acids, water, salts or electrolytes such as protamine sulfate, disodium phosphate, potassium hydrogen phosphate, sodium chloride, zinc salts, colloidal silica, magnesium trisilicate, polyvinylpyrrolidone, polyacrylates, waxes, polyethylene-polyoxypropylene polymers, sugars such as lactose, glucose and sucrose; starches such as corn starch and potato starch; cellulose and derivatives thereof such as sodium carboxymethylcellulose, ethylcellulose and cellulose acetate; tragacanth powder; malt; gelatin; talc; excipients such as cocoa butter and waxes for suppositories; oils such as groundnut oil, cottonseed oil; safflower oil; sesame oil; olive oil; corn oil and soybean oil; glycols such as propylene glycol or polyethylene glycol; esters such as ethyl oleate and ethyl laurate; agar; agents such as magnesium hydroxide and aluminum hydroxide as buffer; alginic acid; an isotonic saline solution; Ringer's solution; ethyl alcohol, and phosphate buffer solutions, and also other compatible nontoxic lubricants such as sodium lauryl sulfate and magnesium stearate, and also colorants, mold-release agents, coating agents, sweeteners, flavorings and fragrances, preserving agents and antioxidants may also be present in the composition, according to the judgement of the galenical formulator.

According to another aspect, the present invention relates to any of the compounds as described previously, or a pharmaceutical composition comprising same, for its use as a medicament, notably in the treatment of diseases or conditions involving an N-methyl-D-aspartate receptor of the central nervous system, such as severe/resistant epilepsy and cognitive disorders resulting therefrom, notably autism, but also strokes, schizophrenia, degenerative diseases involving activation of the NMDA receptors such as Parkinson's disease and Alzheimer's disease, Rett's syndrome or amyotrophic lateral sclerosis, migraine, dementia and major depression.

According to another aspect, the present invention relates to a method for treating or preventing diseases or pathologies involving an N-methyl-D-aspartate receptor of the central nervous system, such as severe/resistant epilepsy and cognitive disorders resulting therefrom, notably autism, but also strokes, schizophrenia, degenerative diseases involving activation of the NMDA receptors such as Parkinson's disease and Alzheimer's disease, Rett's syndrome or amyotrophic lateral sclerosis, migraine, dementia and major depression, comprising the administration of an effective amount of a compound or of a pharmaceutically acceptable composition according to the present invention, to an individual.

In the present document, an "effective amount" of a compound or of a pharmaceutically acceptable composition according to the invention refers to an amount that is effective for treating or reducing the severity of a disease or condition associated with the NMDA receptors. The compounds and compositions, according to the treatment method of the present invention, may be administered using any amount and any administration route that is effective for treating or reducing the severity of a disease or condition associated with the NMDA receptors. The exact amount required will vary from one individual to another, as a function of the species, the age and the general condition of the individual, the severity of the infection, the particular compound and the method for administering same.

The compounds according to the invention are preferably formulated in a unit dosage form to facilitate the administration and the uniformity of the dosage. In the present document, the term "unit dosage form" refers to a physically distinct unit of compound that is suitable for the patient to be treated. However, it will be understood that the total daily dosage of the compounds and compositions according to the present invention will be decided by the treating medical physician. The specific effective dose level for a particular animal or human patient or individual will depend on a variety of factors comprising the disorder or disease treated and the severity of the disorder or disease; the activity of the specific compound used; the specific composition used; the age, body weight, general health, sex and diet of the patient/individual; the period of administration, the administration route and the rate of elimination of the specific compound used; the duration of the treatment; the medicaments used in combination or incidentally with the specific compound used and analogous factors that are well known in the medical arts. As used herein, the term "patient" denotes an animal, preferably a mammal, and preferably a human being.

The pharmaceutically acceptable compositions of the present invention may be administered to humans and other animals via the oral, rectal, parenteral, intracisternal, intravaginal, intraperitoneal or topical route (for instance via powders, salves or drops), the oral route, in oral or nasal spray form, or the like, according to the severity of the infection to be treated. For example, the compounds according to the invention may be administered orally or parenterally at doses from approximately 0.01 mg/kg to approximately 50 mg/kg and preferably from approximately 1 mg/kg to approximately 25 mg/kg of body weight of the individual per day, one or more times per day, to obtain the desired therapeutic effect.

The liquid galenical forms for oral administration comprise, without being limited thereto, pharmaceutically acceptable emulsions, microemulsions, solutions, suspensions, syrups and elixirs. In addition to the active compounds, the liquid galenical forms may contain inert diluents commonly used in the art, for instance water or other solvents, agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed oil, groundnut oil, corn germ oil, olive oil and sesame oil), glycerol, tetrahydrofurfuryl alcohol, polyethylene glycols and fatty acid esters of sorbitan and mixtures thereof. Besides the inert diluents, the oral compositions may also comprise adjuvants such as wetting agents, emulsifiers and suspension agents, sweeteners, flavorings and fragrancing agents.

The solid galenical forms for oral administration comprise capsules, tablets, pills, powders and granules. In such solid galenical forms, the active compound is mixed with at least one inert support, excipient or pharmaceutically acceptable support such as sodium citrate or dicalcium phosphate and/or a) fillers or diluents such as starches, lactose, sucrose, glucose, mannitol and silicic acid, b) binders, for instance carboxymethylcellulose, alginate, gelaten, polyvinylpyrrolidone, sucrose and gum arabic, c) wetting agents such as glycerol, d) disintegrating agents such as agar-agar, calcium carbonate, potato starch or cassava starch, alginic acid, certain silicates and sodium carbonate, e) absorption accelerators such as quaternary ammonium compounds, f) wetting agents, for instance cetyl alcohol and glyceryl monostearate, g) absorbents such as kaolin and bentonite clay, and h) lubricants such as talc, calcium stearate, magnesium stearate, solid polyethylene glycols, sodium lauryl sulfate, and mixtures thereof. In the case of capsules, tablets and pills, the galenical form may also comprise buffer agents.

Solid compositions of a similar type may also be used as fillers in soft or hard gelatin capsules, using excipients such as lactose or milk sugar and also polyethylene glycols with a high polyethylene molecular weight, and the like. The solid galenical forms of plain tablets, coated tablets, gel capsules, pills and granules may be prepared with coatings and envelopes such as enteric coatings and other coatings that are well known in the art of pharmaceutical formulation. They may optionally contain opacifiers and may also have a composition such that they release the active ingredient(s) only, or preferentially, in a certain part of the digestive tract, optionally in a delayed manner. Examples of coating compositions that may be used comprise polymeric substances and waxes. Solid compositions of a similar type may also be used as fillers in soft and hard gelatin capsules, using excipients such as lactose or milk sugar and also polyethylene glycols with a high polyethylene molecular weight, and the like.

The compounds and the pharmaceutically acceptable compositions of the present invention may also be used in combined therapies, i.e. the compounds and the pharmaceutically acceptable compositions may be administered simultaneously with, before or after one or more other therapeutic agents, or medical procedures. The particular combination of therapies (therapies or procedures) to be used in a combination scheme will take into account the compatibility of the desired therapeutic products and/or of the procedures and the desired therapeutic effect to be achieved. The therapies used may target the same disease (for example, a compound according to the invention may be administered simultaneously with another agent used for treating the same disease), or they may target different therapeutic effects (for example controlling adverse effects).

For example, therapeutic agents known for treating diseases, disorders and conditions involving these central nervous system receptors and including, but without being limited to, severe/resistant epilepsy, schizophrenia, Parkinson's disease, Alzheimer's disease, dementia or major depression may be combined with the compounds of the present invention to treat these same diseases. Examples of therapies or therapeutic agents that may be used in combination with the compounds of the present invention in particular comprise severe/resistant epilepsy and cognitive disorders resulting therefrom, notably autism, but also strokes, schizophrenia, degenerative diseases involving activation of the NMDA receptors such as Parkinson's disease and Alzheimer's disease, Rett's syndrome or amyotrophic lateral sclerosis, migraine, dementia and major depression.

Kits of Parts

The present invention also relates to a kit for performing and implementing the treatment methods in accordance with the present invention. In general, the pharmaceutical pack or kit comprises one or more containers filled with one or more of the ingredients of the pharmaceutical compositions according to the invention. Such kits are particularly suitable for the administration of solid oral forms such as tablets or capsules. Such a kit preferably comprises a certain number of unit doses, and may also include a tray on which the dosage units are arranged in the recommended order of their use. If so desired, a memory aid may be provided, for example in the form of figures, letters or other markings or with a calendar insert, denoting the days in the treatment program in which the doses may be administered. Alternatively, the placebo doses or dietary calcium supplements, whether in a form similar to or different from the dosages of the pharmaceutical compositions, may be included to provide a kit in which a dose is taken every day. The kit may also comprise an explanatory notice, notably comprising information relating to the form prescribed by a governmental agency regulating the manufacture, use or sale of pharmaceutical products.

EQUIVALENTS

The representative examples that follow are intended to illustrate the invention and are not intended to limit the scope of the invention, nor should they be interpreted in this way. Indeed, various modifications of the invention and of numerous other embodiments thereof, in addition to those presented and described here, will become apparent to a person skilled in the art from the contents of this document as a whole, including the examples that follow.

The examples that follow contain important additional information, for illustration and teaching which may be suitable for working this invention in its various embodiments and the equivalents thereof.

The examples that follow are given as a guide and with no limiting nature on the invention.

Advantages other than those described in the present application may also become apparent to a person skilled in the art on reading the examples below, given as illustrations.

EXAMPLES

Example 1: General Procedure a for the Preparation of 3-(hydroxyalkyl)(1H)indol-3-yl A solution of acetic acid at 50% in water (18 mL) was added to the desired phenylhydrazine hydrochloride (1 equiv., 8.4 mmol) at room temperature, i.e. at 20° C., in a microwave tube of suitable size, under an argon atmosphere. Dihydropyran or dihydrofuran (1 equiv., 8.4 mmol) was added dropwise over 2 minutes to the preceding solution. The flask was sealed and heated at 50° C. for 10 minutes and then at 100° C. for 55 minutes. The reaction mixture was deactivated by adding saturated sodium hydrogen carbonate solution (10 mL). The aqueous phase was extracted three times with ethyl acetate (3×20 mL) and the organic phases were combined and then washed with brine (10 mL), dried over anhydrous magnesium sulfate, filtered through a sinter funnel and concentrated under reduced pressure (50 mbar) on a rotary evaporator. The crude product obtained was then diluted in ethanol (20 mL) and 10 potassium hydroxide pellets were added at room temperature, i.e. at 20° C., and stirred for 2 hours. The reaction mixture was deactivated by adding water (10 mL). The aqueous phase was extracted three times with ethyl acetate (3×20 mL) and the organic phases were combined and then washed with water (3×10 mL) to neutral pH, with brine (10 mL), dried over magnesium sulfate, filtered through a sinter funnel and concentrated under reduced pressure (50 mbar) on a rotary evaporator. Purification was performed by flash column chromatography [25 g, flow rate 18 mL/minute, 100/0 to 50/50 cyclohexane/EtOAc] to give the desired 3-(hydroxyalkyl)(1H)indol-3-yl.

Example 2: General Procedure B for the Preparation of 3-(bromoalkyl)(1H)indol-3-yl Carbon tetrabromide (1.5 equiv., 12.6 mmol) was added to a solution of 3-(2-hydroxyethyl)(1H)indol-3-yl (1 equiv., 8.4 mmol) in anhydrous dichloromethane (150 ml) in a flask of suitable size, under an argon atmosphere at 0° C. Triphenylphosphine (1.5 equiv., 12.6 mmol) was then added in five equal portions over a period of 10 minutes at 0° C. The reaction mixture was stirred at room temperature, i.e. at 20° C., for 1 hour and then evaporated under reduced pressure (50 mbar) on a rotary evaporator. Purification was performed by flash column chromatography as described in Example 1 to give the desired 3-(bromoalkyl)(1H)indol-3-yl.

Example 3: General Procedure C for the Preparation of 1-(3-alkyl(1H)indol-3-yl)indole-2,3-dione Isatin (1 equiv., 3.40 mmol), 3-(2-bromoethyl)(1H)indol-3yl (1.02 equiv., 3.47 mmol) and potassium carbonate (1.4 equiv., 4.76 mmol) were mixed in anhydrous dimethylformamide (15 mL) in a microwave tube of suitable size, under an argon atmosphere. The flask was sealed and irradiated with microwave radiation at 130° C. for 15 minutes. The reaction mixture was deactivated by adding ethyl acetate. The organic phase was washed successively with saturated ammonium chloride solution and then with brine, dried over magnesium sulfate, filtered and concentrated under reduced pressure as described in Example 1. Purification was performed by flash column chromatography as described in Example 1 to give the desired 1-(3-alkyl(1H)indol-3-yl)indole-2,3-dione.

Example 4: General Procedure D for the Preparation of 1-(3-alkyl(1H)indol-3-yl)-3-hydroxy-3-(2-oxo-2-phenylethyl)indol-2-one 1-(3-Ethyl(1H)indol-3-yl)indol-2,3-dione (1 equiv., 0.28 mmol), acetophenone (1.4 equiv., 0.39 mmol) and piperidine (500 μL) were mixed in absolute ethanol (3 ml) in a microwave tube of suitable size, under an argon atmosphere. The flask was sealed and stirred at room temperature, i.e. at 20° C., for 18 hours. The reaction mixture was deactivated by adding ethyl acetate. The organic phase was washed successively with saturated ammonium chloride solution and then with brine, dried over magnesium sulfate, filtered and concentrated under reduced pressure as described in Example 1. Purification was performed by flash column chromatography as described in Example 1 to give the desired 1-(3-alkyl(1H)indol-3-yl)-3-hydroxy-3-(2-oxo-2-phenylethyl)indol-2-one.

Example 5: General Procedure E for the Preparation of 1-(3-alkyl-1-methyl(1H)indol-3-yl)indole-2,3-dione Methyl iodide (1.5 equiv., 0.52 mmol) and cesium carbonate (2 equiv., 0.69 mmol) were added to a solution of 1-(3-ethyl(1H)indol-3-yl)indole-2,3-dione (1 equiv., 0.34 mmol) in anhydrous dimethylformamide (5 ml) in a flask of suitable size, under an argon atmosphere at room temperature. The reaction mixture is stirred at room temperature, i.e. at 20° C., for 3 hours and then deactivated by adding ethyl acetate. The organic phase was washed successively with saturated ammonium chloride solution and then with brine, dried over magnesium sulfate, filtered and concentrated under reduced pressure as described in Example 1. Purification was performed by flash column chromatography as described in Example 1 to give the desired 1-(3-alkyl-1-methyl(1H)indol-3-yl)indole-2,3-dione.

Example 6: General Procedure F for the Preparation of (E)-1-(2-(1H-indol-3-yl)ethyl)-3-(2-(2-chlorophenyl)-2-oxoethylidene)indolin-2-one APV-ST505

Triethylamine (2 equiv., 0.58 mmol) was added to a solution of 1-(3-ethyl(1H)indol-3-yl)-3-hydroxy-3-(2-oxo-2-(2-chlorophenyl)ethyl)indol-2-one (1 equiv., 0.29 mmol) in dichloromethane (5 mL) at room temperature, in a flask of suitable size. The reaction mixture is stirred at room temperature, i.e. at 20° C., for 12 hours. The organic phase was washed successively with saturated ammonium chloride solution (2×2 mL) and then with brine (2 mL), dried over magnesium sulfate, filtered through a sinter funnel and concentrated under reduced pressure as described in Example 1 to give the desired (E)-1-(2-(1H-indol-3-yl)ethyl)-3-(2-(2-chlorophenyl)-2-oxoethylidene)indolin-2-one.

The compound APV-ST505 was prepared by following the general procedure F, using 1-(3-ethyl(1H)indol-3-yl)-3-hydroxy-3-(2-oxo-2-(2-chlorophenyl)ethyl)indol-2-one (130 mg, 0.29 mmol) and triethylamine (40 μL, 0.56 mmol). The compound indicated in the title was obtained in the form of a red solid (130 mg). Yield=quantitative.

$^1$H NMR (300 MHz, CDCl$_3$, δ ppm) 8.58 (d, J=7.7 Hz, 1H), 8.02 (s, 1H), 7.68 (d, J=8.3 Hz, 2H), 7.64 (s, 1H), 7.51-7.45 (m, 2H), 7-45-7.29 (m, 3H) 7.22 (t, J=7.2 Hz, 1H), 7.15 (t, J=7.2 Hz, 1H), 7.10-7.00 (m, 2H), 6.75 (d, J=7.8 Hz, 1H), 4.06 (t, J=7.6 Hz, 2H), 3.17 (t, J=7.6 Hz, 2H).

$^{13}$C NMR (75 MHz, DMSO-d$_6$, δ ppm) 191.9, 166.8, 145.6, 138.0, 136.2, 135.5, 133.5, 133.4, 132.4, 130.6, 130.3, 129.3, 127.8, 127.4, 127.3, 127.0, 123.1, 122.3, 121.0, 119.3, 118.3, 118.0, 111.4, 110.5, 109.4, 22.9.

HRMS (ESI, m/z) calculated for C$_{26}$H$_{19}$N$_2$O$_2$NaCl [M+Na]$^+$: 449.1033. found 449.1033.

Example 7: General Procedure G for the Preparation of 1-(2-(1H-indol-3-yl)ethyl)-3-(2-(2-chlorophenyl)-2-oxoethyl)indolin-2-one Palladium on active charcoal (8 mg, 10% weight/weight) was added to a solution of (E)-1-(2-(1H-indol-3-yl)ethyl)-3-(2-(2-chlorophenyl)-2-oxoethylidene)indolin-2-one (80 mg, 0.19 mmol) in methanol (13 ml) in a flask of suitable size, under an argon atmosphere at room temperature, i.e. at 20° C. The mixture is then placed under a hydrogen atmosphere and stirred at room temperature, i.e. at 20° C., for 1 hour. The crude product was filtered through a bed of Celite, which was washed with ethyl acetate. The filtrate was concentrated under reduced pressure to give the desired 1-(2-(1H-indol-3-yl)ethyl)-3-(2-(2-chlorophenyl)-2-oxoethyl)indolin-2-one.

1-(2-(1H-Indol-3-yl)ethyl)-3-(2-(2-chlorophenyl)-2-oxoethyl)indolin-2-one (APV-GG065)

The compound APV-GG065 was prepared by following the general procedure G, using (E)-1-(2-(1H-indol-3-yl)ethyl)-3-(2-(2-chlorophenyl)-2-oxoethylidene)indolin-2-one (80 mg, 0.19 mmol) and palladium on charcoal Pd/C (8 mg). The compound indicated in the title was obtained in the form of a beige-colored solid (60 mg). Yield=74%.

$^1$H NMR (300 MHz, CDCl$_3$, δ ppm) 8.00 (s, 1H), 7.59 (d, J=7.8 Hz, 1H), 7.50 (d, J=7.7 Hz, 1H), 7.45-7.38 (m, 2H) 7.38-7.27 (m, 3H), 7.25-7.07 (m, 4H), 7.01 (t, J=7.5 HZ, 1H), 6.84 (d, J=7.8 Hz, 1H), 4.10-3.98 (m, 3H), 3.65 (dd, J=18.4, 3.7 Hz, 1H), 3.23 (dd, J=18.4, 8.5 Hz, 1H), 3.17 (t, J=7.6 Hz, 2H). $^{13}$C NMR (75 MHz, CDCl$_3$, δ ppm) 200.2, 177.3, 143.9, 138.6, 136.4, 132.3, 131.3, 130.9, 129.5, 128.9, 128.3, 127.2, 124.7, 122.5, 122.4, 122.3, 119.7, 118.7, 112.7, 111.4, 108.5, 102.4, 44.1, 41.6, 41.1, 23.4. HRMS (ESI, m/z) calculated for C$_{26}$H$_{21}$N$_2$O$_2$NaCl [M+Na]$^+$: 451.1189. found 451.1194.

Example 8: Synthesis of Compounds According to the Invention (Compound Derived from Synthesis D)

1-(3-Ethyl(1H)indol-3-yl)-3-hydroxy-3-(2-oxo-2-phenylethyl)indol-2-one (APV-ST288)

The compound APV-ST288 was prepared by following the general procedure D, using 1-(3-ethyl(1H)indol-3-yl)indol-2,3-dione (80 mg, 0.28 mmol) and acetophenone (45 μL, 0.39 mmol). The compound indicated in the title was obtained after flash chromatography followed by trituration in pentane, in the form of a beige-colored solid (91 mg). Yield=80%. m.p.=159.7-161.5° C. $^1$H NMR (300 MHz, DMSO-d$_6$, δ ppm) 10.89 (s, 1H), 7.90 (d, J=7.6 Hz, 2H), 7.66 (d, J=7.8 Hz, 1H), 7.61 (d, J=7.1 Hz, 1H), 7.51 (d, J=7.5 Hz, 1H), 7.48 (d, J=7.6 Hz, 1H), 7.43-7.35 (m, 2H), 7.33 (s, 1H), 7.26 (dd, J=7.6, 7.6 Hz, 1H), 7.16-6.91 (m, 4H), 6.20 (s, 1H), 4.15 (d, J=17.5 Hz, 1H), 4.06-3.85 (m, 2H), 3.68 (d, J=17.4 Hz, 1H), 3.08 (t, J=7.8 Hz, 2H). $^{13}$C NMR (75 MHz, DMSO-d$_6$, δ ppm) 196.9, 177.0, 144.1, 136.7, 136.6, 133.9, 131.6, 129.6, 129.2, 129.2, 128.4, 128.4, 127.6, 123.9, 123.6, 122.2, 121.5, 118.9, 118.6, 111.9, 111.3, 108.8, 73.2, 46.6, 40.0, 23.2. FTIR (neat, cm$^{-1}$) 3359, 2954, 1702, 1678, 1615, 1344, 1221, 1170, 1061, 982, 741, 689. HRMS (ESI, m/z) calculated for C$_{26}$H$_{23}$N$_2$O$_3$ [M+H]$^+$: 411.1630. found 411.1705 and for C$_{26}$H$_{22}$N$_2$O$_3$Na [M+Na]$^+$: 433.1528. found 433.1526. Flash chromatography conditions: 25 g column, flow rate 18 mL/min, 100/0 to 50/50 cyclohexane/EtOAc. R$_f$=0.35, 50/50 cyclohexane/EtOAc.

1-(3-Ethyl(1H)indol-3-yl)-3-hydroxy-3-(2-oxo-2-(2-chlorophenyl)ethyl)indol-2-one (APV-ST357)

The compound APV-ST357 was prepared by following the general procedure D, using 1-(3-ethyl(1H)indol-3-yl)indol-2,3-dione (80 mg, 0.28 mmol) and 2'-chloroacetophenone (71 μL, 0.39 mmol). The compound indicated in the title was obtained after flash chromatography followed by trituration in pentane, in the form of a beige-colored solid (100 mg). Yield=81%. m.p.=100.5-101.9° C. $^1$H NMR (300 MHz, DMSO-d$_6$, δ ppm) 10.88 (s, 1H), 7.64 (d, J=7.4 Hz, 1H), 7.54-7.44 (m, 3H), 7.44-7.34 (m, 3H), 7.34-7.24 (m, 2H), 7.18-6.93 (m, 4H), 6.26 (s, 1H), 4.03-3.82 (m, 3H), 3.63 (d, J=16.7 Hz, 1H), 3.05 (t, J=7.6 Hz, 2H). $^{13}$C NMR (75 MHz, DMSO-d$_6$, δ ppm) 199.0, 176.6, 143.8, 138.4, 136.7, 132.9, 130.9, 130.9, 130.1, 129.8, 129.7, 127.8, 127.5, 124.3, 123.6, 122.3, 121.5, 118.9, 118.5, 111.9, 111.3, 108.9, 73.2, 50.3, 40.6, 23.2. FTIR (neat, cm$^{-1}$) 3381, 2920, 1693, 1615, 1469, 1353, 1336, 1163, 1061, 741. HRMS (ESI, m/z) calculated for C$_{26}$H$_{22}$N$_2$O$_3$Cl [M+H]$^+$: 445.1319. found 445.1326 and for C$_{26}$H$_{21}$N$_2$O$_3$ClNa [M+Na]$^+$: 467.1138. found 467.1133. Flash chromatography conditions: 25 g column, flow rate 18 mL/min, 100/0 to 50/50 cyclohexane/EtOAc. R$_f$=0.50, 50/50 cyclohexane/EtOAc.

1-(3-Ethyl(1H)indol-3-yl)-3-hydroxy-3-(2-oxo-2-(3-chlorophenyl)ethyl)indol-2-one (APV-ST292)

The compound APV-ST292 was prepared by following the general procedure D, using 1-(3-ethyl(1H)indol-3-yl)indol-2,3-dione (80 mg, 0.28 mmol) and 3'-chloroacetophenone (51 μL, 0.39 mmol). The compound indicated in the title was obtained after flash chromatography followed by trituration in pentane, in the form of a beige-colored solid (88 mg). Yield=72%. m.p.=130.2-133.4° C., $^1$H NMR (300 MHz, CDCl$_3$, δ ppm) 8.23 (s, 1H), 7.81 (s, 1H), 7.69 (d, J=7.7 Hz, 1H), 7.57-7.47 (m, 2H), 7.41-7.33 (m, 3H), 7.29 (d, J=8.2 Hz, 1H), 7.18 (dd, J=7.6, 7.6 Hz, 1H), 7.12-7.01 (m, 3H), 6.88 (d, J=7.9 Hz, 1H), 4.20-3.95 (m, 3H), 3.64 (d, J=17.4 Hz, 1H), 3.32 (d, J=17.5 Hz, 1H), 3.22 (t, J=7.2 Hz, 2H). $^{13}$C NMR (75 MHz, CDCl$_3$, δ ppm) 196.7, 176.1, 143.2, 137.8, 136.2, 135.0, 133.6, 130.0, 130.0, 129.9, 128.2, 127.5, 126.3, 124.1, 122.9, 122.7, 122.0, 119.3, 118.4, 112.2, 111.4, 108.9, 74.2, 44.6, 41.0, 22.9. FTIR (neat, cm$^{-1}$) 3332, 1702, 1683, 1616, 1413, 1337, 1215, 1170, 1066, 748. HRMS (ESI, m/z) calculated for C$_{26}$H$_{22}$N$_2$O$_3$Cl [M+H]$^+$: 445.1319. found 445.1306 and for C$_{26}$H$_{21}$N$_2$O$_3$ClNa [M+Na]$^+$: 467.1138. found 467.1139. Flash chromatography conditions: 25 g column, flow rate 18 mL/min, 100/0 to 50/50 cyclohexane/EtOAc. R$_f$=0.46, 50/50 cyclohexane/EtOAc.

1-(3-Ethyl(1H)indol-3-yl)-3-hydroxy-3-(2-oxo-2-(4-chlorophenyl)ethyl)indol-2-one (APV-ST358)

The compound APV-ST358 was prepared by following the general procedure D, using 1-(3-ethyl(1H)indol-3-yl)indole-2,3-dione (80 mg, 0.28 mmol) and 4'-chloroacetophenone (51 μL, 0.39 mmol). The compound indicated in the title was obtained after flash chromatography followed by trituration in pentane, in the form of a beige-colored solid (91 mg). Yield=74%. m.p.=176.9-178.1° C. $^1$H NMR (300 MHz, DMSO-d$_6$, δ ppm) 10.89 (s, 1H), 7.91 (d, J=8.4 Hz, 2H), 7.66 (d, J=7.6 Hz, 1H), 7.55 (d, J=8.3 Hz, 2H), 7.43-7.35 (m, 2H), 7.33 (d, J=1.5 Hz, 1H), 7.27 (dd, J=7.7, 7.7 Hz, 1H), 7.17-6.91 (m, 4H), 6.23 (s, 1H), 4.13 (d, J=17.4 Hz, 1H), 4.07-3.84 (m, 2H), 3.67 (d, J=17.4 Hz, 1H), 3.08 (t, J=7.8 Hz, 2H). $^{13}$C NMR (75 MHz, DMSO-d$_6$, δ ppm) 196.0, 176.9, 144.0, 138.9, 136.8, 135.3, 131.5, 130.4, 130.4, 129.6, 129.2, 129.2, 127.6, 124.0, 123.6, 122.2, 121.5, 118.9, 118.6, 112.0, 111.3, 108.8, 73.2, 46.6, 40.6, 23.2. FTIR (neat, cm$^{-1}$) 3334, 1703, 1658, 1613, 1589, 1381, 1355, 1338, 1219, 1169, 1006, 837, 739. HRMS (ESI, m/z) calculated for C$_{26}$H$_{22}$N$_2$O$_3$Cl [M+H]$^+$: 445.1319. found 445.1330 and for C$_{26}$H$_{21}$N$_2$O$_3$ClNa [M+Na]$^+$: 467.1138. found 467.1134. Flash chromatography conditions: 25 g column, flow rate 18 mL/min, 100/0 to 50/50 cyclohexane/EtOAc. R$_f$=0.50, 50/50 cyclohexane/EtOAc.

1-(3-Ethyl(1H)indol-3-yl)-3-hydroxy-3-(2-oxo-2-(pyrid-2-yl)ethyl)indol-2-one (APV-ST430)

The compound APV-ST430 was prepared by following the general procedure D, using 1-(3-ethyl(1H)indol-3-yl)indole-2,3-dione (80 mg, 0.28 mmol) and 2-acetylpyridine (42 μL, 0.39 mmol). The compound indicated in the title was obtained after flash chromatography followed by trituration in pentane, in the form of a beige-colored solid (95 mg). Yield=84%. m.p.=156.8-158.5° C. $^1$H NMR (300 MHz, DMSO-d$_6$, δ ppm) 10.88 (s, 1H), 8.75 (d, J=4.1 Hz, 1H), 7.98-7.89 (m, 1H), 7.77 (d, J=7.8 Hz, 1H), 7.69-7.62 (m, 2H), 7.37 (d, J=7.8 Hz, 1H), 7.34-7.29 (m, 2H), 7.29-7.21 (m, 1H), 7.14-6.98 (m, 3H), 6.96-6.89 (m, 1H), 6.25 (s, 1H), 4.37 (d, J=17.9 Hz, 1H), 4.04-3.86 (m, 2H), 3.74 (d, J=17.8 Hz, 1H), 3.07 (t, J=8.0 Hz, 2H). $^{13}$C NMR (75 MHz, DMSO-d$_6$, δ ppm) 198.2, 176.9, 152.6, 149.7, 144.0, 138.1, 136.7, 131.5, 129.6, 128.4, 127.5, 123.9, 123.6, 122.2, 121.6, 121.5, 118.9, 118.6, 111.9, 111.3, 108.8, 73.2, 45.7, 40.5, 23.3. FTIR (neat, cm$^{-1}$) 3350, 3250, 1680, 1613, 1461, 1353, 1170, 1065, 994, 772, 739. HRMS (ESI, m/z) calculated for C$_{25}$H$_{21}$N$_3$O$_3$Na [M+Na]$^+$: 434.1481. found 434.1473. Flash chromatography conditions: 10 g column, flow rate 8 mL/min, 100/0 to 40/60 cyclohexane/EtOAc. $R_f$=0.16, 50/50 cyclohexane/EtOAc.

1-(3-Ethyl(1H)indol-3-yl)-3-hydroxy-3-(2-oxo-2-(pyrid-3-yl)ethyl)indol-2-one (APV-ST296)

The compound APV-ST296 was prepared by following the general procedure D, using 1-(3-ethyl(1H)indol-3-yl)indole-2,3-dione (80 mg, 0.28 mmol) and 3-acetylpyridine (43 µL, 0.39 mmol). The compound indicated in the title was obtained after flash chromatography followed by trituration in pentane, in the form of a beige-colored solid (76 mg). Yield=68%. m.p.=124.2-126.1° C. $^1$H NMR (300 MHz, CDCl$_3$, δ ppm) 8.92 (s, 1H), 8.64 (d, J=4.5 Hz, 1H), 8.51 (s, 1H), 8.05 (d, J=8.0 Hz, 1H), 7.48 (d, J=7.8 Hz, 1H), 7.40-7.26 (m, 4H), 7.18-7.11 (m, 1H), 7.09-6.99 (m, 3H), 6.87 (d, J=7.8 Hz, 1H), 4.84 (br. s, 1H), 4.15-3.94 (m, 2H), 3.68 (d, J=17.2 Hz, 1H), 3.38 (d, J=17.2 Hz, 1H), 3.18 (t, J=7.1 Hz, 2H). $^{13}$C NMR (75 MHz, CDCl$_3$, δ ppm) 196.5, 176.4, 153.5, 149.4, 143.2, 136.2, 135.6, 131.8, 130.0, 129.9, 127.5, 124.0, 123.6, 122.9, 122.7, 121.9, 119.2, 118.3, 112.0, 111.5, 109.0, 74.0, 45.0, 40.9, 22.8. FTIR (neat, cm$^{-1}$) 3321, 2942, 1716, 1690, 1613, 1468, 1355, 1229, 116, 740, 701. HRMS (ESI, m/z) calculated for $C_{25}H_{22}N_3O_3$ [M+H]$^+$: 412.1661. found 412.1667 and for $C_{25}H_{21}N_3O_3Na$ [M+Na]$^+$: 434.1481. found 434.1486. Flash chromatography conditions: 25 g column, flow rate 18 mL/min, 100/0 to 50/50 cyclohexane/EtOAc. $R_f$=0.05, 50/50 cyclohexane/EtOAc.

1-(3-Ethyl(1H)indol-3-yl)-3-hydroxy-3-(2-oxo-2-(pyrid-4-yl)ethyl)indol-2-one (APV-ST431)

The compound APV-ST431 was prepared by following the general procedure D, using 1-(3-ethyl(1H)indol-3-yl)indole-2,3-dione (80 mg, 0.28 mmol) and 4-acetylpyridine (42 µL, 0.39 mmol). The compound indicated in the title was obtained after flash chromatography followed by trituration in pentane, in the form of a beige-colored solid (104 mg). Yield=92%. m.p.=126.5-127.8° C. $^1$H NMR (300 MHz, DMSO-d$_6$, δ ppm) 10.88 (s, 1H), 8.77 (d, J=5.0 Hz, 1H), 7.75 (d, J=5.1 Hz, 2H), 7.64 (d, J=7.6 Hz, 1H), 7.38 (d, J=7.7 Hz, 2H), 7.32-7.22 (m, 2H), 7.15-6.92 (m, 5H), 6.26 (s, 1H), 4.14 (d, J=17.4 Hz, 1H), 4.03-3.83 (m, 2H), 3.67 (d, J=17.5 Hz, 1H), 3.06 (t, J=7.7 Hz, 2H). $^{13}$C NMR (75 MHz, DMSO-d$_6$, δ ppm) 197.3, 176.7, 151.2, 151.2, 143.9, 142.4, 136.7, 131.2, 129.7, 129.7, 127.5, 124.1, 123.6, 122.3, 121.5, 121.5, 118.9, 118.6, 111.9, 111.2, 108.9, 73.1, 46.8, 40.5, 23.2. FTIR (neat, cm$^{-1}$) 3340, 3098, 1697, 16313, 1468, 1355, 1225, 1166, 1063, 741. HRMS (ESI, m/z) calculated for $C_{25}H_{22}N_3O_3$ [M+H]$^+$: 412.1661. found 412.1667 and for $C_{25}H_{21}N_3O_3Na$ [M+Na]$^+$: 434.1481. found 434.1483. Flash chromatography conditions: 10 g column, flow rate 8 mL/min, 100/0 to 40/60 cyclohexane/EtOAc. $R_f$=0.04, 50/50 cyclohexane/EtOAc.

1-(3-Ethyl(1H)indol-3-yl)-3-hydroxy-3-(2-oxo-2-(2-hydroxyphenyl)ethyl)indol-2-one (APV-ST415)

The compound APV-ST415 was prepared by following the general procedure D, using 1-(3-ethyl(1H)indol-3-yl)indole-2,3-dione (80 mg, 0.28 mmol) and 2'-hydroxyacetophenone (47 µL, 0.39 mmol). The compound indicated in the title was obtained after flash chromatography followed by trituration in pentane, in the form of a beige-colored solid (116 mg). Yield=99%. m.p.=114.8-116.7° C. $^1$H NMR (300 MHz, DMSO-d$_6$, δ ppm) 11.32 (s, 1H), 10.88 (s, 1H), 7.78 (d, J=8.2 Hz, 1H), 7.64 (d, J=7.6 Hz, 1H), 7.53-7.43 (m, 1H), 7.41-7.33 (m, 2H), 7.30 (s, 1H), 7.26 (d, J=7.7 Hz, 1H), 7.15-6.88 (m, 6H), 6.20 (s, 1H), 4.15 (d, J=17.6 Hz, 1H), 4.04-3.84 (m 2H), 3.72 (d, J=17.7 Hz, 1H), 3.05 (t, J=7.8 Hz, 2H). $^{13}$C NMR (75 MHz, DMSO-d$_6$, δ ppm) 201.6, 176.9, 160.5, 144.0, 136.7, 136.4, 131.5, 131.1, 129.6, 127.5, 124.0, 123.6, 122.2, 121.5, 121.6, 119.7, 118.9, 118.6, 118.0, 111.9, 111.3, 108.8, 73.2, 48.2, 40.5, 23.1. FTIR (neat, cm$^{-1}$) 3336, 2911, 1701, 1640, 1613, 1370, 1276, 1157, 740. HRMS (ESI, m/z) calculated for $C_{26}H_{23}N_2O_4$ [M+H]$^+$: 427.1658. found 427.1649 and for $C_{26}H_{22}N_2O_4Na$ [M+Na]$^+$: 449.1477. found 449.1479. Flash chromatography conditions: 25 g column, flow rate 18 mL/min, 100/0 to 50/50 cyclohexane/EtOAc. $R_f$=0.49, 50/50 cyclohexane/EtOAc.

1-(3-Ethyl(1H)indol-3-yl)-3-hydroxy-3-(2-oxo-2-(3-hydroxyphenyl)ethyl)indol-2-one (APV-ST360)

The compound APV-ST360 was prepared by following the general procedure D, using 1-(3-ethyl(1H)indol-3-yl)indole-2,3-dione (100 mg, 0.34 mmol) and 3'-hydroxyacetophenone (65 mg, 0.48 mmol). The compound indicated in the title was obtained after flash chromatography followed by trituration in pentane, in the form of a beige-colored solid (119 mg). Yield=82%. m.p.=145.3-147.2° C. $^1$H NMR (300 MHz, DMSO-d$_6$, δ ppm) 10.88 (s, 1H), 9.76 (s, 1H), 7.65 (d, J=7.6 Hz, 1H), 7.42-7.18 (m, 7H), 7.15-6.91 (m, 5H), 6.16 (s, 1H), 4.07 (d, J=17.5 Hz, 1H), 4.03-3.83 (m, 2H), 3.61 (d, J=17.5 Hz, 1H), 3.06 (t, J=7.8 Hz, 2H). $^{13}$C NMR (75 MHz, DMSO-d$_6$, δ ppm) 196.7, 177.0, 158.0, 144.1, 137.9, 136.7, 131.6, 130.3, 129.6, 127.6, 123.9, 123.6, 122.1, 121.5, 121.0, 119.4, 118.9, 118.6, 114.4, 111.9, 111.3, 108.8, 73.1, 46.6, 40.5, 23.2. FTIR (neat, cm$^{-1}$) 3357, 2910, 1680, 1614, 1469, 1452, 1339, 1166, 739. HRMS (ESI, m/z) calculated for $C_{26}H_{23}N_2O_4$ [M+H]$^+$: 427.1658. found 427.1645 and for $C_{26}H_{22}N_2O_4Na$ [M+Na]$^+$: 449.1477. found 449.1486. Flash chromatography conditions: 25 g column, flow rate 18 mL/min, 100/0 to 50/50 cyclohexane/EtOAc. $R_f$=0.15, 50/50 cyclohexane/EtOAc.

1-(3-Ethyl(1H)indol-3-yl)-3-hydroxy-3-(2-oxo-2-(4-hydroxyphenyl)ethyl)indol-2-one (APV-ST428)

The compound APV-ST428 was prepared by following the general procedure D, using 1-(3-ethyl(1H)indol-3-yl)indole-2,3-dione (80 mg, 0.28 mmol) and 4'-hydroxyacetophenone (53 mg, 0.39 mmol). The compound indicated in the title was obtained after flash chromatography followed by trituration in pentane, in the form of a beige-colored solid (52 mg). Yield=44%. m.p.=111.7-113.5° C. $^1$H NMR (300 MHz, DMSO-d$_6$, δ ppm) 10.87 (s, 1H), 10.36 (s, 1H), 7.76 (d, J=8.1 Hz, 2H), 7.64 (d, J=7.8 Hz, 1H), 7.39-7.31 (m, 2H), 7.27-7.21 (m, 1H), 7.14-6.89 (m, 5H), 6.81 (d, J=8.1 Hz, 2H), 6.10 (s, 1H), 4.02 (d, J=17.3 Hz, 1H), 3.99-3.80 (m, 2H), 3.55 (d, J=17.1 Hz, 1H), 3.05 (t, J=7.9 Hz, 2H). $^{13}$C NMR (75 MHz, DMSO-d$_6$, δ ppm) 194.9, 177.1, 162.7, 144.1, 136.7, 131.8, 131.0, 131.0, 129.4, 128.3, 127.6, 123.8, 123.6, 122.0, 121.5, 118.9, 118.6, 115.6, 115.6, 111.9, 111.4, 108.7, 73.2, 46.1, 40.5, 23.2. FTIR (neat, cm$^{-1}$) 3400, 2901, 1691, 1669, 1599, 1579, 1356, 1232, 1167, 844, 794. HRMS (ESI, m/z) calculated for $C_{26}H_{22}N_2O_4Na$ [M+Na]$^+$: 449.1477. found 449.1466. Flash chromatography conditions: 10 g column, flow rate 8 mL/min, 100/0 to 50/50 cyclohexane/EtOAc. $R_f$=0.11, 50/50 cyclohexane/EtOAc.

1-(3-Ethyl(1H)indol-3-yl)-3-hydroxy-3-(2-oxo-2-(2-aminophenyl)ethyl)indol-2-one (APV-ST432)

The compound APV-ST432 was prepared by following the general procedure D, using 1-(3-ethyl(1H)indol-3-yl)indole-2,3-dione (80 mg, 0.28 mmol) and 2'-aminoacetophenone (47 μL, 0.39 mmol). The compound indicated in the title was obtained after flash chromatography followed by trituration in pentane, in the form of a beige-colored solid (82 mg). Yield=70%. m.p.=149.6-151.5° C. $^1$H NMR (300 MHz, DMSO-d$_6$, δ ppm) 10.89 (s, 1H), 7.81 (d, J=8.1 Hz, 1H), 7.66 (d, J=7.7 Hz, 1H), 7.41-7.31 (m, 3H), 7.30-7.19 (m, 2H), 7.14-6.92 (m, 6H), 6.70 (d, J=8.4 Hz, 1H), 6.61-6.53 (m, 1H), 6.10 (s, 1H), 4.07 (d, J=17.2 Hz, 1H), 4.03-3.86 (m, 2H), 3.63 (d, J=17.2 Hz, 1H), 3.08 (t, J=7.8 Hz, 2H). $^{13}$C NMR (75 MHz, DMSO-d$_6$, δ ppm) 198.6, 177.2, 151.5, 144.2, 136.7, 134.8, 132.0, 131.8, 129.4, 127.6, 123.8, 123.6, 122.0, 121.5, 118.9, 118.6, 117.4, 116.5, 115.0, 111.9, 111.4, 108.7, 73.3, 47.0, 40.5, 23.1. FTIR (neat, cm$^{-1}$) 3329, 2910, 1712, 1613, 1359, 1163, 740. HRMS (ESI, m/z) calculated for C$_{26}$H$_{24}$N$_3$O$_3$ [M+H]$^+$: 426.1818. found 426.1826 and for C$_{26}$H$_{23}$N$_3$O$_3$Na [M+Na]$^+$: 448.1637. found 488.1636. Flash chromatography conditions: 10 g column, flow rate 8 mL/min, 100/0 to 50/50 cyclohexane/EtOAc. R$_f$=0.38, 50/50 cyclohexane/EtOAc.

1-(3-Ethyl(1H)indol-3-yl)-3-hydroxy-3-(2-oxo-2-(3-aminophenyl)ethyl)indol-2-one (APV-ST362)

The compound APV-ST362 was prepared by following the general procedure D, using 1-(3-ethyl(1H)indol-3-yl)indole-2,3-dione (80 mg, 0.28 mmol) and 3'-aminoacetophenone (53 mg, 0.39 mmol). The compound indicated in the title was obtained after flash chromatography followed by trituration in pentane, in the form of a beige-colored solid (105 mg). Yield=89%. m.p.=190.3-192.1° C. $^1$H NMR (300 MHz, DMSO-d$_6$, δ ppm) 10.88 (s, 1H), 7.65 (d, J=7.6 Hz, 1H), 7.40-7.22 (m, 4H), 7.17-6.90 (m, 7H), 6.78 (d, J=8.2 Hz, 1H), 6.12 (s, 1H), 5.30 (s, 2H), 4.01 (d, J=17.6 Hz, 1H), 4.10-3.81 (m, 2H), 3.57 (d, J=17.5 Hz, 1H), 3.06 (t, J=7.9 Hz, 2H). $^{13}$C NMR (75 MHz, DMSO-d$_6$, δ ppm) 196.7, 176.6, 149.0, 143.7, 136.9, 136.3, 131.2, 129.1, 129.1, 127.1, 123.4, 123.2, 121.6, 121.0, 118.7, 118.4, 118.1, 115.5, 112.4, 111.5, 110.9, 108.3, 72.7, 46.1, 40.1, 22.7. FTIR (neat, cm$^{-1}$) 3361, 2903, 1694, 1618, 1468, 1654, 1350, 1169, 1061, 738. HRMS (ESI, m/z) calculated for C$_{26}$H$_{24}$N$_3$O$_3$ [M+H]$^+$: 426.1818. found 426.1812. Flash chromatography conditions: 25 g column, flow rate 18 mL/min, 100/0 to 50/50 cyclohexane/EtOAc. R$_f$=0.08, 50/50 cyclohexane/EtOAc.

1-(3-Ethyl(1H)indol-3-yl)-3-hydroxy-3-(2-oxo-2-(4-aminophenyl)ethyl)indol-2-one (APV-ST433)

The compound APV-ST433 was prepared by following the general procedure D, using 1-(3-ethyl(1H)indol-3-yl)indole-2,3-dione (80 mg, 0.28 mmol) and 4'-aminoacetophenone (53 mg, 0.39 mmol). The compound indicated in the title was obtained after flash chromatography followed by trituration in pentane, in the form of a beige-colored solid (68 mg). Yield=58%. m.p.=141.6-143.4° C. $^1$H NMR (300 MHz, DMSO-d$_6$, δ ppm) 10.87 (s, 1H), 7.65 (d, J=7.7 Hz, 1H), 7.60 (d, J=8.5 Hz, 2H), 7.40-7.20 (m, 4H), 7.14-7.01 (m, 2H), 6.99-6.89 (m, 2H), 6.53 (d, J=8.5 Hz, 2H), 6.11-6.01 (m, 3H), 4.03-3.80 (m, 2H), 3.93 (d, J=17.0 Hz, 1H), 3.47 (d, J=17.0 Hz, 1H), 3.05 (t, J=7.9 Hz, 2H). $^{13}$C NMR (75 MHz, DMSO-d$_6$, b ppm) 193.7, 177.2, 154.3, 144.2, 136.7, 132.0, 130.8, 130.8, 129.3, 127.6, 124.5, 123.7, 123.6, 122.0, 121.5, 118.9, 118.6, 112.9, 112.9, 111.9, 111.4, 108.6, 73.3, 45.7, 40.5, 23.2. FTIR (neat, cm$^{-1}$) 3357, 2942, 1712, 1614, 1591, 1562, 1355, 1229, 1176, 740. HRMS (ESI, m/z) calculated for C$_{26}$H$_{24}$N$_3$O$_3$ [M+H]$^+$: 426.1818. found 426.1810. Flash chromatography conditions: 10 g column, flow rate 8 mL/min, 100/0 to 50/50 cyclohexane/EtOAc. R$_f$=0.10, 50/50 cyclohexane/EtOAc.

1-(3-Ethyl(1H)indol-3-yl)-3-hydroxy-3-(2-oxo-2-(3-methylphenyl)ethyl)indol-2-one (APV-ST373)

The compound APV-ST373 was prepared by following the general procedure D, using 1-(3-ethyl(1H)indol-3-yl)indole-2,3-dione (80 mg, 0.28 mmol) and 3'-methylacetophenone (51 μL, 0.39 mmol). The compound indicated in the title was obtained after flash chromatography followed by trituration in pentane, in the form of a beige-colored solid (85 mg). Yield=73%. m.p.=107.9-109.9° C. $^1$H NMR (300 MHz, DMSO-d$_6$, δ ppm) 10.89 (s, 1H), 7.71 (s, 1H), 7.69-7.63 (m, 1H), 7.46-7.30 (m, 5H), 7.30-7.22 (m, 1H), 7.14-6.91 (m, 5H), 6.16 (s, 1H), 4.13 (d, J=17.5 Hz, 1H), 4.07-3.84 (m, 2H), 3.65 (d, J=17.5 Hz, 1H), 3.07 (t, J=7.8 Hz, 2H), 2.35 (s, 3H). $^{13}$C NMR (75 MHz, DMSO-d$_6$, δ ppm) 197.0, 177.0, 144.1, 138.6, 136.7, 136.6, 134.5, 131.6, 129.6, 129.0, 128.8, 127.6, 125.6, 123.9, 123.6, 122.1, 121.5, 118.9, 118.6, 111.9, 111.3, 108.8, 73.2, 46.6, 40.5, 23.2, 21.2. FTIR (neat, cm$^{-1}$) 3380, 3001, 1688, 1612, 1565, 1422, 1341, 1200, 1067, 741. HRMS (ESI, m/z) calculated for C$_{27}$H$_{25}$N$_2$O$_3$ [M+H]$^+$: 425.1865. found 425.1864 and for C$_{27}$H$_{24}$N$_2$O$_3$Na [M+Na]$^+$: 447.1685. found 447.1685. Flash chromatography conditions: 25 g column, flow rate 18 mL/min, 100/0 to 50/50 cyclohexane/EtOAc. R$_f$=0.45, 50/50 cyclohexane/EtOAc.

1-(3-Ethyl(1H)indol-3-yl)-3-hydroxy-3-(2-oxo-2-(4-methylphenyl)ethyl)indol-2-one (APV-ST426)

The compound APV-ST426 was prepared by following the general procedure D, using 1-(3-ethyl(1H)indol-3-yl)indole-2,3-dione (80 mg, 0.28 mmol) and 4'-methylacetophenone (52 mg, 0.39 mmol). The compound indicated in the title was obtained after flash chromatography followed by trituration in pentane, in the form of a beige-colored solid (101 mg). Yield=86%. m.p.=198.4-200.1° C. $^1$H NMR (300 MHz, DMSO-d$_6$, δ ppm) 10.88 (s, 1H), 7.79 (d, J=7.9 Hz, 2H), 7.65 (d, J=7.5 Hz, 1H), 7.42-7.22 (m, 6H), 7.14-6.90 (m, 4H), 6.16 (s, 1H), 4.10 (d, J=17.4 Hz, 1H), 4.03-3.83 (m, 2H), 3.63 (d, J=17.4 Hz, 1H), 3.06 (t, J=7.8 Hz, 2H), 2.36 (s, 3H). $^{13}$C NMR (75 MHz, DMSO-d$_6$, δ ppm) 196.4, 177.0, 144.3, 144.1, 136.7, 134.2, 131.6, 129.7, 129.7, 129.5, 128.5, 128.5, 127.6, 123.9, 123.6, 122.1, 121.5, 118.9, 118.6, 111.9, 111.3, 108.8, 73.2, 46.4, 40.5, 23.2, 21.6. FTIR (neat, cm$^{-1}$) 3318, 2935, 1703, 1675, 1605, 1340, 1183, 1169, 1066, 739. HRMS (ESI, m/z) calculated for C$_{27}$H$_{24}$N$_2$O$_3$Na [M+Na]$^+$: 447.1685. found 447.1673. Flash chromatography conditions: 10 g column, flow rate 8 mL/min, 100/0 to 50/50 cyclohexane/EtOAc. R$_f$=0.45, 50/50 cyclohexane/EtOAc.

1-(3-Ethyl(1H)indol-3-yl)-3-hydroxy-3-(2-oxo-2-(2-methoxyphenyl)ethyl)indol-2-one (APV-ST402)

The compound APV-ST402 was prepared by following the general procedure D, using 1-(3-ethyl(1H)indol-3-yl)indole-2,3-dione (80 mg, 0.28 mmol) and 2'-methoxyacetophenone (53 μL, 0.39 mmol). The compound indicated in the title was obtained after flash chromatography followed by trituration in pentane, in the form of a beige-colored solid (102 mg). Yield=84%. m.p.=108.4-110.3° C. $^1$H NMR (300 MHz, DMSO-d$_6$, δ ppm) 10.89 (s, 1H), 7.66 (d, J=7.6 Hz, 1H), 7.56-7.48 (m, 1H), 7.39 (d, J=7.9 Hz, 1H), 7.35-7.23 (m, 4H), 7.19-6.90 (m, 6H), 6.12 (s, 1H), 4.07-3.83 (m, 6H), 3.71 (d, J=17.8 Hz, 1H), 3.07 (t, J=7.7 Hz, 2H). $^{13}$C NMR (75 MHz, DMSO-d$_6$, δ ppm) 198.0, 177.0, 158.9, 144.1, 136.7, 134.6, 131.6, 129.8, 129.5, 127.6, 127.4, 123.8, 123.6, 122.1, 121.5, 120.9, 118.9, 118.6, 112.9, 111.9, 111.4, 108.7, 73.2, 56.3, 51.8, 40.5, 23.2. FTIR (neat, cm$^{-1}$) 3355, 2942, 1701, 1614, 156, 1467, 1339, 1244, 1163, 1016, 755. HRMS (ESI, m/z) calculated for C$_{27}$H$_{25}$N$_2$O$_4$ [M+H]$^+$: 441.1814. found 441.1814 and for C$_{27}$H$_{24}$N$_2$O$_4$Na [M+Na]$^+$: 463.1634. found 463.1640. Flash chromatography conditions: 25 g column, flow rate 18 mL/min, 100/0 to 50/50 cyclohexane/EtOAc. R$_f$=0.24, 50/50 cyclohexane/EtOAc.

1-(3-Ethyl(1H)indol-3-yl)-3-hydroxy-3-(2-oxo-2-(3-methoxyphenyl)ethyl)indol-2-one (APV-ST403)

The compound APV-ST403 was prepared by following the general procedure D, using 1-(3-ethyl(1H)indol-3-yl)indole-2,3-dione (80 mg, 0.28 mmol) and 3'-methoxyacetophenone (53 μL, 0.39 mmol). The compound indicated in the title was obtained after flash chromatography followed by trituration in pentane, in the form of a beige-colored solid (110 mg). Yield=91%. m.p.=193.3-195.2° C. $^1$H NMR (300 MHz, DMSO-d$_6$, δ ppm) 10.88 (s, 1H), 7.65 (d, J=7.6 Hz, 1H), 7.52 (d, J=7.5 Hz, 1H), 7.46-7.31 (m, 5H), 7.30-7.22 (m, 1H), 7.22-7.16 (m, 1H), 7.14-6.92 (m, 4H), 6.16 (s, 1H), 4.14 (d, J=17.6 Hz, 1H), 3.99-3.86 (m, 2H), 3.79 (s, 3H), 3.67 (d, J=17.6 Hz, 1H), 3.06 (t, J=7.8 Hz, 2H). $^{13}$C NMR (75 MHz, DMSO-d$_6$, δ ppm) 196.7, 177.0, 159.8, 144.1, 137.9, 136.7, 131.6, 130.3, 129.6, 127.6, 123.9, 123.6, 122.2, 121.5, 121.0, 120.2, 118.8, 118.6, 112.5, 111.9, 111.3, 108.8, 73.6, 55.8, 46.7, 40.6, 23.2. FTIR (neat, cm$^{-1}$) 3326, 2923, 1704, 1674, 1613, 1412, 1339, 1256, 1069, 981, 746. HRMS (ESI, m/z) calculated for C$_{27}$H$_{25}$N$_2$O$_4$ [M+H]$^+$: 441.1814. found 441.1815 and for C$_{27}$H$_{24}$N$_2$O$_4$Na [M+Na]$^+$: 463.1634. found 463.1642. Flash chromatography conditions: 25 g column, flow rate 18 mL/min, 100/0 to 50/50 cyclohexane/EtOAc. R$_f$=0.30, 50/50 cyclohexane/EtOAc.

1-(3-Ethyl(1H)indol-3-yl)-3-hydroxy-3-(2-oxo-2-(4-methoxyphenyl)ethyl)indol-2-one (APV-ST429)

The compound APV-ST429 was prepared by following the general procedure D, using 1-(3-ethyl(1H)indol-3-yl)indole-2,3-dione (80 mg, 0.28 mmol) and 4'-methoxyacetophenone (58 mg, 0.39 mmol). The compound indicated in the title was obtained after flash chromatography followed by trituration in pentane, in the form of a beige-colored solid (82 mg). Yield=68%. m.p.=183.8-185.6° C. $^1$H NMR (300 MHz, DMSO-d$_6$, δ ppm) 10.88 (s, 1H), 7.87 (d, J=8.7 Hz, 2H), 7.65 (d, J=7.6 Hz, 1H), 7.42-7.30 (m, 3H), 7.28-7.22 (m, 1H), 7.14-6.90 (m, 6H), 6.14 (s, 1H), 4.07 (d, J=17.2 Hz, 1H), 4.00-3.85 (m, 2H), 3.83 (s, 3H), 3.60 (d, J=17.3 Hz, 1H), 3.06 (t, J=7.8 Hz, 2H). $^{13}$C NMR (75 MHz, DMSO-d$_6$, δ ppm) 195.2, 177.0, 163.7, 144.1, 136.7, 131.7, 130.77, 130.8, 129.6, 129.5, 127.6, 123.9, 123.6, 122.1, 121.5, 118.9, 118.6, 114.3, 114.3, 111.9, 111.3, 108.8, 73.2, 56.0, 46.2, 40.5, 23.2. FTIR (neat, cm$^{-1}$) 3319, 2904, 1705, 1667, 1597, 1340, 1234, 1171, 1067, 1025, 852, 742. HRMS (ESI, m/z) calculated for C$_{27}$H$_{24}$N$_2$O$_4$Na [M+Na]$^+$: 463.1634. found 463.1622. Flash chromatography conditions: 10 g column, flow rate 8 mL/min, 100/0 to 50/50 cyclohexane/EtOAc. R$_f$=0.23, 50/50 cyclohexane/EtOAc.

1-(3-Ethyl(1H)indol-3-yl)-3-hydroxy-3-(2-oxo-2-(3-bromophenyl)ethyl)indol-2-one (APV-ST374)

The compound APV-ST374 was prepared by following the general procedure D, using 1-(3-ethyl(1H)indol-3-yl)indole-2,3-dione (80 mg, 0.28 mmol) and 3'-bromoacetophenone (51 μL, 0.39 mmol). The compound indicated in the title was obtained after flash chromatography followed by trituration in pentane, in the form of a beige-colored solid (91 mg). Yield=68%. m.p.=148.1-149.7° C. $^1$H NMR (300 MHz, DMSO-d$_6$, δ ppm) 10.88 (s, 1H), 8.01 (s, 1H), 7.90 (d, J=7.7 Hz, 1H), 7.82 (d, J=8.1 Hz, 1H), 7.65 (d, J=7.6 Hz, 1H), 7.52-7.43 (m, 1H), 7.38 (d, J=7.6 Hz, 2H), 7.31 (d, J=1.5 Hz, 1H), 7.31-7.23 (m, 1H), 7.17-6.92 (m, 4H), 6.20 (s, 1H), 4.14 (d, J=17.5 Hz, 1H), 4.06-3.82 (m, 2H), 3.65 (d, J=17.4 Hz, 1H), 3.06 (t, J=7.8 Hz, 2H). $^{13}$C NMR (75 MHz, DMSO-d$_6$, δ ppm) 196.0, 176.8, 144.0, 138.6, 136.7, 136.5, 131.4, 131.4, 131.4, 131.0, 129.6, 127.5, 124.1, 123.6, 122.6, 122.2, 121.5, 118.9, 118.6, 111.9, 111.3, 108.8, 73.2, 46.6, 40.5, 23.2. FTIR (neat, cm$^{-1}$) 3328, 2914, 1704, 1679, 1614, 1468, 1339, 1165, 1074, 740. HRMS (ESI, m/z) calculated for C$_{26}$H$_{22}$N$_2$O$_3$Br [M+H]$^+$: 489.0814. found 489.0824 and for C$_{26}$H$_{21}$N$_2$O$_3$BrNa [M+Na]$^+$: 511.0633. found 511.0635. Flash chromatography conditions: 25 g column, flow rate 18 mL/min, 100/0 to 50/50 cyclohexane/EtOAc. R$_f$=0.45, 50/50 cyclohexane/EtOAc.

1-(3-Ethyl(1H)indol-3-yl)-3-hydroxy-3-(2-oxo-2-(4-(trifluoromethoxy)phenyl)ethyl)indol-2-one (APV-ST427)

The compound APV-ST427 was prepared by following the general procedure D, using 1-(3-ethyl(1H)indol-3-yl)indole-2,3-dione (80 mg, 0.28 mmol) and 4'-(trifluoromethoxy)acetophenone (62 μL, 0.39 mmol). The compound indicated in the title was obtained after flash chromatography followed by trituration in pentane, in the form of a beige-colored solid (109 mg). Yield=80%. m.p.=154.4-156.2° C. $^1$H NMR (300 MHz, DMSO-d$_6$, δ ppm) 10.88 (s, 1H), 8.03 (d, J=8.6 Hz, 2H), 7.64 (d, J=7.7 Hz, 1H), 7.47 (d, J=8.6 Hz, 2H), 7.41-7.33 (m, 2H), 7.31 (br. s, 1H), 7.29-7.22 (m, 1H), 7.15-6.90 (m, 4H), 6.21 (s, 1H), 4.14 (d, J=17.4 Hz, 1H), 4.07-3.78 (m, 2H), 3.67 (d, J=17.4 Hz, 1H), 3.06 (t, J=7.9 Hz, 2H). $^{13}$C NMR (75 MHz, DMSO-d$_6$, δ ppm) 195.8, 176.9, 152.1, 144.0, 136.7, 135.4, 131.4, 131.0, 131.0, 129.6, 127.5, 124.0, 123.6, 122.2, 121.5, 121.1, 121.1, 118.9, 118.6, 111.9, 111.3, 108.8, 73.2, 46.6, 40.5, 23.2. NB: The carbon alpha to the fluorines (—CF3) is not visible. $^{19}$F NMR (188 MHz, DMSO-d$_6$, δ ppm) −57.0. FTIR (neat, cm$^{-1}$) 3334, 1703, 1681, 1260, 1214, 1168, 1066, 741. HRMS (ESI, m/z) calculated for C$_{27}$H$_{22}$N$_2$O$_4$F$_3$ [M+H]$^+$: 495.1532. found 495.1541 and for C$_{27}$H$_{21}$N$_2$O$_4$F$_3$Na [M+Na]$^+$: 517.1351. found 517.1347. Flash chromatography conditions: 10 g column, flow rate 8 mL/min, 100/0 to 50/50 cyclohexane/EtOAc. R$_f$=0.49, 50/50 cyclohexane/EtOAc.

1-(3-Ethyl(1H)indol-3-yl)-3-hydroxy-3-(2-oxo-2-(3-(trifluoromethyl)phenyl)ethyl)indol-2-one (APV-ST363)

The compound APV-ST363 was prepared by following the general procedure D, using 1-(3-ethyl(1H)indol-3-yl)

indole-2,3-dione (80 mg, 0.28 mmol) and 3'-(trifluoromethyl)acetophenone (59 µL, 0.39 mmol). The compound indicated in the title was obtained after flash chromatography followed by trituration in pentane, in the form of a beige-colored solid (92 mg). Yield=70%. m.p.=113.2-114.8° C. $^1$H NMR (300 MHz, DMSO-d$_6$, δ ppm) 10.89 (s, 1H), 8.21 (d, J=8.0 Hz, 1H), 8.14 (s, 1H), 8.00 (d, J=7.7 Hz, 1H), 7.81-7.69 (m, 1H), 7.64 (d, J=7.6 Hz, 1H), 7.43-7.34 (m, 2H), 7.32-7.24 (m, 2H), 7.13-6.92 (m, 4H), 6.23 (s, 1H), 4.22 (d, J=17.4 Hz, 1H), 4.05-3.80 (m, 2H), 3.72 (d, J=17.4 Hz, 1H), 3.05 (t, J=7.8 Hz, 2H). $^{13}$C NMR (75 MHz, DMSO-d$_6$, δ ppm) 195.7, 176.3, 143.4, 136.8, 136.3, 132.1, 130.9, 130.1, 129.9-129.5 (m, CH fluorine coupled), 129.2, 127.1, 124.5-124.2 (m, CH fluorine coupled), 123.7, 123.2, 121.8, 121.0, 118.4, 118.1, 111.5, 110.8, 108.4, 72.7, 46.2, 40.1, 22.8. NB: The quaternary carbons alpha and beta to the fluorines are not visible (—C—CF3). $^{19}$F NMR (188 MHz, DMSO-d$_6$, δ ppm) −61.7. FTIR (neat, cm$^{-1}$) 3307, 1690, 1615, 1468, 1352, 1201, 1168, 1127, 1072, 744. HRMS (ESI, m/z) calculated for $C_{27}H_{22}N_2O_3F_3$ [M+H]$^+$: 479.1583. found 479.1588 and for $C_{27}H_{21}N_2O_3F_3Na$ [M+Na]$^+$: 501.1402. found 501.1400. Flash chromatography conditions: 10 g column, flow rate 8 mL/min, 100/0 to 50/50 cyclohexane/EtOAc. R$_f$=0.19, 50/50 cyclohexane/EtOAc.

1-(3-Ethyl(1H)indol-3-yl)-3-hydroxy-3-(2-oxo-2-(2-fluorophenyl)ethyl)indol-2-one (APV-ST416)

The compound APV-ST416 was prepared by following the general procedure D, using 1-(3-ethyl(1H)indol-3-yl)indole-2,3-dione (80 mg, 0.28 mmol) and 2'-fluoroacetophenone (47 µL, 0.39 mmol). The compound indicated in the title was obtained after flash chromatography followed by trituration in pentane, in the form of a beige-colored solid (89 mg). Yield=75%. m.p.=180.0-181.8° C. $^1$H NMR (300 MHz, DMSO-d$_6$, δ ppm) 10.88 (s, 1H), 7.76-7.54 (m, 3H), 7.47-7.20 (m, 6H), 7.14-6.91 (m, 4H), 6.19 (s, 1H), 4.01 (d, J=17.9 Hz, 1H), 4.10-3.82 (m, 2H), 3.68 (d, J=17.8 Hz, 1H), 3.05 (t, J=7.9 Hz, 2H). 13C NMR (75 MHz, DMSO-d$_6$, b ppm) 194.78, 176.77, 161.48 (d, J=254.2 Hz), 144.02, 136.72, 135.84 (d, J=9.0 Hz), 131.36, 130.51, 129.63, 127.53, 125.25 (d, J=3.4 Hz), 123.91, 123.62, 122.17 (d, J=8.0 Hz), 121.47, 118.87, 118.55, 117.33 (d, J=23.2 Hz), 111.92, 111.28, 108.83, 72.95, 50.83, 40.53, 23.19. NB: The quaternary carbon located alpha to the C=O and C—F is not visible. $^{19}$F NMR (188 MHz, DMSO-d$_6$, δ ppm) −107.9. FTIR (neat, cm$^{-1}$) 3330, 1702, 1608, 1470, 1450, 1342, 1172, 1060, 745. HRMS (ESI, m/z) calculated for $C_{26}H_{22}N_2O_3F$ [M+H]$^+$: 429.1614. found 429.1614. Flash chromatography conditions: 25 g column, flow rate 18 mL/min, 100/0 to 50/50 cyclohexane/EtOAc. R$_f$=0.47, 50/50 cyclohexane/EtOAc.

1-(3-Ethyl(1H)indol-3-yl)-3-hydroxy-3-(2-oxo-2-(3-fluorophenyl)ethyl)indol-2-one (APV-ST372)

The compound APV-ST372 was prepared by following the general procedure D, using 1-(3-ethyl(1H)indol-3-yl)indole-2,3-dione (80 mg, 0.28 mmol) and 3'-fluoroacetophenone (48 µL, 0.39 mmol). The compound indicated in the title was obtained after flash chromatography followed by trituration in pentane, in the form of a beige-colored solid (88 mg). Yield=75%. m.p.=107.5-109.2° C. $^1$H NMR (300 MHz, DMSO-d$_6$, δ ppm) 10.89 (s, 1H), 7.76 (d, J=7.6 Hz, 1H), 7.69-7.62 (m, 2H), 7.60-7.44 (m, 2H), 7.37 (d, J=7.6 Hz, 2H), 7.32-7.23 (m, 2H), 7.16-6.90 (m, 4H), 6.20 (s, 1H), 4.14 (d, J=17.5 Hz, 1H), 4.04-3.84 (m, 2H), 3.66 (d, J=17.5 Hz, 1H), 3.06 (t, J=7.8 Hz, 2H). $^{13}$C NMR (75 MHz, DMSO-d$_6$, δ ppm) 195.54, 176.40, 162.12 (d, J$_{C-F}$=245.3 Hz), 143.54, 138.30 (d, J$_{C-F}$=6.2 Hz), 136.27, 130.97, 130.93 (d, J$_{C-F}$=6.8 Hz), 129.19, 127.09, 124.27 (d, J$_{C-F}$=3.4 Hz), 123.56, 123.19, 121.74, 121.02, 120.36 (d, J$_{C-F}$=21.3 Hz), 118.43, 118.11, 114.46 (d, J$_{C-F}$=22.4 Hz), 111.48, 110.83, 108.38, 72.70, 46.24, 40.07, 22.76. $^{19}$F NMR (188 MHz, DMSO-d$_6$, δ ppm) −109.6. FTIR (neat, cm$^{-1}$) 3314, 2943, 1682, 1614, 1468, 1340, 1247, 1167, 1060, 739. HRMS (ESI, m/z) calculated for $C_{26}H_{22}N_2O_3F$ [M+H]$^+$: 429.1614. found 429.1607 and for $C_{26}H_{21}N_2O_3FNa$ [M+Na]$^+$: 451.1434. found 451.1432. Flash chromatography conditions: 25 g column, flow rate 18 mL/min, 100/0 to 50/50 cyclohexane/EtOAc. R$_f$=0.46, 50/50 cyclohexane/EtOAc.

1-(3-Ethyl(1H)indol-3-yl)-3-hydroxy-3-(2-oxo-2-(4-fluorophenyl)ethyl)indol-2-one (APV-ST417)

The compound APV-ST417 was prepared by following the general procedure D, using 1-(3-ethyl(1H)indol-3-yl)indole-2,3-dione (80 mg, 0.28 mmol) and 4'-fluoroacetophenone (47 µL, 0.39 mmol). The compound indicated in the title was obtained after flash chromatography followed by trituration in pentane, in the form of a beige-colored solid (100 mg). Yield=85%. m.p.=113.3-115.2° C. $^1$H NMR (300 MHz, DMSO-d$_6$, δ ppm) 10.88 (s, 1H), 8.02-7.93 (m, 2H), 7.64 (d, J=7.2 Hz, 1H), 7.40-7.22 (m, 6H), 7.14-6.90 (m, 4H), 6.17 (s, 1H), 4.12 (d, J=17.4 Hz, 1H), 4.02-3.83 (m, 2H), 3.64 (d, J=17.4 Hz, 1H), 3.06 (d, J=8.0 Hz, 2H), $^{13}$C NMR (75 MHz, DMSO-d$_6$, δ ppm) 195.1, 176.4, 165.1 (d, J$_{C-F}$=252.0 Hz), 143.5, 136.3, 132.9 (d, J$_{C-F}$=2.5 Hz), 131.1, 131.0 (d, J$_{C-F}$=9.1 Hz, 2*CH), 129.1, 127.1, 123.5, 123.2, 121.7, 121.0, 118.4, 118.1, 115.7 (d, J$_{C-F}$=21.9 Hz, 2*CH), 111.6, 110.8, 108.3, 72.7, 46.0, 40.1, 22.7. $^{19}$F NMR (188 MHz, DMSO-d$_6$, δ ppm) −103.7. FTIR (neat, cm$^{-1}$) 3371, 3057, 1682, 1614, 1596, 1340, 1227, 1157, 841, 739. HRMS (ESI, m/z) calculated for $C_{26}H_{22}N_2O_3F$ [M+H]$^+$: 429.1614. found 429.1609 and for $C_{26}H_{21}N_2O_3FNa$ [M+Na]$^+$: 451.1434. found 451.1430. Flash chromatography conditions: 25 g column, flow rate 18 mL/min, 100/0 to 50/50 cyclohexane/EtOAc. R$_f$=0.38, 50/50 cyclohexane/EtOAc.

1-(3-Ethyl-1-methyl(1H)indol-3-yl)-3-hydroxy-3-(2-oxo-2-(2-chlorophenyl)ethyl)indol-2-one (APV-ST521)

The compound APV-ST521 was prepared by following the general procedure D, using 1-(3-ethyl-1-methyl(1H)indol-3-yl)indole-2,3-dione (45 mg, 0.15 mmol) and 2'-chloroacetophenone (39 µL, 0.21 mmol). The compound indicated in the title was obtained after flash chromatography followed by trituration in pentane, in the form of a beige-colored solid (40 mg). Yield=60%. m.p.=149.8-151.8° C. $^1$H NMR (300 MHz, DMSO-d$_6$, δ ppm) 7.64 (d, J=7.7 Hz, 1H), 7.52-7.36 (m, 6H), 7.28 (d, J=6.0 Hz, 2H), 7.20-7.13 (m, 1H), 7.09-6.95 (m, 3H), 6.24 (s, 1H), 3.98-3.83 (m, 3H), 3.62 (d, J=16.5 Hz, 1H), 3.32 (s, 3H), 3.01 (t, J=7.6 Hz, 2H). $^{13}$C NMR (75 MHz, DMSO-d$_6$, δ ppm) 198.6, 176.1, 143.3, 137.9, 136.7, 132.5, 130.4, 130.4, 129.6, 129.3, 129.2, 127.6, 127.4, 127.3, 123.8, 121.9, 121.1, 118.5, 118.3, 110.1, 109.7, 108.5, 72.8, 49.8, 40.1, 32.3, 22.5. FTIR (neat, cm$^{-1}$) 3334, 1686, 1614, 1470, 1394, 1370, 1118, 992, 831, 731. HRMS (ESI, m/z) calculated for $C_{27}H_{23}N_2O_3ClNa$ [M+Na]$^+$: 481.1295. found 481.1292. Flash chromatography conditions: 12 g column, flow rate 15 mL/min, 100/0 to 60/40 cyclohexane/EtOAc. R$_f$=0.54, 50/50 cyclohexane/EtOAc.

1-(3-Propyl(1H)indol-3-yl)-3-hydroxy-3-(2-oxo-2-phenylethyl)indol-2-one (APV-ST389)

The compound APV-ST389 was prepared by following the general procedure D, using 1-(3-propyl(1H)indol-3-yl)indol-2,3-dione (80 mg, 0.26 mmol) and acetophenone (43 µL, 0.37 mmol). The compound indicated in the title was obtained after flash chromatography followed by trituration in pentane, in the form of a beige-colored solid (100 mg). Yield=90%. m.p.=120.9-122.8° C. $^1$H NMR (300 MHz, DMSO-d$_6$, δ ppm) 10.78 (s, 1H), 7.87 (d, J=7.5 Hz, 2H), 7.65-7.54 (m, 2H), 7.52-7.45 (m, 2H), 7.35 (d, J=7.6 Hz, 2H), 7.26-7.17 (m, 2H), 7.10-7.04 (m, 1H), 6.97 (d, J=7.7 Hz, 2H), 6.95-6.89 (m, 1H), 6.15 (s, 1H), 4.14 (d, J=17.6 Hz, 1H), 3.85-3.72 (m, 2H), 3.68 (d, J=17.6 Hz, 1H), 2.83 (t, J=7.6 Hz, 2H), 2.09-1.96 (m, 2H). $^{13}$C NMR (75 MHz, DMSO-d$_6$, δ ppm) 196.9, 177.1, 144.3, 136.8, 136.5, 133.9, 131.7, 129.5, 129.2, 129.2, 128.3, 128.3, 127.6, 123.8, 122.7, 122.1, 121.3, 118.8, 118.5, 114.5, 111.8, 108.8, 73.1, 46.5, 39.7, 28.3, 22.6. FTIR (neat, cm$^{-1}$) 3294, 2926, 1682, 1613, 1468, 1339, 1213, 1162, 1065, 739. HRMS (ESI, m/z) calculated for C$_{27}$H$_{25}$N$_2$O$_3$ [M+H]$^+$: 425.1865. found 425.1870. Flash chromatography conditions: 25 g column, flow rate 18 mL/min, 100/0 to 50/50 cyclohexane/EtOAc. R$_f$=0.32, 50/50 cyclohexane/EtOAc.

1-(3-Propyl(1H)indol-3-yl)-3-hydroxy-3-(2-oxo-2-(2-chlorophenyl)ethyl)indol-2-one (APV-ST388)

The compound APV-ST388 was prepared by following the general procedure D, using 1-(3-propyl(1H)indol-3-yl)indole-2,3-dione (80 mg, 0.26 mmol) and 2'-chloroacetophenone (48 µL, 0.37 mmol). The compound indicated in the title was obtained after flash chromatography followed by trituration in pentane, in the form of a beige-colored solid (83 mg). Yield=69%. m.p.=126.2-127.8° C., $^1$H NMR (300 MHz, DMSO-d$_6$, δ ppm) 10.76 (s, 1H), 7.53 (d, J=7.8 Hz, 1H), 7.49-7.43 (m, 3H), 7.40-7.32 (m, 3H), 7.29-7.23 (m, 1H), 7.17 (br, s, 1H), 7.09-7.03 (m, 1H), 7.00-6.92 (m, 3H), 6.22 (s, 1H), 3.93 (d, J=17.0 Hz, 1H), 3.83-3.67 (m, 2H), 3.62 (d, J=16.8 Hz, 1H), 2.87-2.76 (m, 2H), 2.06-1.96 (m, 2H), $^{13}$C NMR (75 MHz, DMSO-d$_6$, δ ppm) 199.0, 176.7, 144.1, 138.4, 136.8, 132.9, 131.0, 130.9, 130.1, 129.7, 129.7, 127.8, 127.6, 124.1, 122.7, 122.2, 121.3, 118.8, 118.5, 114.4, 111.8, 109.0, 73.2, 50.3, 39.7, 28.2, 22.6. FTIR (neat, cm$^{-1}$) 3293, 3229, 2929, 1695, 1680, 1616, 1468, 1354, 1164, 1059, 739. HRMS (ESI, m/z) calculated for C$_{27}$H$_{24}$N$_2$O$_3$Cl [M+H]$^+$: 459.1475. found 459.1472. Flash chromatography conditions: 25 g column, flow rate 18 mL/min, 100/0 to 50/50 cyclohexane/EtOAc. R$_f$=0.38, 50/50 cyclohexane/EtOAc.

1-(3-Propyl(1H)indol-3-yl)-3-hydroxy-3-(2-oxo-2-(3-chlorophenyl)ethyl)indol-2-one (APV-ST387)

The compound APV-ST387 was prepared by following the general procedure D, using 1-(3-propyl(1H)indol-3-yl)indol-2,3-dione (80 mg, 0.26 mmol) and 3'-chloroacetophenone (48 µL, 0.37 mmol). The compound indicated in the title was obtained after flash chromatography followed by trituration in pentane, in the form of a beige-colored solid (93 mg). Yield=72%. m.p.=126.0-127.9° C. $^1$H NMR (300 MHz, DMSO-d$_6$, δ ppm) 10.77 (s, 1H), 7.85 (s, 1H), 7.84 (d, J=7.1 Hz, 1H), 7.69 (d, J=7.5 Hz, 1H), 7.55 (d, J=7.6 Hz, 1H), 7.50 (d, J=8.2 Hz, 1H), 7.36 (d, J=3.2 Hz, 1H), 7.33 (d, J=3.7 Hz, 1H), 7.27-7.20 (m, 1H), 7.17 (d, J=2.3 Hz, 1H), 7.10-7.03 (m, 1H), 6.97 (d, J=7.9 Hz, 2H), 6.92 (d, J=7.8 Hz, 1H), 6.15 (s, 1H), 4.14 (d, J=17.5 Hz, 1H), 3.86-3.60 (m, 2H), 3.66 (d, J=17.5 Hz, 1H), 2.89-2.76 (m, 2H), 2.09-1.92 (m, 2H), $^{13}$C NMR (75 MHz, DMSO-d$_6$, δ ppm) 196.0, 177.05, 144.2, 138.3, 136.8, 134.1, 133.6, 131.5, 131.2, 129.6, 128.0, 127.6, 127.1, 123.9, 122.7, 122.1, 121.3, 118.8, 118.5, 114.5, 111.8, 108.8, 73.1, 46.6, 39.7, 28.3, 22.6. FTIR (neat, cm$^{-1}$) 3341, 2920, 1687, 1613, 1468, 1338, 1209, 1163, 1082, 781, 740. HRMS (ESI, m/z) calculated for C$_{27}$H$_{24}$N$_2$O$_3$C [M+H]$^+$: 459.1475. found 459.1478. Flash chromatography conditions: 25 g column, flow rate 18 mL/min, 100/0 to 50/50 cyclohexane/EtOAc. R$_f$=0.37, 50/50 cyclohexane/EtOAc.

1-(3-Propyl(1H)indol-3-yl)-3-hydroxy-3-(2-oxo-2-(4-chlorophenyl)ethyl)indol-2-one (APV-ST413)

The compound APV-ST413 was prepared by following the general procedure D, using 1-(3-propyl(1H)indol-3-yl)indole-2,3-dione (80 mg, 0.26 mmol) and 4'-chloroacetophenone (48 µL, 0.37 mmol). The compound indicated in the title was obtained after flash chromatography followed by trituration in pentane, in the form of a beige-colored solid (119 mg). Yield=99%. m.p.=129.8-131.7° C. $^1$H NMR (300 MHz, DMSO-d$_6$, δ ppm) 10.77 (s, 1H), 7.88 (d, J=8.2 Hz, 2H), 7.54 (d, J=7.9 Hz, 3H), 7.34 (d, J=7.9 Hz, 2H), 7.27-7.19 (m, 1H), 7.18 (s, 1H), 7.10-7.02 (m, 1H), 6.99-6.90 (m 3H), 6.16 (s, 1H), 4.11 (d, J=17.8 Hz, 1H), 3.84-3.67 (m, 2H), 3.64 (d, J=17.6 Hz, 1H), 2.82 (t, J=7.5 Hz, 2H), 2.07-1.95 (m, 2H). $^{13}$C NMR (75 MHz, DMSO-d$_6$, δ ppm) 196.0, 177.0, 144.2, 138.8, 136.8, 135.2, 131.5, 130.3, 130.3, 129.5, 129.2, 129.2, 127.6, 123.9, 122.7, 122.1, 121.3, 118.8, 118.5, 114.5, 111.8, 108.8, 73.1, 46.5, 39.7, 28.2, 22.6. FTIR (neat, cm$^{-1}$) 3393, 2921, 1681, 1614, 1588, 1468, 1356, 1213, 1092, 990, 740. HRMS (ESI, m/z) calculated for C$_{27}$H$_{24}$N$_2$O$_3$Cl [M+H]$^+$: 459.1475. found 459.1479 and for C$_{27}$H$_{23}$N$_2$O$_3$Cl Na [M+Na]$^+$: 481.1295. found 481.1297. Flash chromatography conditions: 25 g column, flow rate 18 mL/min, 100/0 to 50/50 cyclohexane/EtOAc. R$_f$=0.38, 50/50 cyclohexane/EtOAc.

1-(3-Propyl(1H)indol-3-yl)-3-hydroxy-3-(2-oxo-2-(3-methylphenyl)ethyl)indol-2-one (APV-ST414)

The compound APV-ST414 was prepared by following the general procedure D, using 1-(3-propyl(1H)indol-3-yl)indole-2,3-dione (80 mg, 0.26 mmol) and 3'-methylacetophenone (50 µL, 0.37 mmol). The compound indicated in the title was obtained after flash chromatography followed by trituration in pentane, in the form of a beige-colored solid (114 mg). Yield=99%. m.p.=92.2-94.2° C. $^1$H NMR (300 MHz, DMSO-d$_6$, δ ppm) 10.78 (s, 1H), 7.68 (s, 2H), 7.57 (d, J=7.7 Hz, 1H), 7.45-7.32 (m, 4H), 7.26-7.18 (m, 2H), 7.11-7.04 (m, 1H), 7.01-6.89 (m, 3H), 6.14 (s, 1H), 4.12 (d, J=17.6 Hz, 1H), 3.88-3.62 (m, 2H), 3.66 (d, J=17.7 Hz, 1H), 2.84 (t, J=7.3 Hz, 2H), 2.33 (s, 3H), 2.11-1.95 (m, 2H). $^{13}$C NMR (75 MHz, DMSO-d$_6$, δ ppm) 196.9, 177.1, 144.4, 138.5, 136.8, 136.6, 134.5, 131.7, 129.5, 129.0, 128.8, 127.6, 125.6, 123.7, 122.7, 122.1, 121.3, 118.8, 118.5, 114.5, 111.8, 108.8, 73.1, 46.6, 39.7, 28.3, 22.6, 21.2. FTIR (neat, cm$^{-1}$) 3350, 2929, 1680, 1613, 1468, 1339, 1249, 1163, 1083, 739. HRMS (ESI, m/z) calculated for C$_{28}$H$_{27}$N$_2$O$_3$ [M+H]$^+$: 439.2022. found 439.2026 and for C$_{28}$H$_{26}$N$_2$O$_3$Na [M+Na]$^+$: 461.1814. found 461.1842. Flash chromatography conditions: 25 g column, flow rate 18 mL/min, 100/0 to 50/50 cyclohexane/EtOAc. R$_f$=0.36, 50/50 cyclohexane/EtOAc.

1-(3-Propyl(1H)indol-3-yl)-3-hydroxy-3-(2-oxo-2-(3-fluorophenyl)ethyl)indol-2-one (APV-ST407)

The compound APV-ST407 was prepared by following the general procedure D, using 1-(3-propyl(1H)indol-3-yl)indole-2,3-dione (80 mg, 0.26 mmol) and 3'-fluoroacetophenone (45 μL, 0.37 mmol). The compound indicated in the title was obtained after flash chromatography followed by trituration in pentane, in the form of a beige-colored solid (110 mg). Yield=95%. m.p.=104-105.9° C. $^1$H NMR (300 MHz, DMSO-d$_6$, δ ppm) 10.78 (s, 1H), 7.75 (d, J=7.5 Hz, 1H), 7.63 (d, J=9.6 Hz, 1H), 7.59-7.43 (m, 3H), 7.35 (d, J=7.6 Hz, 2H), 7.27-7.17 (m, 2H), 7.10-7.03 (m, 1H), 7.01-6.90 (m, 3H), 6.17 (s, 1H), 4.15 (d, J=17.7 Hz, 1H), 3.87-3.66 (m, 3H), 3.68 (d, J=17.6 Hz, 1H), 2.83 (t, J=7.6 Hz, 2H), 2.11-1.95 (m, 2H). $^{13}$C NMR (75 MHz, DMSO-d$_6$, δ ppm) 195.5, 176.5, 162.1 (d, $J_{C-F}$=245.1 Hz), 143.8, 138.2 (d, $J_{C-F}$=5.5 Hz), 136.3, 131.0, 130.9 (d, $J_{C-F}$=7.6 Hz), 129.1, 127.1, 124.2 (d, $J_{C-F}$=2.0 Hz), 123.4, 122.3, 121.7, 120.8, 120.3 (d, $J_{C-F}$=21.7 Hz), 118.3, 118.0, 114.4 (d, $J_{C-F}$=22.3 Hz), 114.0, 111.3, 108.4, 72.6, 46.2, 39.3, 27.8, 22.1. $^{19}$F NMR (188 MHz, DMSO-d$_6$, δ ppm) −112.1. FTIR (neat, cm$^{-1}$) 3343, 2907, 1687, 1613, 1339, 1248, 1167, 739. HRMS (ESI, m/z) calculated for $C_{27}H_{24}N_2O_3F$ [M+H]$^+$: 443.1771. found 443.1763 and for $C_{27}H_{23}N_2O_3FNa$ [M+Na]$^+$: 465.1590. found 465.1581. Flash chromatography conditions: 25 g column, flow rate 18 mL/min, 100/0 to 50/50 cyclohexane/EtOAc. $R_f$=0.49, 50/50 cyclohexane/EtOAc.

1-(3-Propyl(1H)indol-3-yl)-3-hydroxy-3-(2-oxo-2-(4-fluorophenyl)ethyl)indol-2-one (APV-ST412)

The compound APV-ST412 was prepared by following the general procedure D, using 1-(3-propyl(1H)indol-3-yl)indole-2,3-dione (80 mg, 0.26 mmol) and 4'-fluoroacetophenone (45 μL, 0.37 mmol). The compound indicated in the title was obtained after flash chromatography followed by trituration in pentane, in the form of a beige-colored solid (99 mg). Yield=85%. m.p.=94.4-96.2° C. $^1$H NMR (300 MHz, DMSO-d$_6$, δ ppm) 10.78 (s, 1H), 7.98 (d, J=5.7 Hz, 1H), 7.95 (d, J=5.5 Hz, 1H), 7.56 (d, J=7.8 Hz, 1H), 7.37-7.17 (m, 6H), 7.11-7.04 (m, 1H), 7.01-6.89 (m, 3H), 6.16 (s, 1H), 4.12 (d, J=17.6 Hz, 1H), 3.88-3.67 (m, 2H), 3.66 (d, J=17.6 Hz, 1H), 2.83 (t, J=7.5 Hz, 2H), 2.09-1.96 (m, 2H). $^{13}$C NMR (75 MHz, DMSO-d$_6$, δ ppm) 195.03, 176.56, 165.10 (d, J=252.1 Hz), 143.81, 136.30, 132.85 (d, J=1.9 Hz), 131.14, 131.02, 130.90, 129.04, 127.13, 123.34, 122.26, 121.62, 120.84, 118.20 (d, J=20.8 Hz, 2*CH), 115.67 (d, J=21.9 Hz, 2*CH), 114.01, 111.32, 108.35, 72.63, 45.98, 39.24, 27.79, 22.13. $^{19}$F NMR (188 MHz, DMSO-d$_6$, δ ppm) −103.8. FTIR (neat, cm$^{-1}$) 3371, 2914, 1681, 1614, 1596, 1468, 1339, 1227, 1157, 1083, 992, 740. HRMS (ESI, m/z) calculated for $C_{27}H_{24}N_2O_3F$ [M+H]$^+$: 443.1771. found 443.1768 and for $C_{27}H_{23}N_2O_3FNa$ [M+Na]$^+$: 465.1590. found 465.1597. Flash chromatography conditions: 25 g column, flow rate 18 mL/min, 100/0 to 50/50 cyclohexane/EtOAc. $R_f$=0.51, 50/50 cyclohexane/EtOAc.

1-(3-Propyl(1H)indol-3-yl)-3-hydroxy-3-(2-oxo-2-((3-trifluoromethyl)phenyl)ethyl)indol-2-one (APV-ST420)

The compound APV-ST420 was prepared by following the general procedure D, using 1-(3-propyl(1H)indol-3-yl)indole-2,3-dione (80 mg, 0.26 mmol) and 3'-(trifluoromethyl)acetophenone (56 μL, 0.37 mmol). The compound indicated in the title was obtained after flash chromatography followed by trituration in pentane, in the form of a beige-colored solid (96 mg). Yield=71%. m.p.=97.7-99.6° C. $^1$H NMR (300 MHz, DMSO-d$_6$, δ ppm) 10.77 (s, 1H), 8.19 (d, J=7.9 Hz, 1H), 8.11 (s, 1H), 7.98 (d, J=7.5 Hz, 1H), 7.78-7.69 (m, 1H), 7.55 (d, J=7.8 Hz, 1H), 7.36 (d, J=5.8 Hz, 1H), 7.34 (d, J=7.2 Hz, 1H), 7.27-7.20 (m, 1H), 7.18 (br. s, 1H), 7.11-7.01 (m, 1H), 7.01-6.89 (m, 3H), 6.19 (s, 1H), 4.22 (d, J=17.6 Hz, 1H), 3.86-3.66 (m, 2H), 3.73 (d, J=17.6 Hz, 1H), 2.82 (t, J=7.4 Hz, 2H), 2.10-1.93 (m, 2H), $^{13}$C NMR (75 MHz, DMSO-d$_6$, δ ppm) 195.6, 176.4, 143.7, 136.7, 136.3, 132.0, 131.0, 130.1, 129.9-129.6 (m, CH fluorine coupled), 129.1, 127.1, 124.5-124.1 (m, CH fluorine coupled), 123.5, 122.2, 121.7, 120.8, 118.3, 118.0, 114.0, 111.3, 108.4, 72.7, 46.2, 39.3, 27.8, 22.1. NB: The quaternary carbons alpha and beta to the fluorines are not visible (—C—CF3). $^{19}$F NMR (188 MHz, DMSO-d$_6$, δ ppm) −61.7, FTIR (neat, cm$^{-1}$) 3368, 3941, 1690, 1612, 1324, 1201, 1165, 1122, 1070, 740. HRMS (ESI, m/z) calculated for $C_{28}H_{23}N_2O_3F_3Na$ [M+Na]$^+$: 515.1558. found 515.1554. Flash chromatography conditions: 25 g column, flow rate 18 mL/min, 100/0 to 50/50 cyclohexane/EtOAc. $R_f$=0.40, 50/50 cyclohexane/EtOAc.

1-(5-Chloro-3-propyl(1H)indol-3-yl)-3-hydroxy-3-(2-oxo-2-phenylethyl)indol-2-one (APV-ST297)

The compound APV-ST297 was prepared by following the general procedure D, using 1-(5-chloro-3-propyl(1H)indol-3-yl)indol-2,3-dione (38 mg, 0.11 mmol) and acetophenone (18 μL, 0.16 mmol). The compound indicated in the title was obtained after flash chromatography followed by trituration in pentane, in the form of a beige-colored solid (30 mg). Yield=60%. m.p.=170.7-172.4° C. $^1$H NMR (300 MHz, DMSO-d$_6$, δ ppm) 10.99 (s, 1H), 7.89 (d, J=7.8 Hz, 2H), 7.68-7.55 (m, 2H), 7.48 (d, J=7.5 Hz, 1H), 7.46 (d, J=7.7 Hz, 1H), 7.36 (d, J=2.9 Hz, 1H), 7.34 (s, 1H), 7.30-7.20 (m, 2H), 7.05 (dd, J=8.3, 1.5 Hz, 1H), 7.02-6.87 (m, 2H), 6.14 (s, 1H), 4.14 (d, J=17.7 Hz, 1H), 3.89-3.62 (m, 2H), 3.68 (d, J=17.6 Hz, 1H), 2.91-2.72 (m, 2H), 2.08-1.94 (m, 2H). $^{13}$C NMR (75 MHz, DMSO-d$_6$, b ppm) 196.9, 177.1, 144.3, 136.5, 135.2, 133.9, 131.7, 129.5, 129.1, 129.1, 128.8, 128.4, 128.4, 124.7, 123.8, 123.3, 122.1, 121.2, 118.1, 114.6, 113.3, 108.8, 73.1, 46.5, 39.6, 28.3, 22.3. FTIR (neat, cm$^{-1}$) 3301, 2930, 1693, 1613, 1491, 1468, 1349, 1215, 1162, 796. HRMS (ESI, m/z) calculated for $C_{27}H_{23}N_2O_3C$ [M+H]$^+$: 459.1475. found 459.1469 and for $C_{27}H_{23}N_2O_3ClNa$ [M+Na]$^+$: 481.1295. found 481.1292. Flash chromatography conditions: 25 g column, flow rate 18 mL/min, 100/0 to 50/50 cyclohexane/EtOAc. $R_f$=0.33, 50/50 cyclohexane/EtOAc.

1-(5-Chloro-3-propyl(1H)indol-3-yl)-3-hydroxy-3-(2-oxo-2-(2-chlorophenyl)ethyl)indol-2-one (APV-ST385)

The compound APV-ST385 was prepared by following the general procedure D, using 1-(5-chloro-3-propyl(1H)indol-3-yl)indole-2,3-dione (125 mg, 0.37 mmol) and 2'-chloroacetophenone (69 μL, 0.52 mmol). The compound indicated in the title was obtained after flash chromatography followed by trituration in pentane, in the form of a beige-colored solid (115 mg). Yield=63%. m.p.=135.2-137.1° C. $^1$H NMR (300 MHz, DMSO-d$_6$, δ ppm) 10.98 (s, 1H), 7.56 (s, 1H), 7.50-7.42 (m, 3H), 7.41-7.32 (m, 3H), 7.30-7.22 (m, 2H), 7.05 (dd, J=8.5, 1.3 Hz, 1H), 7.02-6.93 (m, 2H), 6.22 (s, 1H), 3.94 (d, J=16.9 Hz, 1H), 3.84-3.67 (m, 2H), 3.63 (d, J=17.0 Hz, 1H), 2.80 (t, J=7.4 Hz, 2H), 2.05-1.91 (m, 2H). $^{13}$C NMR (75 MHz, DMSO-d$_6$, δ ppm) 199.1, 176.7, 144.1, 138.4, 135.2, 132.9, 131.0, 130.9, 130.1, 129.7, 129.7, 128.7, 127.7, 124.7, 124.1, 123.3, 122.3, 121.2, 118.1, 114.5, 113.3, 109.0, 73.1, 50.3, 39.7, 28.2, 22.3. FTIR (neat, cm$^{-1}$) 3353, 1701, 16313, 1468, 1160, 1063, 892, 795, 752. HRMS (ESI, m/z) calculated for $C_{27}H_{23}N_2O_3Cl_2$ [M+H]$^+$: 493.1086. found 493.1076. Flash chromatography conditions: 25 g column, flow rate 18 mL/min, 100/0 to 50/50 cyclohexane/EtOAc. R$_f$=0.39, 50/50 cyclohexane/EtOAc.

1-(5-Chloro-3-propyl(1H)indol-3-yl)-3-hydroxy-3-(2-oxo-2-(3-chlorophenyl)ethyl)indol-2-one (APV-ST298)

The compound APV-ST298 was prepared by following the general procedure D, using 1-(5-chloro-3-propyl(1H) indol-3-yl)indole-2,3-dione (38 mg, 0.11 mmol) and 3'-chloroacetophenone (21 μL, 0.16 mmol). The compound indicated in the title was obtained after flash chromatography followed by trituration in pentane, in the form of a beige-colored solid (36 mg). Yield=65%. m.p.=96.1-98.0° C. $^1$H NMR (300 MHz, CDCl$_3$, δ ppm) 8.16 (s, 1H), 7.86 (s, 1H), 7.75 (d, J=7.8 Hz, 1H), 7.58-7.49 (m, 2H), 7.43-7.23 (m, 4H), 7.17-7.00 (m, 3H), 6.81 (d, J=7.8 Hz, 1H), 3.89-3.70 (m, 3H), 3.56 (d, J=17.3 Hz, 1H), 3.08 (br, s), 2.84 (t, J=7.6 Hz, 2H), 2.21-2.08 (m, 2H), $^{13}$C NMR (75 MHz, CDCl$_3$, δ ppm) 196.5, 176.4, 143.2, 137.8, 135.1, 134.7, 133.6, 130.1, 130.0, 129.8, 128.5, 128.2, 126.3, 124.9, 124.0, 123.3, 123.0, 122.2, 118.3, 114.9, 112.1, 109.0, 74.2, 45.1, 39.8, 27.2, 22.2. FTIR (neat, cm$^{-1}$) 3343, 2980, 1686, 1613, 1491, 1345, 1209, 1161, 1072, 782, 753. HRMS (ESI, m/z) calculated for $C_{27}H_{23}N_2O_3Cl_2$ [M+H]$^+$: 493.1086. found 493.1097 and for $C_{27}H_{22}N_2O_3Cl_2Na$ [M+Na]$^+$: 515.0905. found 515.0930. Flash chromatography conditions: 25 g column, flow rate 18 mL/min, 100/0 to 50/50 cyclohexane/EtOAc. R$_f$=0.32, 50/50 cyclohexane/EtOAc.

1-(5-Chloro-3-propyl(1H)indol-3-yl)-3-hydroxy-3-(2-oxo-2-(4-chlorophenyl)ethyl)indol-2-one (APV-ST422)

The compound APV-ST422 was prepared by following the general procedure D, using 1-(5-chloro-3-propyl(1H) indol-3-yl)indole-2,3-dione (80 mg, 0.24 mmol) and 4'-chloroacetophenone (43 μL, 0.33 mmol). The compound indicated in the title was obtained after flash chromatography followed by trituration in pentane, in the form of a beige-colored solid (84 mg). Yield=72%. m.p.=147.4-149.2° C. $^1$H NMR (300 MHz, DMSO-d$_6$, δ ppm) 11.01 (s, 1H), 7.90 (d, J=8.4 Hz, 2H), 7.59 (s, 1H), 7.53 (d, J=8.3 Hz, 2H), 7.41-7.32 (m, 2H), 7.28 (d, J=1.7 Hz, 1H), 7.23 (d, J=7.7 Hz, 1H), 7.06 (dd, J=8.6, 1.4 Hz, 1H), 7.01-6.91 (m, 2H), 6.19 (s, 1H), 4.14 (d, J=17.6 Hz, 1H), 3.88-3.59 (m, 2H), 3.67 (d, J=17.6 Hz, 1H), 2.84-2.76 (m, 2H), 2.08-1.94 (m, 2H). $^{13}$C NMR (75 MHz, DMSO-d$_6$, δ ppm) 196.0, 177.0, 144.2, 138.9, 135.2, 135.2, 131.5, 130.3, 130.3, 129.5, 129.2, 129.2, 128.8, 124.7, 123.8, 123.4, 122.1, 121.2, 118.1, 114.6, 113.3, 108.9, 73.1, 46.5, 39.7, 28.3, 22.3. FTIR (neat, cm$^{-1}$) 3368, 2941, 1680, 1613, 1588, 1467, 1342, 1212, 1092, 1066, 990, 794, 753. HRMS (ESI, m/z) calculated for $C_{27}H_{22}N_2O_3Cl_2Na$ [M+Na]$^+$: 515.0905 found 515.0911. Flash chromatography conditions: 25 g column, flow rate 18 mL/min, 100/0 to 50/50 cyclohexane/EtOAc. R$_f$=0.45, 50/50 cyclohexane/EtOAc.

1-(5-Chloro-3-propyl(1H)indol-3-yl)-3-hydroxy-3-(2-oxo-2-(pyrid-3-yl)ethyl)indol-2-one (APV-ST302)

The compound APV-ST302 was prepared by following the general procedure D, using 1-(5-chloro-3-propyl(1H) indol-3-yl)indole-2,3-dione (120 mg, 0.35 mmol) and 3'-acetylpyridine (55 μL, 0.50 mmol). The compound indicated in the title was obtained after flash chromatography followed by trituration in pentane, in the form of a beige-colored solid (107 mg). Yield=66%. m.p.=113.7-115.6° C. $^1$H NMR (300 MHz, DMSO-d$_6$, δ ppm) 11.00 (s, 1H), 9.06 (d, J=1.7 Hz, 1H), 8.76 (d, J=4.8 Hz, 1H), 8.20 (d, J=8.3 Hz, 1H), 7.58 (s, 1H), 7.50 (dd, J=8.1, 4.6 Hz, 1H), 7.37 (d, J=2.8 Hz, 1H), 7.35 (d, J=3.9 Hz, 1H), 7.32-7.20 (m, 2H), 7.12-6.87 (m, 3H), 6.18 (s, 1H), 4.18 (d, J=17.4 Hz, 1H), 3.90-3.59 (m, 2H), 3.69 (t, J=17.7 Hz, 1H), 2.80 (t, J=8.0 Hz, 2H), 1.99 (t, J=6.3 Hz, 2H). $^{13}$C NMR (75 MHz, DMSO-d$_6$, δ ppm) 196.6, 177.0, 154.0, 149.7, 144.2, 135.9, 135.2, 131.8, 131.5, 129.6, 128.8, 124.7, 124.2, 123.9, 123.6, 122.2, 121.2, 118.1, 114.5, 113.3, 108.9, 73.1, 46.7, 39.7, 28.3, 22.3. FTIR (neat, cm$^{-1}$) 3355, 2953, 1740, 1612, 1468, 1354, 1097, 1068, 860, 753. HRMS (ESI, m/z) calculated for $C_{26}H_{23}N_3O_3C$ [M+H]$^+$: 460.1428. found 460.1420 and for $C_{26}H_{22}N_3O_3ClNa$ [M+Na]$^+$: 482.1247. found 482.1238. Flash chromatography conditions: 25 g column, flow rate 18 mL/min, 100/0 to 50/50 cyclohexane/EtOAc. R$_f$=0.05, 50/50 cyclohexane/EtOAc.

1-(5-Chloro-3-propyl(1H)indol-3-yl)-3-hydroxy-3-(2-oxo-2-(3-methylphenyl)ethyl)indol-2-one (APV-ST423)

The compound APV-ST423 was prepared by following the general procedure D, using 1-(5-chloro-3-propyl(1H) indol-3-yl)indole-2,3-dione (80 mg, 0.24 mmol) and 3'-methylacetophenone (45 μL, 0.33 mmol). The compound indicated in the title was obtained after flash chromatography followed by trituration in pentane, in the form of a beige-colored solid (95 mg). Yield=85%. m.p.=125.9-127.8° C. $^1$H NMR (300 MHz, DMSO-d$_6$, δ ppm) 11.00 (s, 1H), 7.68 (br, s, 2H), 7.60 (br, s, 1H), 7.45-7.31 (m, 4H), 7.28 (br, s, 1H), 7.22 (d, J=7.7 Hz, 1H), 7.06 (dd, J=8.5, 1.6 Hz, 1H), 7.02-6.88 (m, 2H), 6.13 (s, 1H), 4.13 (d, J=17.6 Hz, 1H), 3.91-3.59 (m, 2H), 3.66 (d, J=17.5 Hz, 1H), 2.90-2.73 (m, 2H), 2.32 (s. 3H), 2.08-1.92 (m, 2H). $^{13}$C NMR (75 MHz, DMSO-d$_6$, δ ppm) 197.0, 177.1, 144.3, 138.5, 136.6, 135.2, 134.5, 131.7, 129.5, 129.0, 128.8, 128.8, 125.6, 124.7, 123.7, 123.3, 122.1, 121.2, 118.1, 114.6, 113.3, 108.8, 73.1, 46.6, 39.6, 28.3, 22.3, 21.2F. FTIR (neat, cm$^{-1}$) 3375, 2941, 1680, 1614, 1467, 1250, 1162, 1067, 799, 752. HRMS (ESI, m/z) calculated for $C_{28}H_{25}N_2O_3ClNa$ [M+Na]$^+$: 495.1451. found 495.1463. Flash chromatography conditions: 25 g column, flow rate 18 mL/min, 100/0 to 50/50 cyclohexane/EtOAc. R$_f$=0.45, 50/50 cyclohexane/EtOAc.

1-(5-Chloro-3-propyl(1H)indol-3-yl)-3-hydroxy-3-(2-oxo-2-(3-fluorophenyl)ethyl)indol-2-one (APV-ST424)

The compound APV-ST424 was prepared by following the general procedure D, using 1-(5-chloro-3-propyl(1H) indol-3-yl)indole-2,3-dione (80 mg, 0.24 mmol) and 3'-fluoroacetophenone (41 μL, 0.33 mmol). The compound indicated in the title was obtained after flash chromatography followed by trituration in pentane, in the form of a beige-colored solid (70 mg). Yield=62%. m.p.=173.7-175.6° C. $^1$H NMR (300 MHz, DMSO-$d_6$, δ ppm) 7.76 (d, J=7.5 Hz, 1H), 7.64 (d, J=9.7 Hz, 1H), 7.59 (s, J=5.6 Hz, 1H), 7.57-7.43 (m, 2H), 7.37 (s, 1H), 7.35 (s, 1H), 7.27 (s, 1H), 7.23 (d, J=7.7 Hz, 1H), 7.06 (dd, J=8.6, 1.7 Hz, 1H), 7.02-6.90 (m, 2H), 6.17 (s, 1H), 4.16 (d, J=17.7 Hz, 1H), 3.87-3.66 (m, 3H), 3.68 (d, J=17.8 Hz, 1H), 2.89-2.71 (m, 2H), 2.09-1.92 (m, 2H). $^{13}$C NMR (75 MHz, DMSO-$d_6$, δ ppm) 195.57, 176.54, 162.10 (d, $J_{C-F}$=245.5 Hz), 143.79, 138.22 (d, $J_{C-F}$=6.1 Hz), 134.70, 131.05, 130.89 (d, $J_{C-F}$=7.7 Hz), 129.09, 128.29, 124.23, 124.23, 123.39, 122.87, 121.69, 120.77, 120.36 (d, $J_{C-F}$=21.4 Hz), 117.60, 114.40 (d, $J_{C-F}$=22.4 Hz), 114.09, 112.86, 108.41, 72.59, 46.17, 39.24, 27.86, 21.86. $^{19}$F NMR (188 MHz, DMSO-$d_6$, δ ppm) −112.5, FTIR (neat, cm$^{-1}$) 3324, 2926, 1688, 1612, 1467, 1442, 1340, 1249, 1164, 892, 792, 753. HRMS (ESI, m/z) calculated for $C_{27}H_{22}N_2O_3FClNa$ [M+Na]$^+$: 499.1201. found 499.1201. Flash chromatography conditions: 25 g column, flow rate 18 mL/min, 100/0 to 50/50 cyclohexane/EtOAc. $R_f$=0.40, 50/50 cyclohexane/EtOAc.

1-(5-Chloro-3-propyl(1H)indol-3-yl)-3-hydroxy-3-(2-oxo-2-(4-fluorophenyl)ethyl)indol-2-one (APV-ST421)

The compound APV-ST421 was prepared by following the general procedure D, using 1-(5-chloro-3-propyl(1H)indol-3-yl)indole-2,3-dione (80 mg, 0.24 mmol) and 4'-fluoroacetophenone (40 μL, 0.33 mmol). The compound indicated in the title was obtained after flash chromatography followed by trituration in pentane, in the form of a beige-colored solid (90 mg). Yield=80%. m.p.=111.1-112.9° C. $^1$H NMR (300 MHz, DMSO-$d_6$, δ ppm) 11.00 (s, 1H), 7.99 (d, J=5.7 Hz, 1H), 7.96 (d, J=5.6 Hz, 1H), 7.59 (s, 1H), 7.38-7.30 (m, 3H), 7.30-7.19 (m, 3H), 7.06 (dd, J=8.6, 1.7 Hz, 1H), 7.02-6.90 (m, 2H), 6.15 (s, 1H), 4.14 (d, J=17.7 Hz, 1H), 3.87-3.65 (m, 2H), 3.66 (d, J=17.5 Hz, 1H), 2.87-2.74 (m, 2H), 2.08-1.92 (m, 2H). $^{13}$C NMR (75 MHz, DMSO-$d_6$, δ ppm) 195.10, 176.59, 165.11 (d, $J_{C-F}$=252.1 Hz), 143.80, 134.70, 132.81, 131.14, 130.98 (d, $J_{C-F}$=9.4 Hz, 2*CH), 129.04, 128.29, 124.23, 123.34, 122.86, 121.64, 120.76, 117.59, 115.66 (d, $J_{C-F}$=21.9 Hz, 2*CH), 114.09, 112.85, 108.38, 72.61, 45.96, 39.17, 27.82, 21.82. $^{19}$F NMR (188 MHz, DMSO-$d_6$, δ ppm) −103.8. FTIR (neat, cm$^{-1}$) 3338, 3926, 1628, 1614, 1596, 1467, 1345, 1227, 1157, 1066, 794, 753. HRMS (ESI, m/z) calculated for $C_{27}H_{22}N_2O_3FClNa$ [M+Na]$^+$: 499.1201. found 499.1201. Flash chromatography conditions: 25 g column, flow rate 18 mL/min, 100/0 to 50/50 cyclohexane/EtOAc. $R_f$=0.40, 50/50 cyclohexane/EtOAc.

1-(5-Chloro-3-propyl(1H)indol-3-yl)-3-hydroxy-3-(2-oxo-2-((3-trifluoromethyl)phenyl)ethyl)indol-2-one (APV-ST425)

The compound APV-ST425 was prepared by following the general procedure D, using 1-(5-chloro-3-propyl(1H)indol-3-yl)indole-2,3-dione (80 mg, 0.24 mmol) and 3'-(trifluoromethyl)acetophenone (50 μL, 0.33 mmol). The compound indicated in the title was obtained after flash chromatography followed by trituration in pentane, in the form of a beige-colored solid (90 mg). Yield=72%. m.p.=143.1-144.9° C., $^1$H NMR (300 MHz, DMSO-$d_6$, δ ppm) 11.00 (s, 1H), 8.19 (d, J=7.3 Hz, 1H), 8.11 (s, 1H), 7.98 (d, J=7.4 Hz, 1H), 7.77-7.67 (m, 1H), 7.57 (s, 1H), 7.42-7.31 (m, 2H), 7.31-7.19 (m, 2H), 7.10-6.89 (m, 3H), 6.19 (s, 1H), 4.23 (d, J=17.6 Hz, 1H), 3.86-3.67 (m, 2H), 3.74 (d, J=17.5 Hz, 1H), 2.90-2.72 (m, 2H), 2.12-1.88 (m, 2H). $^{13}$C NMR (75 MHz, DMSO-$d_6$, δ ppm) 195.7, 176.5, 143.7, 136.7, 134.7, 132.0, 131.0, 130.1, 129.8-129.6 (m, CH fluorine coupled), 129.1, 128.3, 124.5-124.2 (m, CH fluorine coupled), 124.2, 123.5, 122.9, 121.7, 120.8, 117.6, 114.0, 112.9, 108.4, 72.7, 46.2, 39.2, 27.8, 21.8. NB: The quaternary carbons alpha and beta to the fluorines are not visible (—C—CF3). $^{19}$F NMR (188 MHz, DMSO-$d_6$, δ ppm) −61.7. FTIR (neat, cm$^{-1}$) 3309, 2941, 1689, 1613, 1468, 1324, 1201, 1164, 1124, 1070, 793, 753, 693. HRMS (ESI, m/z) calculated for $C_{28}H_{22}N_2O_3F_3ClNa$ [M+Na]$^+$: 549.1169. found 549.1180. Flash chromatography conditions: 25 g column, flow rate 18 mL/min, 100/0 to 50/50 cyclohexane/EtOAc. $R_f$=0.40, 50/50 cyclohexane/EtOAc.

1-(5-Chloro-3-ethyl(1H)indol-3-yl)-3-hydroxy-3-(2-oxo-2-phenylethyl)indol-2-one (APV-ST409)

The compound APV-ST409 was prepared by following the general procedure D, using 1-(5-chloro-3-ethyl(1H)indol-3-yl)indole-2,3-dione (80 mg, 0.25 mmol) and acetophenone (57 μL, 0.49 mmol). The compound indicated in the title was obtained after flash chromatography followed by trituration in pentane, in the form of a white solid (18 mg). Yield=20%. m.p.=170.7-172.4° C. $^1$H NMR (300 MHz, DMSO-$d_6$, δ ppm) 11.09 (s, 1H), 7.89 (d, J=7.9 Hz, 2H), 7.67-7.59 (m, 2H), 7.51 (d, J=7.5 Hz, 1H), 7.48 (d, J=7.7 Hz, 1H), 7.41-7.34 (m, 3H), 7.27-7.20 (m, 1H), 7.09 (dd, J=8.5, 1.3 Hz, 1H), 7.01-6.89 (m, 2H), 6.17 (s, 1H), 4.13 (d, J=17.5 Hz, 1H), 3.99-3.85 (m, 2H), 3.65 (d, J=17.4 Hz, 1H), 3.04 (t, J=7.7 Hz, 2H). $^{13}$C NMR (75 MHz, DMSO-$d_6$, δ ppm) 196.9, 177.0, 144.0, 136.6, 135.2, 133.9, 131.5, 129.5, 129.2, 129.2, 128.7, 128.4, 128.4, 125.6, 123.9, 123.6, 122.1, 121.4, 117.9, 113.4, 111.4, 108.8, 73.2, 46.5, 40.4, 23.2. FTIR (neat, cm$^{-1}$) 3357, 2919, 1713, 1683, 1614, 1467, 1346, 1217, 1162, 1096, 1022, 752. HRMS (ESI, m/z) calculated for $C_{26}H_{22}N_2O_3Cl$ [M+H]$^+$: 445.1319. found 445.1324 and for $C_{26}H_{21}N_2O_3ClNa$ [M+Na]$^+$: 467.1138. found 467.1136. Flash chromatography conditions: 25 g column, flow rate 18 mL/min, 100/0 to 50/50 cyclohexane/EtOAc. $R_f$=0.35, 50/50 cyclohexane/EtOAc.

1-(5-Chloro-3-ethyl(1H)indol-3-yl)-3-hydroxy-3-(2-oxo-2-(2-chlorophenyl)ethyl)indol-2-one (APV-ST410)

The compound APV-ST410 was prepared by following the general procedure D, using 1-(5-chloro-3-ethyl(1H)indol-3-yl)indole-2,3-dione (80 mg, 0.25 mmol) and 2'-chloroacetophenone (45 μL, 0.39 mmol). The compound indicated in the title was obtained after flash chromatography followed by trituration in pentane, in the form of a white solid (30 mg). Yield=25%. m.p.=120.1-122.0° C. $^1$H NMR (300 MHz, DMSO-$d_6$, ppm) 11.10 (s, 1H), 7.64 (d, J=1.4 Hz, 1H), 7.52-7.44 (m 3H), 7.44-7.34 (m, 4H), 7.30-7.23 (m, 1H), 7.09 (dd, J=8.6, 1.5 Hz, 1H), 7.01-6.93 (m, 2H), 6.24 (s, 1H), 3.92 (d, J=16.4 Hz, 1H), 4.01-3.77 (m, 2H), 3.60 (d, J=16.8 Hz, 1H), 3.01 (t, J=7.6 Hz, 2H). $^{13}$C NMR (75 MHz, DMSO-$d_6$, δ ppm) 199.0, 176.6, 143.8, 138.4, 135.1, 132.9, 130.9, 130.9, 130.1, 129.7, 129.7, 128.7, 127.8, 125.6, 124.3, 123.6, 122.3, 121.4, 117.9, 113.5, 111.3, 109.0, 73.2, 50.3, 40.4, 23.0. FTIR (neat, cm$^{-1}$) 3333, 2917, 2850, 1701, 1613, 1468, 1163, 1096, 1061, 753. HRMS (ESI, m/z) calculated for $C_{26}H_{21}N_2O_3Cl_2$ [M+H]$^+$: 479.0929. found 479.0929 and for $C_{26}H_{20}N_2O_3Cl_2Na$ [M+Na]$^+$: 501.0749. found 501.0746. Flash chromatography conditions: 25 g column, flow rate 18 mL/min, 100/0 to 50/50 cyclohexane/EtOAc. $R_f$=0.41, 50/50 cyclohexane/EtOAc.

1-(5-Chloro-3-ethyl(1H)indol-3-yl)-3-hydroxy-3-(2-oxo-2-(3-chlorophenyl)ethyl)indol-2-one (APV-ST411)

The compound APV-ST411 was prepared by following the general procedure D, using 1-(5-chloro-3-ethyl(1H)indol-3-yl)indole-2,3-dione (80 mg, 0.25 mmol) and 3'-chloroacetophenone (45 µL, 0.39 mmol). The compound indicated in the title was obtained after flash chromatography followed by trituration in pentane, in the form of a white solid (25 mg). Yield=21%. m.p.=120.9-122.8° C. $^1$H NMR (300 MHz, CDCl$_3$, δ ppm) 11.10 (s, 1H), 7.91-7.82 (m, 2H), 7.73-7.63 (m, 2H), 7.56-7.48 (m, 1H), 7.42-7.33 (m, 3H), 7.29-7.20 (m, 1H), 7.09 (dd, J=8.5, 1.2 Hz, 1H), 7.02-6.91 (m, 2H), 6.20 (s, 1H), 4.14 (d, J=17.5 Hz, 1H), 4.03-3.79 (m, 2H), 3.64 (d, J=17.5 Hz, 1H), 3.03 (t, J=7.7 Hz, 2H). $^{13}$C NMR (75 MHz, CDCl$_3$, δ ppm) 195.5, 176.4, 143.5, 137.9, 134.7, 133.7, 133.1, 130.9, 130.7, 129.1, 128.2, 127.7, 126.7, 125.2, 123.6, 123.1, 121.7, 120.9, 117.4, 113.0, 110.9, 108.4, 72.7, 46.2, 40.0, 22.6. FTIR (neat, cm$^{-1}$) 3338, 2918, 2850, 1687, 1614, 1468, 1344, 1209, 1164, 1097, 1058, 782, 680. HRMS (ESI, m/z) calculated for $C_{26}H_{21}N_{23}C_{12}$ [M+H]$^+$: 479.0929. found 479.0934 and for $C_{26}H_2N_2O_3Cl_2Na$ [M+Na]$^+$: 501.0759. found 501.0753. Flash chromatography conditions: 25 g column, flow rate 18 mL/min, 100/0 to 50/50 cyclohexane/EtOAc. $R_f$=0.34, 50/50 cyclohexane/EtOAc.

4-(2-(1-(2-(1H-Indol-3-yl)ethyl)-3-hydroxy-2-oxoindolin-3-yl)acetyl)benzonitrile (APV-GG091)

The compound APV-GG091 was prepared by following the general procedure D, using 1-(5-chloro-3-ethyl(1H)indol-3-yl)indole-2,3-dione (145 mg, 0.5 mmol) and 4-acetylbenzonitrile (80 mg, 0.55 mmol). The compound indicated in the title was obtained after flash chromatography on a column of silica gel (80/20 to 50/50 cyclohexane/EtOAc), in the form of a white solid (90 mg). Yield=41%.

$^1$H NMR (300 MHz, CDCl$_3$, δ ppm) 8.10 (s, 1H), 7.87 (d, J=8.3 Hz, 2H), 7.71 (d, J=8.3 Hz, 2H), 7.46 (d, J=7.9 Hz, 1H), 7.35 (d, J=7.7 Hz, 2H), 7.30 (d, J=7.9 Hz, 1H), 7.17 (t, J=7.7 Hz, 1H), 7.11 (d, J=2.2 Hz, 1H), 7.04 (td, J=7.7, 3.0 Hz, 2H), 6.89 (d, J=7.9 Hz, 1H), 4.14-3.94 (m, 2H), 3.64 (d, J=17.3 Hz, 1H), 3.64 (s, 1H), 3.32 (d, J=17.3 Hz, 1H), 3.2 (t, J=7.2 Hz, 2H). $^{13}$C NMR (75 MHz, DMSO-d$_6$, b ppm) 196.0, 176.3, 143.4, 139.2, 138.2, 136.2, 132.7, 130.8, 129.2, 128.8, 128.6, 127.1, 124.4, 123.6, 123.3, 123.2, 121.8, 121.0, 118.4, 118.1, 115.3, 111.5, 110.8, 108.4, 72.7, 46.5, 22.7. HRMS (ESI, m/z) calculated for $C_{27}H_{21}N_3O_3Na$ [M+Na]$^+$ 458.1481. found 458.1485.

1-(2-(1H-Indol-3-yl)ethyl)-3-hydroxy-3-(2-oxopropyl)indolin-2-one (APV-GG057)

The compound APV-GG057 was prepared by following the general procedure D, using 1-(2-(1H-indol-3-yl)ethyl)indoline-2,3-dione (145 mg, 0.5 mmol) and acetone (40 µL, 0.54 mmol). The compound indicated in the title was obtained after chromatography on preparative plates (2×2 mm; 50/50 cyclohexane/EtOAc), in the form of a beige-colored solid (79 mg). Yield=45%.

$^1$H NMR (300 MHz, CDCl$_3$, δ ppm) 8.08 (s, 1H), 7.47 (d, J=7.9 Hz, 1H), 7.35 (d, J=7.0 Hz, 2H), 7.30 (d, J=7.9 Hz, 1H), 7.17 (t, J=7.7 Hz, 1H), 7.09 (d, J=2.2 Hz, 1H), 7.05 (td, J=7.5, 3.8 Hz, 2H), 6.83 (d, J=7.9 Hz, 1H), 4.14 (br s, 1H), 4.13-3.88 (m, 2H), 3.24-3.11 (m, 2H), 2.92 (d, J=16.9 Hz, 1H), 2.69 (d, J=16.9 Hz, 1H), 2.07 (s, 3H). $^{13}$C NMR (75 MHz, CDCl$_3$, δ ppm) 208.1, 176.0, 143.1, 137.8, 130.1, 128.6, 124.2, 123.4, 123.1, 122.7, 122.3, 119.6, 118.6, 112.5, 111.5, 109.0, 74.3, 48.4, 41.2, 31.6, 23.0. HRMS (ESI, m/z) calculated for $C_{21}H_2N_2O_3Na$ [M+Na]$^+$: 371.1372. found 371.1360.

1-(2-(1H-Indol-3-yl)ethyl)-3-hydroxy-3-(3-oxobutan-2-yl)indolin-2-one (APV-GG059)

The compound APV-GG058 was prepared by following the general procedure D, using 1-(2-(1H-indol-3-yl)ethyl)indoline-2,3-dione (145 mg, 0.5 mmol) and butan-2-one (50 µL, 0.56 mmol). The compound indicated in the title was obtained after chromatography on preparative plates (2×2 mm; 50/50 cyclohexane/EtOAc, double elution), in the form of an orange-colored solid (30 mg). Yield=17%.

$^1$H NMR (300 MHz, CDCl$_3$, δ ppm) 8.14 (s, 1H), 7.49 (d, J=7.9 Hz, 1H), 7.41-7.25 (m, 3H), 7.35 (d, J=7.9 Hz, 1H), 7.11-7.03 (m, 3H), 6.85 (d, J=7.9 Hz, 1H), 4.14 (br s, 1H), 4.15-4.02 (m, 1H), 3.99-3.87 (m, 1H), 3.16 (td, 7.2, 3.6 Hz, 2H), 2.93 (q, J=7.2 Hz, 1H), 2.16 (s, 3H), 0.97 (d, J=7.2 Hz, 3H). $^{13}$C NMR (75 MHz, CDCl$_3$, δ ppm) 212.8, 176.6, 143.3, 136.4, 130.1, 128.2, 127.6, 125.9, 123.0, 122.6, 122.3, 119.6, 118.6, 112.4, 111.6, 108.9, 50.2, 41.1, 31.5, 29.0, 23.2, 11.6. HRMS (ESI, m/z) calculated for $C_{22}H_{22}N_2O_3Na$ [M+Na]$^+$: 385.1528. found 385.1525.

1-(2-(1H-Indol-3-yl)ethyl)-3-hydroxy-3-(2-oxobutyl)indolin-2-one (APV-GG062)

The compound APV-GG062 was prepared by following the general procedure D, using 1-(2-(1H-indol-3-yl)ethyl)indoline-2,3-dione (145 mg, 0.5 mmol) and butan-2-one (50 µL, 0.56 mmol). The compound indicated in the title was obtained after chromatography on preparative plates (2×2 mm; 50/50 cyclohexane/EtOAc, double elution), in the form of a pale yellow solid (47 mg). Yield=26%.

$^1$H NMR (300 MHz, CDCl$_3$, δ ppm) 8.06 (s, 1H), 7.48 (d, J=7.7 Hz, 1H), 7.38-27 (m, 3H), 7.17 (t, J=7.4 Hz, 1H), 7.11-7.00 (m, 3H), 6.83 (d, J=7.7 Hz, 1H), 4.28 (s, 1H), 4.12-3.88 (m, 2H), 3.22-3.11 (m, 2H), 2.88 (d, J=16.7 Hz, 1H), 2.66 (d, J=16.7 Hz, 1H), 2.32 (q, J=7.2 Hz, 2H) 0.99 (t, J=7.2 Hz, 3H). $^{13}$C NMR (75 MHz, CDCl$_3$, δ ppm) 210.8, 176.2, 143.1, 136.3, 130.1, 127.7, 124.1, 123.1, 122.8, 122.2, 119.5, 118.6, 112.4, 109.1, 74.5, 51.6, 47.3, 41.1, 37.6, 23.1, 11.6, 7.5. HRMS (ESI, m/z) calculated for $C_{22}H_{22}N_2O_3Na$ [M+Na]$^+$: 385.1528. found 385.1522.

1-(2-(1H-Indol-3-yl)ethyl)-3-hydroxy-3-(2-oxohexyl)indolin-2-one (APV-GG093)

The compound APV-GG093 was prepared by following the general procedure D, using 1-(2-(1H-indol-3-yl)ethyl)indoline-2,3-dione (145 mg, 0.5 mmol) and hexan-2-one (70 µL, 0.57 mmol). The compound indicated in the title was obtained after chromatography on preparative plates (2×2 mm; 50/50 cyclohexane/EtOAc), in the form of a beige-colored solid (64 mg). Yield=33%.

$^1$H NMR (300 MHz, CDCl$_3$, δ ppm) 8.16 (s, 1H), 7.46 (d, J=7.8 Hz, 1H), 7.37-7.27 (m, 2H), 7.30 (d, J=7.9 Hz, 1H), 7.17 (t, J=7.4 Hz, 1H), 7.09-7.00 (m, 3H), 6.83 (d, J=7.8 Hz, 1H), 4.34 (br s, 1H), 4.11-3.88 (m, 2H), 3.22-3.11 (m, 2H), 2.90 (d, J=16.8 Hz, 1H), 2.66 (d, J=16.8 Hz, 1H), 2.28 (t, J=7.3 Hz, 2H), 1.53-1.40 (m, 2H), 1.32-1.18 (m, 2H), 0.86

(t, J=7.2 Hz, 3H). ¹³C NMR (75 MHz, CDCl₃, δ ppm) 210.6, 176.3, 143.1, 136.3, 130.1, 127.7, 124.1, 123.1, 122.8, 122.2, 119.5, 118.6, 112.4, 111.6, 109.0, 74.5, 47.5, 44.1, 41.2, 25.5, 23.1 (2C), 22.3, 14.0. HRMS (ESI, m/z) calculated for $C_{24}H_{26}N_2O_3Na$ [M+Na]⁺: 413.1841. found 413.1840.

1-(2-(1H-Indol-3-yl)ethyl)-3-hydroxy-3-(3-methyl-2-oxobutyl)indolin-2-one (APV-GG090)

The compound APV-GG090 was prepared by following the general procedure D, using 1-(2-(1H-indol-3-yl)ethyl)indoline-2,3-dione (145 mg, 0.5 mmol) and 3-methylbutan-2-one (60 µL, 0.56 mmol). The compound indicated in the title was obtained after flash chromatography on a column of silica gel (70/30 to 60/40 cyclohexane/EtOAc), in the form of a beige-colored solid (100 mg). Yield=53%.

¹H NMR (300 MHz, CDCl₃, δ ppm) 8.05 (s, 1H), 7.5 (d, J=7.9 Hz, 1H), 7.35 (d, J=8.2 Hz, 1H), 7.31 (d, J=4.8 Hz, 1H), 7.29 (d, J=4.8 Hz, 1H), 7.18 (t, J=7.4 Hz, 1H), 7.12-7.00 (m, 3H), 6.83 (d, J=7.7 Hz, 1H), 4.38 (s, 1H), 4.17-3.90 (m, 2H), 3.17 (t, J=7.2 Hz, 2H), 3.00 (d, J=17 Hz, 1H), 2.71 (d, J=17 Hz, 1H), 2.50-2.38 (m, 1H), 1.02 (dd, J=6.9, 1.8 Hz, 6H). ¹³C NMR (75 MHz, CDCl₃, δ ppm) 214.2, 176.2, 143.1, 136.4, 130.1, 127.7, 124.1, 123.0, 122.7, 122.2, 119.6, 118.6, 112.5, 111.5, 109.0, 74.5, 45.5, 42.1, 41.1, 23.1, 17.9, 17.5. HRMS (ESI, m/z) calculated for $C_{23}H_{24}N_2O_3Na$ [M+Na]⁺: 399.1685. found 399.1687.

1-(2-(1H-Indol-3-yl)ethyl)-3-hydroxy-3-(2-oxobutyl)indolin-2-one (APV-GG061)

The compound APV-GG061 was prepared by following the general procedure D, using 1-(2-(1H-indol-3-yl)ethyl)indoline-2,3-dione (145 mg, 0.5 mmol) and 4-methylpentan-2-one (70 µL, 0.56 mmol). The compound indicated in the title was obtained after chromatography on preparative plates (2×2 mm; 50/50 cyclohexane/EtOAc, double elution), in the form of a yellow solid (60 mg). Yield=32%.

¹H NMR (300 MHz, CDCl₃, δ ppm) 8.06 (s, 1H), 7.48 (d, J=7.9 Hz, 1H), 7.37-7.27 (m, 3H), 7.17 (t, J=7.3 Hz, 1H), 7.12-6.99 (m, 3H), 6.83 (d, J=7.7 Hz, 1H), 4.28 (s, 1H), 4.12-3.88 (m, 2H), 3.17 (t, J=7.2 Hz, 2H), 2.9 (d, J=17 Hz, 1H), 2.65 (d, J=17 Hz, 1H), 2.20-2.15 (m, 2H), 2.11-2.00 (m, 1H), 0.86 (d, J=6.5 Hz, 6H). ¹³C NMR (75 MHz, CDCl₃, δ ppm) 210.1, 176.3, 143.1, 136.3, 130.1, 127.7, 124.1, 123.1, 122.8, 122.2, 119.5, 118.6, 112.4, 111.6, 109.0, 74.4, 70.7, 53.2, 48.1, 41.1, 24.5, 23.0, 22.6 (2C). HRMS (ESI, m/z) calculated for $C_{24}H_{26}N_2O_3Na$ [M+Na]⁺ 413.1841. found 413.1851.

1-(2-(1H-Indol-3-yl)ethyl)-3-(2-cyclopropyl-2-oxoethyl)-3-hydroxyindolin-2-one (APV-GG072)

The compound APV-GG072 was prepared by following the general procedure D, using 1-(2-(1H-indol-3-yl)ethyl)indoline-2,3-dione (145 mg, 0.5 mmol) and 1-cyclopropylethan-1-one (55 µL, 0.56 mmol). The compound indicated in the title was obtained after flash chromatography on a column of silica gel (70/30 to 50/50 cyclohexane/EtOAc), in the form of a beige-colored solid (117 mg). Yield=62%.

¹H NMR (300 MHz, CDCl₃, δ ppm) 8.15 (s, 1H), 7.5 (d, J=7.8 Hz, 1H), 7.33 (d, J=7.6 Hz, 1H), 7.29 (d, J=8.2 Hz, 1H), 7.27 (d, J=7.6 Hz, 1H), 7.17 (t, J=7.4 Hz, 1H), 7.10-6.99 (m, 3H), 6.83 (d, J=7.8 Hz, 1H), 4.04 (s, 1H), 4.07-3.90 (m, 2H), 3.16 (t, J=7.2 Hz, 2H), 3.11 (d, J=16.8 Hz, 1H), 2.83 (d, J=16.8 Hz, 1H), 1.84-1.74 (m, 1H), 1.08-0.98 (m, 2H), 0.92-0.83 (m, 2H). ¹³C NMR (75 MHz, CDCl₃, δ ppm) 210.0, 176.1, 143.0, 136.4, 130.0, 127.7, 124.3, 123.1, 122.7, 122.2, 119.6, 118.6, 112.4, 111.5, 109.0, 74.5, 60.6, 48.3, 41.1, 23.1, 22.1, 11.9, 11.8. HRMS (ESI, m/z) calculated for $C_{23}H_{22}N_2O_3Na$ [M+Na]⁺: 397.1528. found 397.1518.

1-(2-(1H-Indol-3-yl)ethyl)-3-(2-cyclopentyl-2-oxoethyl)-3-hydroxyindolin-2-one (APV-GG089)

The compound APV-GG089 was prepared by following the general procedure D, using 1-(2-(1H-indol-3-yl)ethyl)indoline-2,3-dione (145 mg, 0.5 mmol) and 1-cyclopentylethan-1-one (70 µL, 0.57 mmol). The compound indicated in the title was obtained after flash chromatography on a column of silica gel (70/30 to 60/40 cyclohexane/EtOAc), in the form of a yellow solid (130 mg). Yield=65%.

¹H NMR (300 MHz, CDCl₃, δ ppm) 8.04 (s, 1H), 7.51 (d, J=7.8 Hz, 1H), 7.35 (d, J=8.2 Hz, 1H), 7.32 (d, J=7.8 Hz, 1H), 7.29 (d, J=8.2 Hz, 1H), 7.18 (t, J=7.6 Hz, 1H), 7.11-7.00 (m, 3H), 6.82 (d, J=7.9 Hz, 1H), 4.41 (s, 1H), 4.11-3.90 (m, 2H), 3.17 (t, J=7.4 Hz, 2H), 3.01 (d, J=17.0 Hz, 1H), 2.74 (d, J=17.0 Hz, 1H), 2.76-2.66 (m, 1H), 1.79-1.58 (m, 8H). ¹³C NMR (75 MHz, CDCl₃, δ ppm) 212.6, 176.2, 143.1, 136.4, 130.3, 130.0, 127.7, 124.1, 123.0, 122.7, 122.2, 119.6, 118.6, 112.5, 111.5, 109.0, 74.5, 52.6, 46.8, 41.1, 28.6, 28.5, 27.1, 26.1, 23.1. HRMS (ESI, m/z) calculated for $C_{25}H_{26}N_2O_3Na$ [M+Na]⁺: 425.1841. found 425.1845.

1-(2-(1H-Indol-3-yl)ethyl)-3-(2-cyclohexyl-2-oxoethyl)-3-hydroxyindolin-2-one (APV-GG076)

The compound APV-GG089 was prepared by following the general procedure D, using 1-(2-(1H-indol-3-yl)ethyl)indoline-2,3-dione (145 mg, 0.5 mmol) and 1-cyclohexylethan-1-one (80 µL, 0.58 mmol). The compound indicated in the title was obtained after flash chromatography on a column of silica gel (70/30 to 60/40 cyclohexane/EtOAc), in the form of a yellow solid (89 mg). Yield=43%.

¹H NMR (300 MHz, CDCl₃, δ ppm) 8.05 (s, 1H), 7.49 (d, J=7.8 Hz, 1H), 7.35 (d, J=8.2 Hz, 1H), 7.32 (d, J=7.8 Hz, 1H), 7.3 (d, J=7.7 Hz, 1H), 7.18 (t, J=7.4 Hz, 1H), 7.12-6.99 (m, 3H), 6.83 (d, J=7.8 Hz, 1H), 4.49 (s, 1H), 4.13-3.88 (m, 2H), 3.17 (t, J=7.4 Hz, 2H), 2.97 (d, J=17.0 Hz, 1H), 2.66 (d, J=17.0 Hz, 1H), 2.25-2.14 (m, 1H), 1.80-1.68 (m, 4H), 1.32-1.10 (m, 4H). ¹³C NMR (75 MHz, CDCl₃, δ ppm) 213.9, 176.2, 143.1, 136.3, 130.0, 127.7, 124.1, 123.0, 122.8, 122.2, 119.5, 118.6, 112.5, 111.5, 109.0, 74.6, 51.8, 45.6, 41.1, 28.1, 28.0, 25.9, 25.7, 25.6, 26.1, 23.1. HRMS (ESI, m/z) calculated for $C_{26}H_{28}N_2O_3Na$ [M+Na]⁺: 439.1998. found 439.2002.

1-(2-(1H-Indol-3-yl)ethyl)-3-hydroxy-3-((R)-2-oxocyclopentyl)indolin-2-one (APV-GG082)

The compound APV-GG089 was prepared by following the general procedure D, using 1-(2-(1H-indol-3-yl)ethyl)indoline-2,3-dione (145 mg, 0.5 mmol) and cyclopentanone (50 µL, 0.57 mmol). The compound indicated in the title was obtained after flash chromatography on a column of silica gel (70/30 cyclohexane/EtOAc), in the form of a beige-colored solid (35 mg). Yield=19%.

¹H NMR (300 MHz, CDCl₃, δ ppm) 8.01 (s, 1H), 7.65 (d, J=7.7 Hz, 1H), 7.38-7.27 (m, 3H), 7.23-7.03 (m, 4H), 6.80 (d, J=7.7 Hz, 1H), 5.63 (s, 1H), 4.13-4.01 (m, 1H), 3.98-3.86

(m, 1H), 3.20-3.10 (m, 2H), 2.72-2.62 (m, 1H), 2.35-2.25 (m, 1H), 1.86-1.73 (m, 1H), 1.72-1.59 (m, 4H).

$^{13}$C NMR (75 MHz, CDCl$_3$, δ ppm) 221.8, 176.4, 143.4, 136.4, 130.3, 128.8, 127.5, 124.2, 123.4, 122.6, 122.3, 119.7, 118.8, 112.2, 111.4, 108.9, 62.8, 51.8, 40.7, 39.8, 25.2, 23.4, 20.6.

HRMS (ESI, m/z) calculated for C$_{23}$H$_{23}$N$_2$O$_3$Na [M+Na]$^+$: 397.1528. found 397.1531.

1-(2-(1H-Indol-3-yl)ethyl)-3-(2-(furan-2-yl)-2-oxo-ethyl)-3-hydroxyindolin-2-one (APV-GG087)

The compound APV-GG089 was prepared by following the general procedure D, using 1-(2-(1H-indol-3-yl)ethyl)indoline-2,3-dione (145 mg, 0.5 mmol) and 1-(furan-2-yl)ethan-1-one (55 µL, 0.55 mmol). The compound indicated in the title was obtained after flash chromatography on a column of silica gel (70/30 to 60/40 cyclohexane/EtOAc), in the form of a pale orange solid (90 mg). Yield=45%.

$^1$H NMR (300 MHz, CDCl$_3$, δ ppm) 8.05 (s, 1H), 7.60-7.54 (m, 2H), 7.37 (t, J=7.2 Hz, 2H), 7.30-7.06 (m, 6H), 7.03 (t, J=7.5 Hz, 1H), 6.81 (d, J=7.7 Hz, 1H), 6.52 (dd, J=3.4, 1.5 Hz, 1H), 4.19 (s, 1H), 4.09-3.94 (m, 2H), 3.54 (d, J=16.8 Hz, 1H), 3.19 (d, J=16.8 Hz, 1H), 3.18 (t, J=16.8 Hz, 2H). $^{13}$C NMR (75 MHz, CDCl$_3$, δ ppm) 186.9, 176.2, 152.4, 147.3, 143.2, 136.4, 130.1, 129.9, 127.6, 124.4, 123.1, 122.7, 122.2, 119.6, 118.6, 118.4, 112.8, 112.4, 111.6, 109.0, 74.6, 44.1, 41.1, 23.2. HRMS (ESI, m/z) calculated for C$_{24}$H$_2$N$_{24}$Na [M+Na]$^+$: 423.1321. found 423.1318.

1-(2-(1H-Indol-3-yl)ethyl)-3-(2-(benzofuran-2-yl)-2-oxoethyl)-3-hydroxyindolin-2-one (APV-GG084)

The compound APV-GG084 was prepared by following the general procedure D, using 1-(2-(1H-indol-3-yl)ethyl)indoline-2,3-dione (145 mg, 0.5 mmol) and 1-(benzofuran-2-yl)ethan-1-one (88 mg, 0.55 mmol). The compound indicated in the title was obtained after flash chromatography on a column of silica gel (80/20 cyclohexane/EtOAc), in the form of a pale orange solid (90 mg). Yield=40%.

$^1$H NMR (300 MHz, CDCl$_3$, δ ppm) 8.03 (s, 1H), 7.69 (d, J=8.0 Hz, 1H), 7.58-7.23 (m, 8H) 7.19 (t, J=7.4 Hz, 1H), 7.13-7.06 (m, 2H), 7.01 (t, J=7.4 Hz, 1H), 6.83 (d, J=7.8 Hz, 1H), 4.12-3.92 (m, 2H), 4.04 (s, 1H), 3.69 (d, J=16.8 Hz, 1H), 3.31 (d, J=16.8 Hz, 1H), 3.2 (t, J=3.2 Hz, 2H), $^{13}$C NMR (75 MHz, CDCl$_3$, δ ppm) 188.8, 176.2, 156.0, 152.1, 143.2, 136.3, 130.2, 129.7, 129.0, 127.6, 127.1, 124.4, 124.3, 123.7, 123.1, 122.7, 122.2, 119.6, 118.6, 114.4, 112.7, 112.5, 111.6, 109.1, 74.6, 44.7, 41.2, 23.2. HRMS (ESI, m/z) calculated for C$_{28}$H$_{22}$N$_2$O$_4$Na [M+Na]$^+$: 473.1477. found 473.1482.

1-(2-(1H-Indol-3-yl)ethyl)-3-hydroxy-3-(2-oxo-2-(thiophen-2-yl)ethyl)indolin-2-one (APV-GG088)

The compound APV-GG088 was prepared by following the general procedure D, using 1-(2-(1H-indol-3-yl)ethyl)indoline-2,3-dione (145 mg, 0.5 mmol) and 1-(thiophen-2-yl)ethan-1-one (60 µL, 0.55 mmol). The compound indicated in the title was obtained after flash chromatography on a column of silica gel (70/30 to 50/50 cyclohexane/EtOAc), in the form of a pale orange solid (110 mg). Yield=53%.

$^1$H NMR (300 MHz, CDCl$_3$, δ ppm) 8.06 (s, 1H), 7.68 (d, J=5.0 Hz, 1H), 7.60-7.53 (m, 2H), 7.41 (d, J=7.6 Hz, 1H), 7.38 (d, J=8.2 Hz, 1H), 7.33-7.25 (m, 1H), 7.20 (t, J=7.5 Hz, 1H), 7.03 (t, J=7.5 Hz, 1H), 7.15-7.07 (m, 2H), 7.03 (t, J=7.5 Hz, 1H), 6.85 (d, J=7.9 Hz, 1H), 4.26 (s, 1H), 4.15-3.94 (m, 2H), 3.57 (d, J=16.5 Hz, 1H), 3.26 (d, J=16.5 Hz, 1H), 3.20 (t, J=7.4 Hz, 2H). $^{13}$C NMR (75 MHz, CDCl$_3$, b ppm) 191.1, 176.8, 152.3, 143.8, 143.2, 136.3, 135.1, 133.4, 130.1, 128.5, 124.5, 123.1, 122.7, 122.3, 119.6, 118.7, 118.2, 112.5, 111.5, 109.1, 74.6, 44.9, 41.2, 23.2. HRMS (ESI, m/z) calculated for C$_{24}$H$_{20}$N$_2$O$_3$SNa [M+Na]$^+$: 439.1092. found 439.1085.

1-(2-(1H-Idol-1-yl)ethyl)-3-(2-(2-chlorophenyl)-2-oxoethyl)-3-hydroxyindolin-2-one (APV-GG078)

The compound APV-GG078 was prepared by following the general procedure D, using 1-(2-(1H-indol-1-yl)ethyl)indoline-2,3-dione (220 mg, 0.76 mmol) and 1-(2-chlorophenyl)ethan-1-one (110 µL, 0.85 mmol). The compound indicated in the title was obtained after flash chromatography on a column of silica gel (70/30 cyclohexane/EtOAc), in the form of an orange-colored solid (130 mg). Yield=38%.

$^1$H NMR (300 MHz, CDCl$_3$, δ ppm) 7.52 (d, J=7.8 Hz, 1H), 7.42-7.27 (m, 5H), 7.23 (d, J=8.2 Hz, 1H), 7.19-7.06 (m, 3H), 7.0 (q, J=7.9 Hz, 2H), 6.39 (m, 2H), 4.54-4.40 (m, 2H), 4.22-4.11 (m, 1H), 4.06-3.94 (m, 1H), 3.85 (s, 1H), 3.56 (d, J=17.3 Hz, 1H), 3.35 (d, J=17.3 Hz, 1H). $^{13}$C NMR (75 MHz, CDCl$_3$, δ ppm) 201.3, 176.4, 142.7, 138.5, 136.1, 132.6, 131.4, 130.8, 130.3, 129.7, 129.0, 129.3, 128.3, 127.2, 124.3, 123.4, 121.8, 121.5, 119.8, 108.9, 108.4, 102.4, 74.4, 48.5, 43.7, 40.5. HRMS (ESI, m/z) calculated for C$_{26}$H$_{21}$N$_2$O$_3$NaCl [M+Na]$^+$: 467.1138. found 467.1142.

1-(4-(1H-Indol-1-yl)butyl)-3-(2-(2-chlorophenyl)-2-oxoethyl)-3-hydroxyindolin-2-one (APV-GG079)

The compound APV-GG079 was prepared by following the general procedure D, using 1-(4-(1H-indol-1-yl)butyl)indoline-2,3-dione (100 mg, 0.31 mmol) and 1-(2-chlorophenyl)ethan-1-one (45 µL, 0.35 mmol). The compound indicated in the title was obtained after flash chromatography on a column of silica gel (60/40 cyclohexane/EtOAc), in the form of an orange-colored solid (45 mg). Yield=31%.

$^1$H NMR (300 MHz, CDCl$_3$, δ ppm) 7.64 (d, J=7.7 Hz, 1H), 7.43-7.24 (m, 7H), 7.22-7.14 (m, 1H), 7.12-7.03 (m, 3H) 6.71 (d, J=7.9 Hz, 1H), 6.46 (d, J=3.0 Hz, 1H), 4.17 (t, J=6.8 Hz, 2H), 4.11 (s, 1H), 3.78 (d, J=16.8 Hz, 1H), 3.74-3.62 (m, 2H), 3.51 (d, J=16.8 Hz, 1H), 2.01-1.88 (m, 2H), 1.78-1.65 (m, 2H). $^{13}$C NMR (75 MHz, CDCl$_3$, δ ppm) 201.2, 176.5, 143.1, 138.6, 136.0, 132.7, 130.8, 130.3, 129.8, 127.9, 127.3, 124.4, 123.2, 121.7, 121.2, 120.3, 119.6, 119.5, 109.8, 109.6, 109.0, 101.4, 74.7, 49.0, 45.9, 39.7, 27.6, 24.8. HRMS (ESI, m/z) calculated for C$_{28}$H$_{25}$N$_2$O$_3$NaCl [M+Na]$^+$: 495.1451. found 495.1453.

Example 9: Biological Tests and Methods

Cell Cultures

Female Wistar rats in gestation with 17-day-old embryos (E17) were obtained from Janvier Labs. On the day of receipt of the animals, the rat is sacrificed and the embryos are dissected under sterile conditions to remove their brain, which is then micro-dissected in GBSS (Gey's balanced salt solution) medium to obtain the hippocampus from the two hemispheres, while discarding the meninges. The tissues harvested from at least five embryos are placed in 2 ml of DMEM medium (registered trademark) (Dulbecco's modified Eagle's medium—from Life Technologies) with 2% of fetal calf serum, 2 mM of glutamine, 0.1 mg/mL of penicillin-streptomycin antibiotic mixture (Life Technologies) and subjected to mechanical dissociation of the cells by passing through round-ended glass pipettes with an inside diameter decreasing from 0.5 to 0.2 mm. The cells are counted and 100 μl of suspension containing $25 \times 10^3$ cells are placed on a glass slide coated with polylysine (poly-D-lysine hydrobromide from 75 to 150 kDa, from Sigma) of Ø 12 mm, in 12-well culture plates and incubated for 2 hours at 37° C. under an atmosphere containing 5% of $CO_2$ to allow cell adhesion. A volume of 2 mL of culture medium is added gently: Neurobasal (registered trademark) with 1/50 (v:v) serum-free supplement B-27® (Life Technologies), 2 mM of glutamine, 0.1 mg/ml of penicillin-streptomycin antibiotic mixture (from Life Technologies), and incubation is again performed under the same conditions. Half of the medium is replaced twice a week for maintenance. The neuronal cells will be able to differentiate over a period of 12 to 30 days. The cultures are monitored by phase-contrast microscopy: the extension of the neurites and of the synaptic connections is observed for the neurons, which represent the majority of the cells, while a few astrocytes are also present.

Electrophysiology

Patch-Clamp System

The electrophysiology post consists of an Olympus IMT-2 model inverted phase-contrast microscope placed on a TMC antivibration table in a Faraday cage. The installation also comprises an SF-77B model Warner multichannel perfusion system, a Burleigh PCS-5000 model 3D-micromanipulator system holding the microelectrode probe, a Warner PC-505 model patch-clamp amplifier and a PowerLab 8/35 model 8-channel analog-digital interface from ADInstruments. The glass microelectrode is manufactured with thin-walled borosilicate capillary tubes (1.5 OD×1.17 ID×100 L mm, from Harvard Apparatus) and prepared with the Narishige PC10 model vertical electrode puller to obtain an electrical resistance of about 5 MOhm. The electrode of the pipette is filled with the intracellular medium composed of (in mM): 100 CsF, 40 CsCl, 1.2 $CaCl_2$, 20 HEPES, 10 EGTA, pH=7.4 (adjusted with CsOH).

The culture on its slide is placed in a 60 mm Petri dish with 2 ml of extracellular medium composed of (in mM): 140 NaCl, 5 KCl, 1.2 $CaCl_2$, 1.5 $MgCl_2$, 12 HEPES, 1$_2$ Na-HEPES, 33 glucose, pH=7.4.

The neuron selected is patched in the whole cell configuration. The maintenance potential is set at −60 mV.

Procedure for Applying the Test Compounds

The assembled glass microtubes of square cross section of the perfusion system each provide a stable stream of different composition. The "TTX" default medium corresponds to the extracellular medium to which is added 1 μM tetrodotoxin. The "NMDA" application medium is "TTX" supplemented with 100 μM of NMDA (N-methyl-D-aspartate) as agonist, and 5 μM of L-glycine as co-agonist. The "NMDA+ test compound" medium corresponds to the "NMDA" supplemented with 10 μM of the test compound. The "NMDA wash" is identical to the "NMDA" medium.

As a general rule, three applications of each test compound are performed on the patched cell, for 2 seconds at intervals of 3 minutes (to allow inversion of desensitization). The sequence of the applications is: 1) "NMDA", 2) "NMDA+ test compound", 3) "NMDA wash". The "TTX" medium is applied by default, before and after each application of test compound.

In the majority of the cells, a short run-up equilibration of the NMDA current takes place. Thus, the first NMDA application considered is the one after this equilibration, usually from 3 to 6 minutes. Certain cells showing a long-lasting run-down of the NMDA current after this short period which has preceded are thus eliminated.

UBP141 is obtained from ABcam, DQP 1105 from Tocris and tetrodotoxin (citrate-free) from Latoxan. All the other commercial chemical products are from Sigma-Aldrich.

Data Analysis

The electrophysiological data are collected digitally by the LabChart Pro 8 software and analyzed by means of the peak analysis module (ADInstruments). The peak parameters measured are the following:

| NMDA transmission property | Parameter | Unit | Physiological meaning |
|---|---|---|---|
| NMDA current | Height | pA | Maximum current |
| | Width 50 | ms | Duration of the current above 50% of Height |
| | Peak area | pA · s | Total current integrated over time |
| Channel opening kinetics | Time to peak | ms | Time to reach the maximum current |
| | T run-up | ms | Opening time between 10% and 90% of the max current |
| | Run-up slope | pA/s | Mean opening speed during T run-up |
| | Min slope | pA/s | Greatest opening speed |
| Channel closing kinetics | T run-down | ms | Closing time between 90% and 10% of the max current |
| | Run-down slope | pA/s | Mean closing speed during T run-down |
| | Max slope | pA/s | Greatest closing speed |
| | Tau | s | Closing time of 50% of the channels (half-life) |
| Desensitization | Slope | pA/s | Desensitization speed during the application of NMDA |

Validation of the Method with Reference Active Agents

The two reference compounds UBP141 and DQP1105 are tested first to validate the technical possibility of showing an antagonistic effect on the total NMDA currents of the rat embryonic neurons in the cultures. At a concentration of 10 μM, the two references show an antagonistic effect of more than −20% of the maximum current amplitude. At a concentration of less than 1 μM, the antagonistic effect is maintained at the same level at the very least for DQP1105. The reference molecules also show modifications in the NMDA channel opening and closing kinetics, and also on the desensitization. Table 3 shows the effect of the reference, DQP1105. A series of 12 peak parameters are chosen relative to the amplitude of the current and various kinetic properties of the NMDA channel, as mentioned above. These parameters represent a profile of effects on the NMDA neurotransmission.

Statistical Procedures

For each cell tested, the mean of the series of current peak parameters, as mentioned above, is calculated for the medicinal applications repeated (typically n=3) under each condition, namely: "NMDA", "NMDA+ test compound" and "NMDA wash". The effect of the compound is evaluated on several neurons (n=6 to 16) with a unilateral paired t-test, by comparing the "NMDA+ test compound" conditions with the "NMDA" conditions. The persistence of the compound effect after withdrawal is evaluated with a unilateral paired t-test, by comparing the "NMDA wash" conditions with "NMDA+ test compound". Statistical significance is achieved for p values<0.05. All the statistical analyses are performed with the JMP 12 software (SAS Institute Inc.).

TABLE 2 below summarizes the formulae of the compounds used and the indicator used in the table of results:

| Molecule | Formula |
|---|---|
| 1 | (structure: indole-ethyl linked to oxindole with OH, CH2-C(=O)-phenyl-3-Cl) |
| 2 | (structure: indole-ethyl linked to oxindole with OH, CH2-C(=O)-phenyl-2-Cl) |
| 3 | (structure: indole-ethyl linked to oxindole with OH, CH2-C(=O)-phenyl-2-F) |

Table 3 below summarizes the results obtained in vitro on the NMDA currents, the opening and closing kinetics and any desensitization of the channels, with examples of compounds according to the invention.

| | A. NMDA current | | | | |
|---|---|---|---|---|---|
| Molecule | Height (pA) | Width 50 (ms) | Peak area (pA·s) | Washable | Summary |
| 1 | −43 ± 8% (7)** | 0 ± 9% (7) | −37 ± 12% (7)* | No | Antagonist (4+) |
| 2 | −66 ± 10% (7)*** | −49 ± 14% (7)** | −65 ± 13% (7)** | Yes | Antagonist (6+) |
| 3 | −24 ± 7% (13)** | −10 ± 7% (13) | −16 ± 8% (13)* | (No/Yes) | Antagonist (2+) |

| | B. Channel opening kinetics | | | | |
|---|---|---|---|---|---|
| Molecule | Time to peak (ms) | T run-up (ms) | Run-up slope (pA/s) | Min slope (pA/s) | Washable |
| 1 | 1 ± 4% (7) | 3 ± 3% (7) | −45 ± 7% (7)*** | −35 ± 12% (7)* | No |
| 2 | −7 ± 4% (7) | −16 ± 13% (7) | −61 ± 10% (7)*** | −25 ± 9% (7)* | (Yes/No) |
| 3 | −5 ± 3% (13)* | −8 ± 6% (13) | −23 ± 5% (13)*** | −22 ± 4 (13)**** | (Yes/No) |

| | C. Channel closing kinetics | | | | |
|---|---|---|---|---|---|
| Molecule | T run-down (ms) | Run down slope (pA/s) | Max slope (pA/s) | Tau (s) | Washable |
| 1 | 12 ± 6% (7) | −48 ± 8% (7)*** | −27 ± 10% (7)* | 29 ± 13% (6)* | No |
| 2 | −15 ± 5% (7)* | −63 ± 13% (7)** | −28 ± 8% (7)** | 44 ± 28% (7) | (Yes/No) |
| 3 | 2 ± 4% (13) | −30 ± 8% (13)** | −22 ± 4% (13)**** | 17 ± 5 (13)** | No |

-continued

| Molecule | D. Desensitization | |
|---|---|---|
| | Slope (pA/s) | Washable |
| 1 | −59 ± 8% (7)*** | No |
| 2 | −70 ± 17% (7)** | (Yes) |
| 3 | −43 ± 8% (13)**** | No |

In the above table, the following elements mean: between ( ): Number of cells (no asterisk) NS,
*p < 0.05,
**p < 0.01,
***p < 0.001,
****p < 0.0001 and
NA: Not applicable.

This example thus clearly shows that examples of compounds according to the invention are NMDA receptor antagonists which may be useful in the prevention or treatment of pathologies involving the NMDA receptors of the central nervous system, in particular severe/resistant epilepsy and cognitive disorders resulting therefrom, notably autism, but also strokes, schizophrenia, degenerative diseases involving activation of the NMDA receptors such as Parkinson's disease and Alzheimer's disease, Rett's syndrome or amyotrophic lateral sclerosis, migraine, dementia and major depression.

REFERENCE LIST

1. Chen, H.-S. V.; Lipton, A. S. The chemical biology of clinically tolerated NMDA receptor antagonists. J. Neurochem. 2006, 97, 1611-1626.
2. Hallett, P. J.; Standaert, D. G. Rationale for and use of NMDA receptor antagonists in Parkinson's disease. Pharmacol. Ther. 2004, 102, 155-174.
3. Vance, K. M.; N., S.; Traynelis, S. F.; Furukawa, H. Ligand specific deactivation time course of GluN1/GluN2D NMDA receptors. Nat. Commun. 2011, 2, 294.
4. Goff, D. C.; Cather, C.; Gottlieb, J. D.; Evins, A. E.; Walsh, J.; Raeke, L.; Otto, M. W.; Schoenfeld, D.; Green, M. F. Once-weekly Dcycloserine effects on negative symptoms and cognition in schizophrenia: an exploratory study. Schizophr. Res. 2008, 106, 320-327).
5. "Approach for the synthesis of indole-3-propanol and its acetates from dihydropyran" Monatsh Chem. 2008, 139, 1475-1478.
6. Campos, K. R.; Woo, J. C. S.; Lee, S.; Tillyer, R. D. "A General Synthesis of Substituted Indoles from Cyclic Enol Ethers and Enol Lactones" Org. Lett. 2004, 6, 79-82.
7. Yang, J.-M.; Li, P.-H.; Wei, Y.; Tang, X.-Y.; Shi, M. "Gold(I)-catalyzed highly stereoselective synthesis of polycyclic indolines: the construction of four contiguous stereocenters" Chem. Commun. 2016, 52, 346-349
8. Kounosuke, O.; Abe, J.; Kanai, M. "Manganese-catalyzed aerobic dehydrogenative cyclization toward ring-fused indole skeletons" Org. Biomol. Chem. 2013, 11, 4569-4572.
9. Campaigne, E.; Homfeld, E. "Benzo[b]thiophene derivatives. XXV. Condensation and reductive alkylation of 3-aminoalkylbenzo[b]thiophenes with formaldehyde" J. Heterocycl. Chem. 1979, 16, 1321-1324.
10. Zhang, H. C.; Ye, H.; Moretto, A. F.; Brumfield, K. K.; Maryanoff, B. E. "Facile Solid-Phase Construction of Indole Derivatives Based on a Traceless, Activating Sulfonyl Linker" Org. Lett. 2000, 2, 89-92.
11. Lee, S. S.; Shen, W.; Zheng, X.; Jacobsen, I. C. "Preparation of tetrahydropyridinylthiophenecarboxylic acid derivatives for use as hepatitis C virus polymerase inhibitors" WO2014055142 A1.
12. Caroff, E.; Keller, M.; Kimmerlin, T.; Meyer, E.; "Preparation of 4-(benzoimidazol-2-yl)thiazole compounds and related aza derivatives as modulators of the CXCR3 receptor" WO2013114332 A1.
13. Kruegel, A. C.; Rakshit, S.; Li, X.; Sames, D.; "Constructing Iboga Alkaloids via C—H Bond Functionalization: Examination of the Direct and Catalytic Union of Heteroarenes and Isoquinuclidine Alkenes" J. Org. Chem. 2015, 80, 2062-2071.
14. Van Epps, D. E.; Jiang, G.-L.; Collette, A. L.; Horan, R. L.; Chen, J. S.; Altman, G. H.; Im, W.-B. "Compositions and improved soft tissue replacement methods" WO2013123272 A1.
15. Contour-Galcéra, M.-O.; Sidhu, A.; Plas, P.; Roubert, P. "3-Thio-1,2,4-triazoles, novel somatostatin sst2/sst5 agonists" Bioorg. Med. Chem. Lett. 2005, 15, 3555-3559.
16. Rong, Z.; Wang, W.; Jiang, Z. J.; Wang, K.; Zheng, X.-I.; Fu, H.-Y.; Chen, H.; Li, R.-X. "One-pot synthesis of 2-substituted benzo[b]furans via Pd-tetraphosphine-catalyzed coupling of 2-halophenols with alkynes" Chem. Commun. 2014, 50, 6023-6026.
17. Banerjee, T. S.; Paul, S.; Sinha, S.; Das, S. "Synthesis of iboga-like isoquinuclidines: Dual opioid receptor agonists having antinociceptive properties" Bioorg. Med. Chem. 2014, 22, 6062-6070.
18. Kruegel, A. C.; Rakshit, S.; Li, X.; Sames, D.; "Constructing Iboga Alkaloids via C—H Bond Functionalization: Examination of the Direct and Catalytic Union of Heteroarenes and Isoquinuclidine Alkenes" J. Org. Chem. 2015, 80, 2062-2071.
19. Contour-Galcera, M.-O.; Sidhu, A.; Plas, P.; Roubert, P. "3-Thio-1,2,4-triazoles, novel somatostatin sst2/sst5 agonists" Bioorg. Med. Chem. Lett. 2005, 15, 3555-3559.
20. S. M. Berge et al., J. Pharmaceutical Sciences, 1977, 66, 1-19
21. Remington Pharmaceutical Sciences, sixteenth edition, E. W. Martin (Mack Publishing Co., Easton, Pa., 1980)

The invention claimed is:
1. A compound of formula (I):

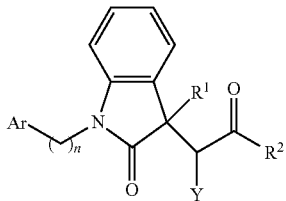
(I)

or a pharmaceutically acceptable salt thereof;
wherein:
$R^1$ represents H or OH;
$R^2$ represents:
methyl, ethyl, propyl, n-butyl, isopropyl, isobutyl, cyclopropyl, cyclobutyl, cyclopentyl or cyclohexyl;
a phenyl radical optionally substituted with one or more substituents chosen from F, Cl, Br, methyl, ethyl, CN, $CF_3$, OH, methoxy, $NH_2$ or $OCF_3$;
a pyridyl radical optionally substituted with one or more substituents chosen from F, Cl, Br, methyl, ethyl, $CF_3$, OH, methoxy, $NH_2$ or $OCF_3$; or
a benzofuryl radical having the structure

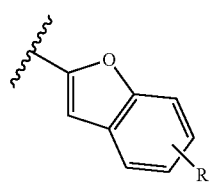

optionally substituted with one or more substituents R chosen from F, Cl, Br, methyl, ethyl, CN, $CF_3$, OH, methoxy, $NH_2$ or $OCF_3$;
a furyl radical having the structure

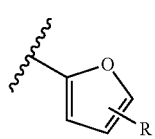

optionally substituted with one or more substituents R chosen from F, Cl, Br, methyl, ethyl, CN, $CF_3$, OH, methoxy, $NH_2$ or $OCF_3$;
a thiophene radical having the structure

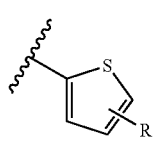

optionally substituted with one or more substituents R chosen from F, Cl, Br, methyl, ethyl, CN, $CF_3$, OH, methoxy, $NH_2$ or $OCF_3$; or a benzothiophene radical having the structure

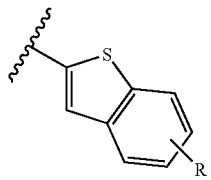

optionally substituted with one or more substituents R chosen from F, Cl, Br, methyl, ethyl, CN, $CF_3$, OH, methoxy, $NH_2$ or $OCF_3$;
Y represents H or a linear, branched or cyclic $C_{1-6}$ alkyl radical; or alternatively Y taken together with $R^2$ forms a 5-membered carbon ring;
n represents 0, 1, 2, 3 or 4;
Ar represents a bicyclic heterocycle having the structure:

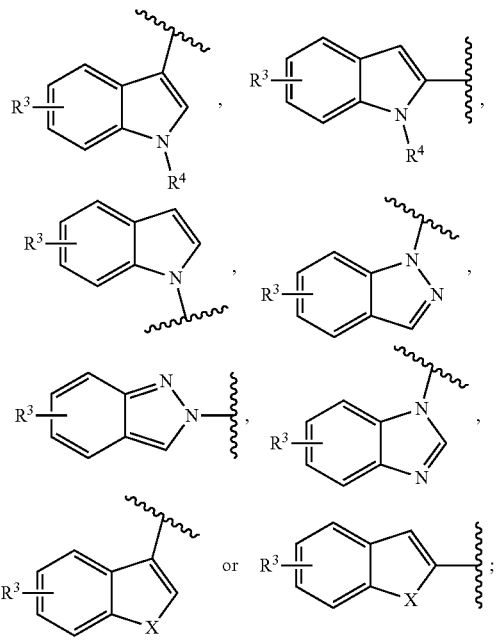

in which:
$R^3$ represents H, a halogen atom, a radical $-OR^5$ or $-NR^{6A}R^{6B}$; in which $R^5$ represents a H or linear, branched or cyclic $C_{1-6}$ alkyl radical; and $R^{6A}$ and $R^{6B}$ independently represent H, linear, branched or cyclic $C_{1-6}$ alkyl or $C_{6-10}$ aryl;
$R^4$ represents H; a linear, branched or cyclic $C_{1-6}$ alkyl radical; or a radical $-C(=O)R^7$ in which $R^7$ represents a linear, branched or cyclic $C_{1-6}$ alkyl radical; and
X represents O or S.

2. The compound as claimed in claim 1, having the following configuration:

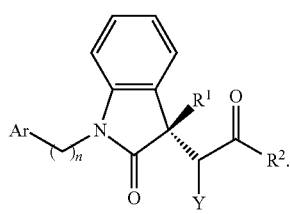

3. The compound as claimed in claim 1, wherein n represents 2 or 3.

4. The compound as claimed in claim 1, wherein $R^1$ represents OH.

5. The compound as claimed in claim 1, wherein Y represents H or methyl, or alternatively Y taken together with $R^2$ forms a 5-membered ring.

6. The compound as claimed in claim 1, in which, when Y taken together with $R^2$ forms a 5-membered ring; the carbon alpha to the ketone function which bears Y is a chiral center of R or S configuration, or alternatively is racemic.

7. The compound as claimed in claim 1, wherein Ar corresponds to the following formula:

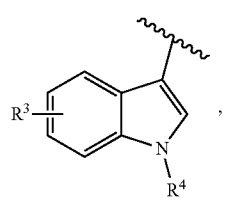

, wherein
$R^3$ represents H; a halogen atom chosen from F, Cl or Br; a radical —$OR^5$ in which $R^5$ represents H, methyl or ethyl; or a radical —$NR^{6A}R^{6B}$ in which $R^{6A}$ and $R^{6B}$ independently represent H, methyl or ethyl; and
$R^4$ represents H or methyl; or

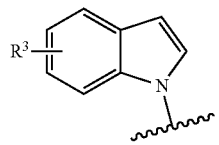

wherein
$R^3$ represents H; a halogen atom chosen from F, Cl or Br; a radical —$OR^5$ in which $R^5$ represents H, methyl or ethyl; or a radical —$NR^{6A}R^{6B}$ in which $R^{6A}$ and $R^{6B}$ independently represent H, methyl or ethyl.

8. The compound as claimed in claim 7, wherein Ar corresponds to the following formula:

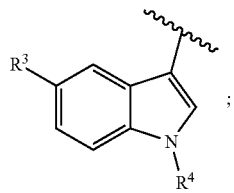

;

wherein $R^3$ and $R^4$ are as defined in claim 7.

9. The compound as claimed in claim 7, in which Ar corresponds to the following formula:

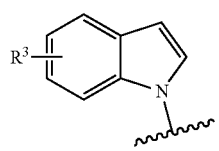

wherein $R^3$ represents H.

10. The compound as claimed in claim 1, wherein $R^2$ represents:
methyl, ethyl, isopropyl, isobutyl, cyclopropyl or cyclohexyl;
a phenyl radical which is unsubstituted or monosubstituted in the ortho, meta or para position with a substituent chosen from F, Cl, Br, methyl, ethyl, CN, $CF_3$, OH, methoxy, $NH_2$ or $OCF_3$; or
a pyridyl radical

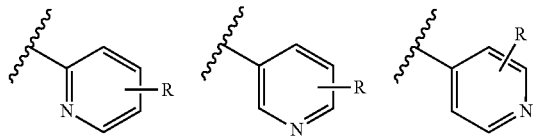

optionally substituted with a substituent R chosen from F, Cl, Br, methyl, ethyl, $CF_3$, OH, methoxy, $NH_2$ or $OCF_3$; or
a benzofuryl radical having the structure

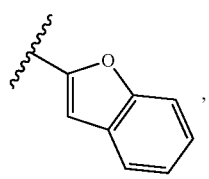 [SMILES: *c1cc2ccccc2o1]

, or
a furyl radical having the structure

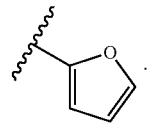

.

11. The compound as claimed in claim 1, corresponding to any one of the following structures:

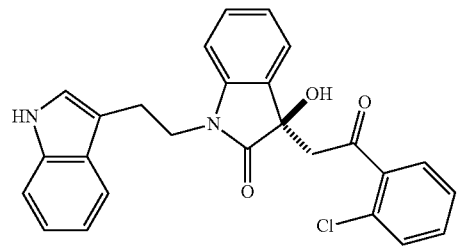

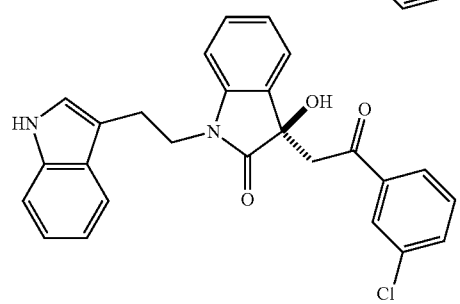

79
-continued
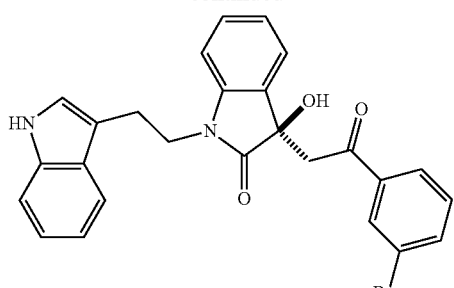
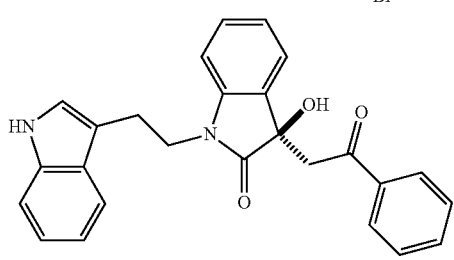
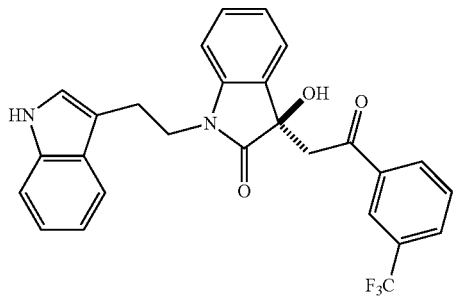
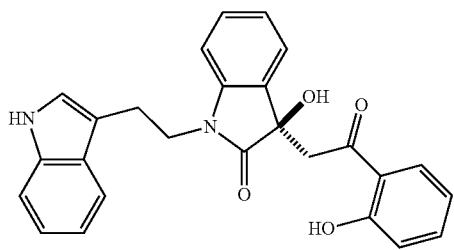
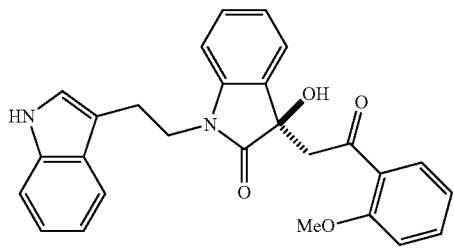
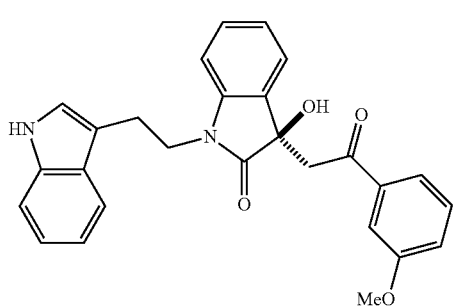
80
-continued
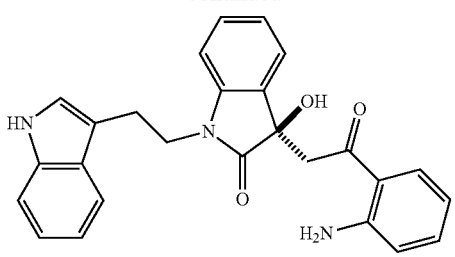
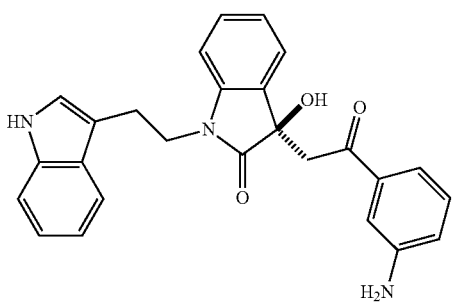
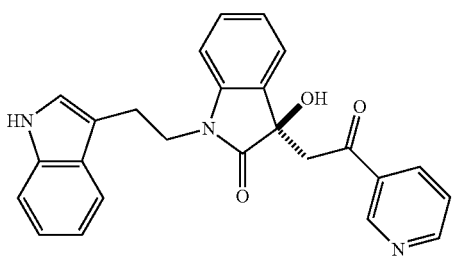
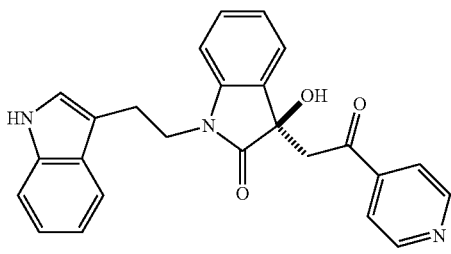
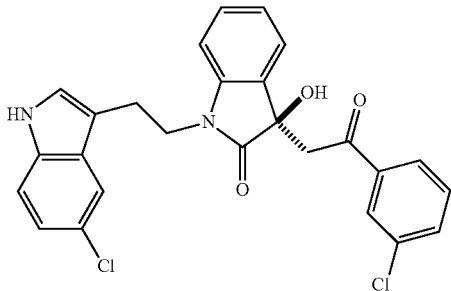
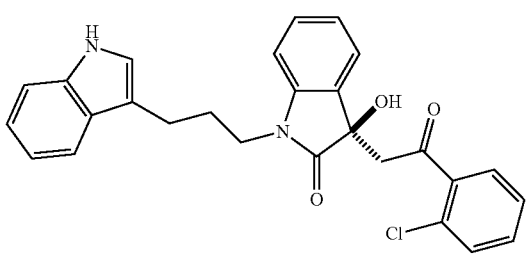

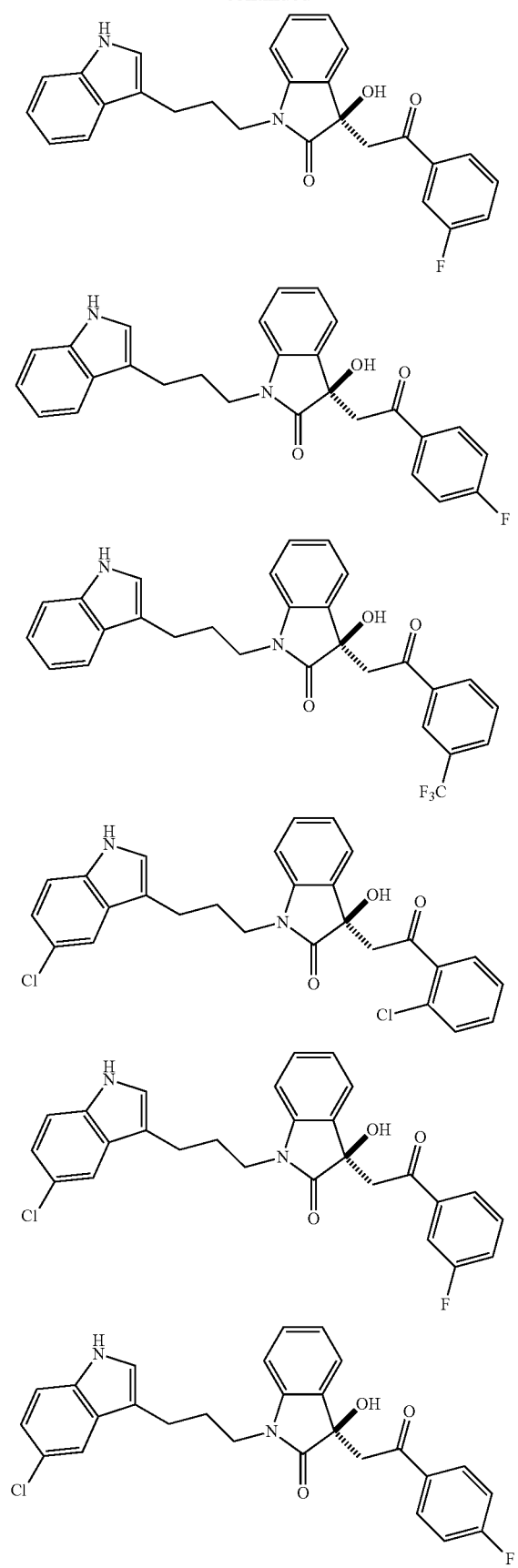
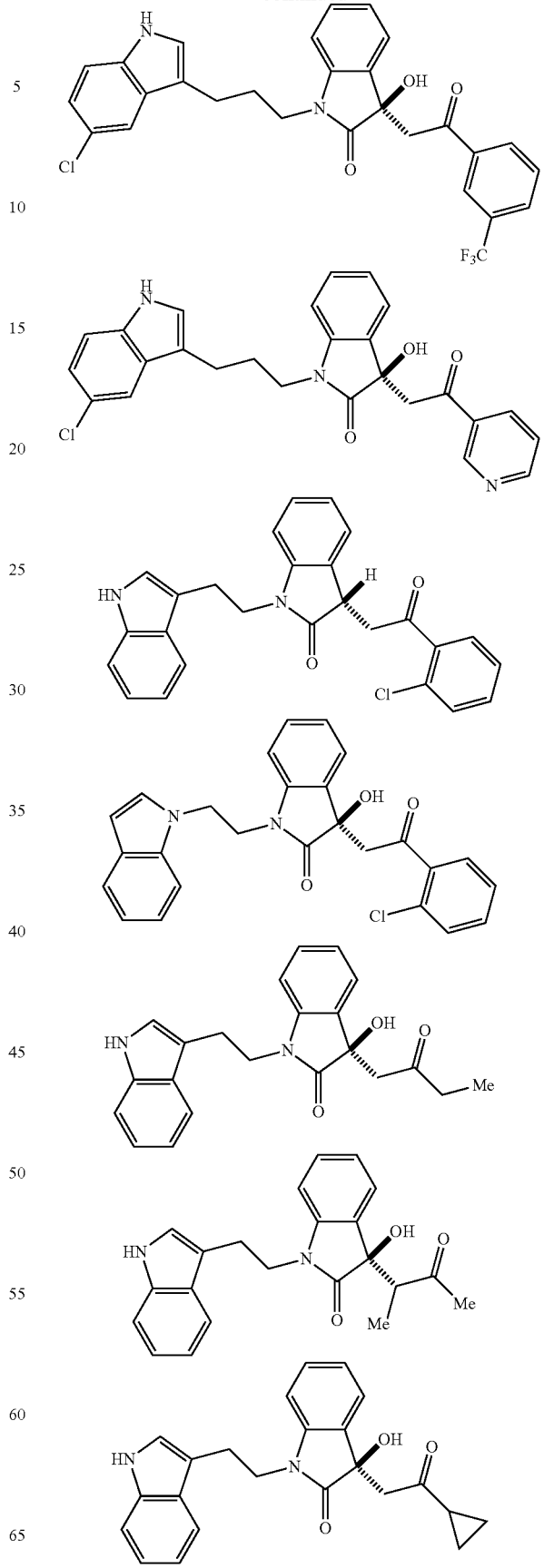

83
-continued
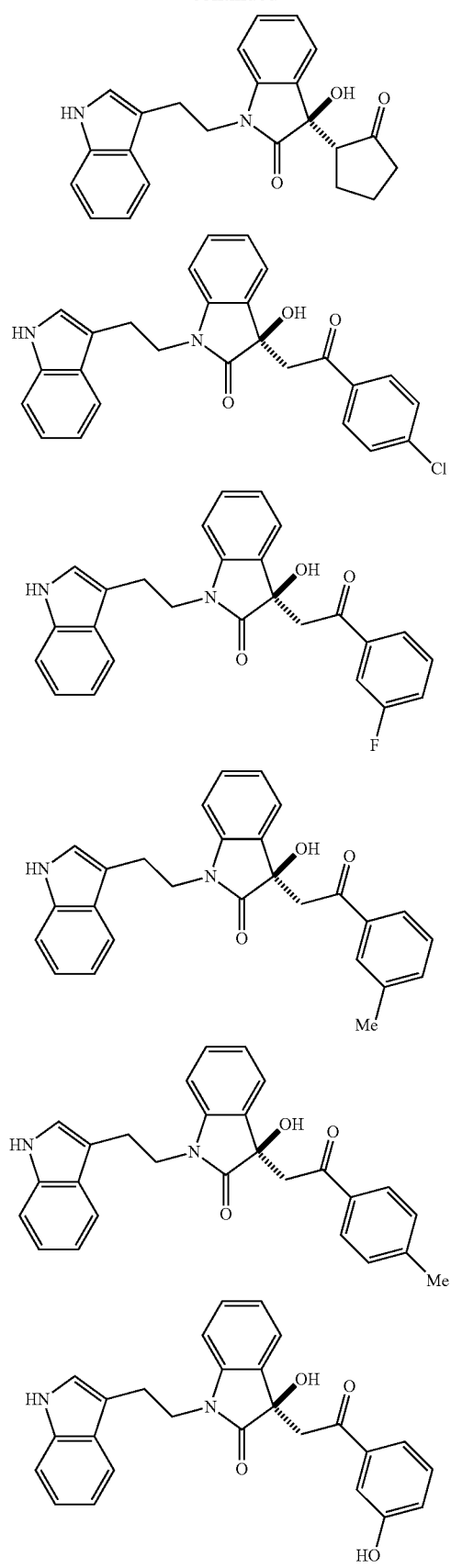
84
-continued
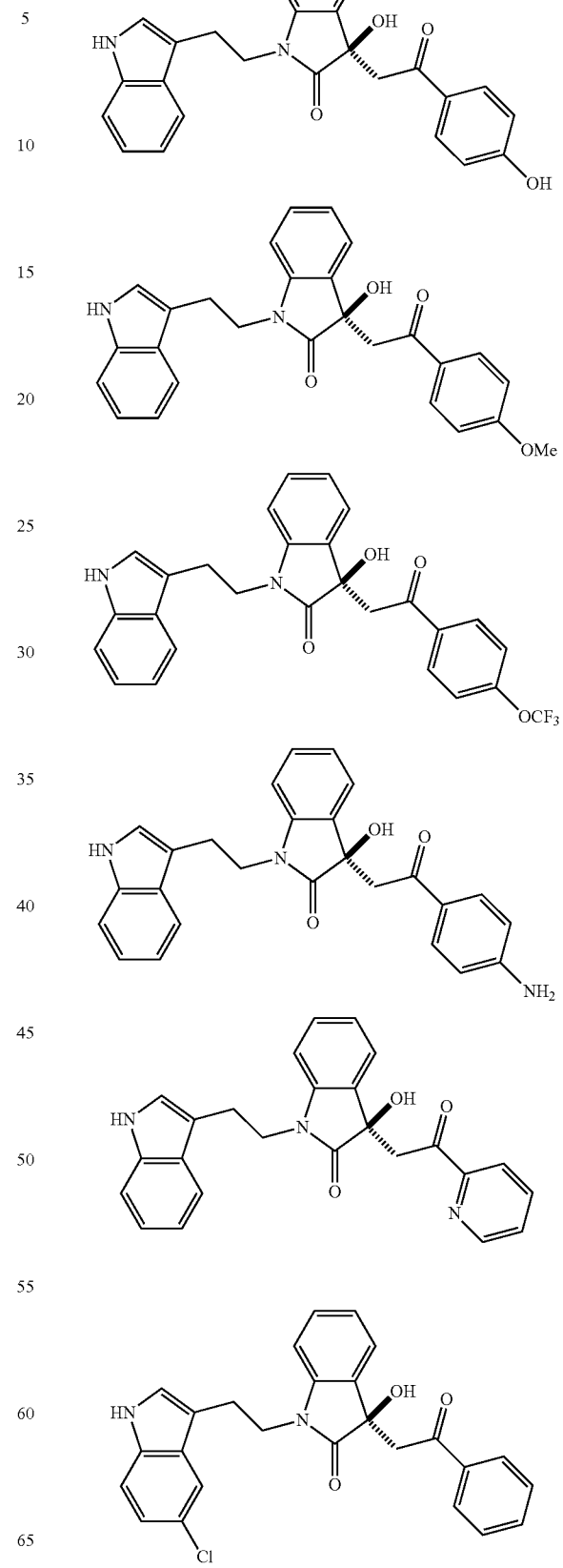

85 86
-continued -continued
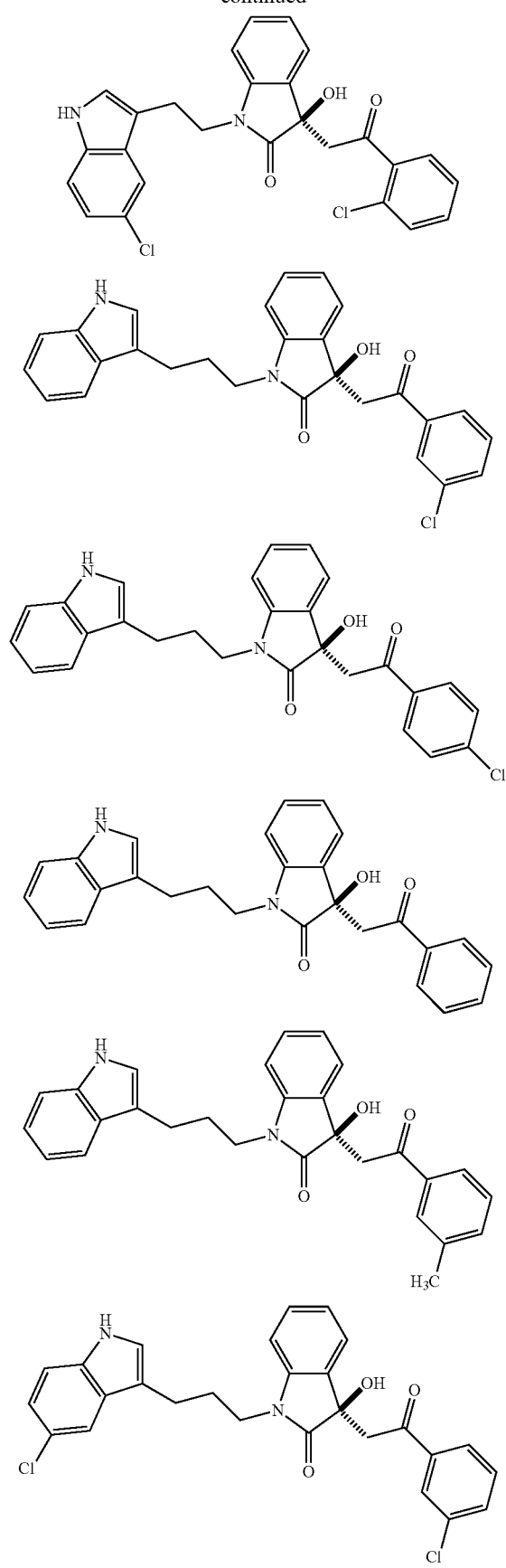
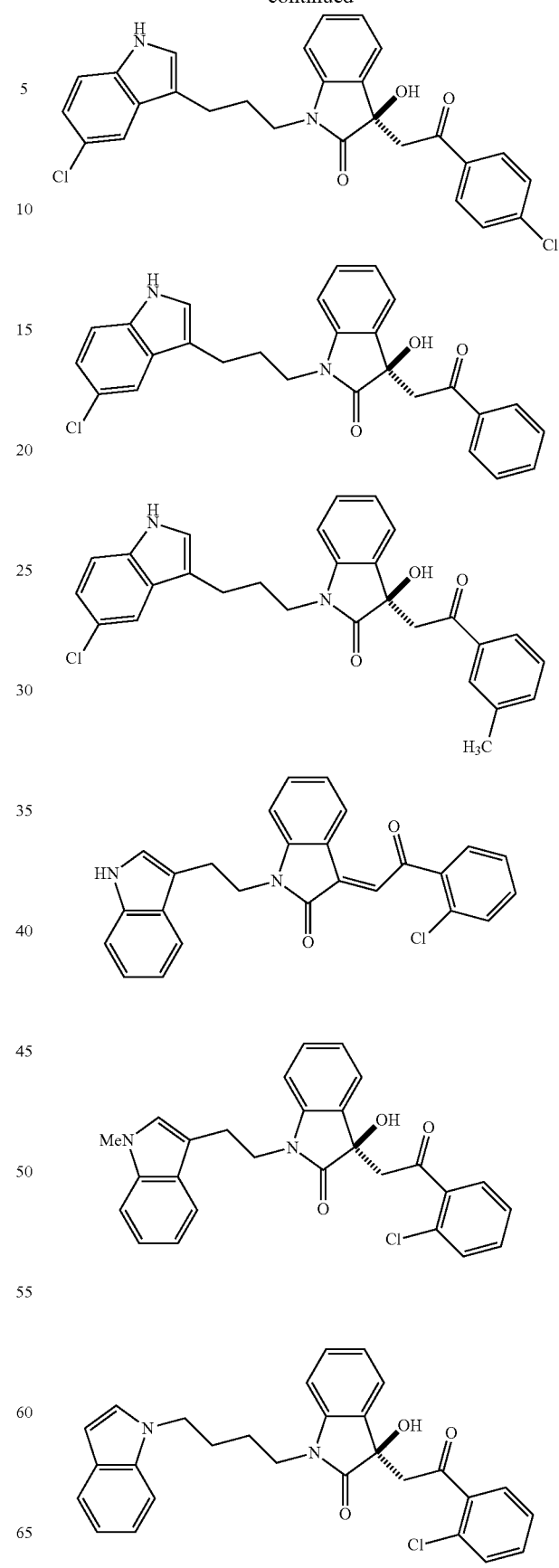

87

-continued

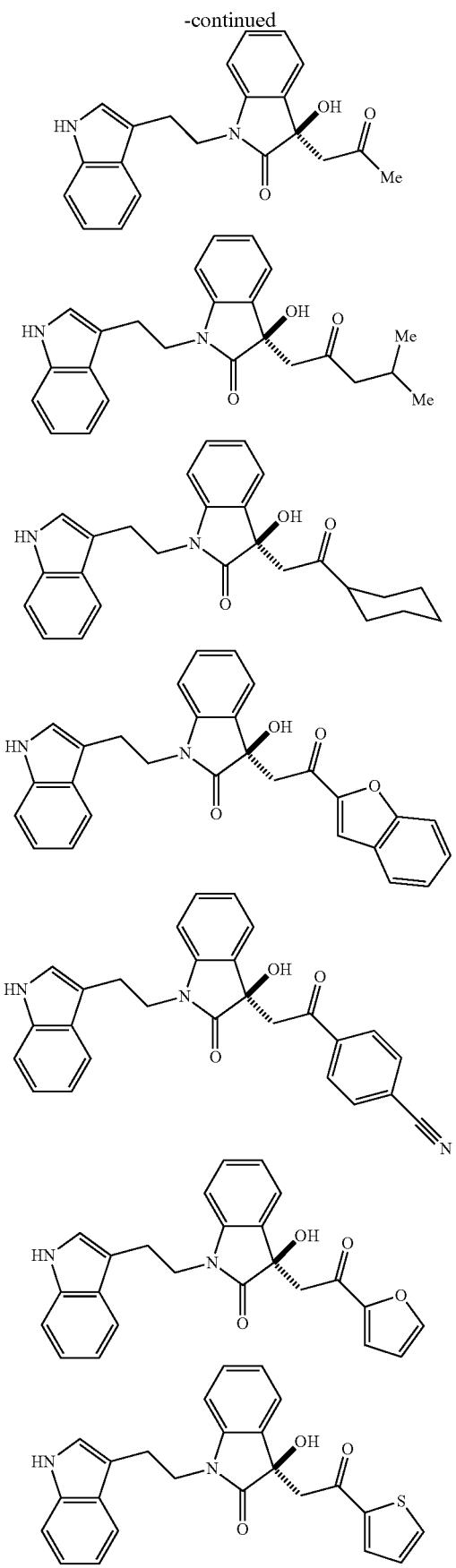

88

-continued

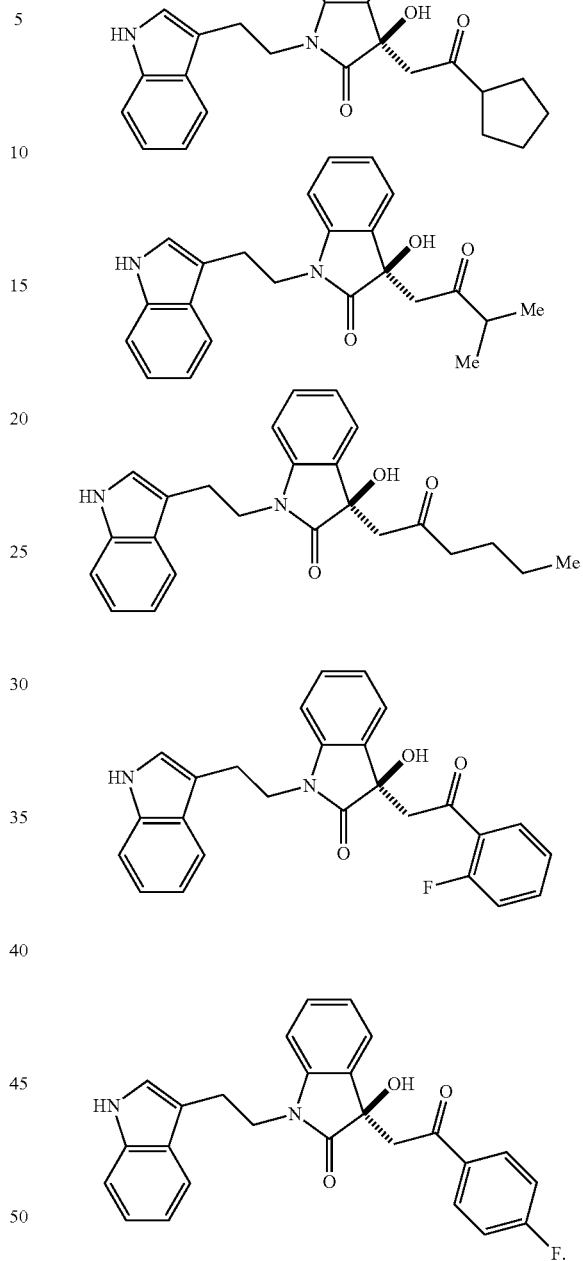

12. A pharmaceutical composition comprising a compound according to claim 1 and a pharmaceutically acceptable vehicle.

13. A method of treating a disease or pathology involving an N-methyl-D-aspartate receptor of the central nervous system, comprising administering the compound of claim 1 to a subject in need thereof, wherein the disease or pathology is, migraine, or major depression.

14. The compound as claimed in claim 1, wherein Y represents H.

* * * * *